US010005746B2

(12) United States Patent
Chan et al.

(10) Patent No.: US 10,005,746 B2
(45) Date of Patent: Jun. 26, 2018

(54) MOLECULAR CATALYSTS CAPABLE OF CATALYZING OXIDATION OF HYDROCARBONS AND METHOD FOR OXIDIZING HYDROCARBONS

(71) Applicants: Academia Sinica, Taipei (TW); National Taiwan University, Taipei (TW)

(72) Inventors: Sunney Ignatius Chan, South Pasadena, CA (US); Sheng-Fa Yu, New Taipei (TW); Penumaka Nagababu, New Taipei (TW); Suman Maji, West Bengal (IN); Ping-Yu Chen, Tainan (TW); Ravirala Ramu, New Taipei (TW); Chung-Yuan Mou, Taipei (TW); Chih-Cheng Liu, Keelung (TW)

(73) Assignees: ACADEMIA SINICA, Taipei (TW); NATIONAL TAIWAN UNIVERSITY, Taipei (TW)

(*) Notice: Subject to any disclaimer, the term of this patent is extended or adjusted under 35 U.S.C. 154(b) by 0 days. days.

(21) Appl. No.: 14/504,681

(22) Filed: Oct. 2, 2014

(65) Prior Publication Data

US 2015/0099876 A1    Apr. 9, 2015

Related U.S. Application Data

(60) Provisional application No. 61/886,676, filed on Oct. 4, 2013.

(51) Int. Cl.
C07C 29/48 (2006.01)
C07C 45/28 (2006.01)
(Continued)

(52) U.S. Cl.
CPC ........ *C07D 301/02* (2013.01); *B01J 31/2243* (2013.01); *C07C 29/48* (2013.01);
(Continued)

(58) Field of Classification Search
CPC .................. B01J 31/2243; B01J 2231/70; B01J 2231/72; B01J 2531/0216;
(Continued)

(56) References Cited

U.S. PATENT DOCUMENTS 3,015,657 A   1/1962   Geschickter et al.
3,037,983 A   6/1962   Geschickter et al.
(Continued)

FOREIGN PATENT DOCUMENTS

DE   1149366   5/1963
DE   3205647   8/1983
(Continued)

OTHER PUBLICATIONS

Hiltner, J. 5th Dessau Gas Engine Conference Mar. 26-27, 2009, pp. 1-3.*
(Continued)

*Primary Examiner* — Medhanit W Bahta
(74) *Attorney, Agent, or Firm* — Lathrop Gage LLP

(57) ABSTRACT

This invention relates to molecular catalysts and chemical reactions utilizing the same, and particularly to molecular catalysts for efficient catalytic oxidation of hydrocarbons, such as hydrocarbons from natural gas. The molecular catalytic platform provided herein is capable of the facile oxidation of hydrocarbons, for example, under ambient conditions such as near room temperature and atmospheric pressure.

18 Claims, 28 Drawing Sheets

(51) Int. Cl.
  *B01J 31/22* (2006.01)
  *C07D 301/02* (2006.01)
  *C07C 49/04* (2006.01)
  *C07C 49/303* (2006.01)
  *C07F 1/08* (2006.01)

(52) U.S. Cl.
  CPC .............. *C07C 45/28* (2013.01); *C07C 49/04* (2013.01); *C07C 49/303* (2013.01); *C07F 1/08* (2013.01); *B01J 2231/70* (2013.01); *B01J 2231/72* (2013.01); *B01J 2531/0216* (2013.01); *B01J 2531/0241* (2013.01); *B01J 2531/16* (2013.01); *C07C 2601/14* (2017.05); *C07C 2601/16* (2017.05); *Y02P 20/52* (2015.11)

(58) Field of Classification Search
  CPC ........... B01J 2531/0241; B01J 2531/16; C07C 29/48; C07C 45/28; C07C 49/04; C07C 49/303; C07C 2101/14; C07C 2101/16; C07D 301/02
  See application file for complete search history.

(56) References Cited

U.S. PATENT DOCUMENTS

| | | | |
|---|---|---|---|
| 3,093,676 | A | 6/1963 | Abramo et al. |
| 4,240,450 | A | 12/1980 | Grollier et al. |
| 4,778,813 | A | 10/1988 | Fenyes et al. |
| 8,338,600 | B2 | 12/2012 | Schindler et al. |
| 2009/0023215 | A1 | 1/2009 | Jessee et al. |
| 2013/0324761 | A1 | 12/2013 | Hutchings et al. |

FOREIGN PATENT DOCUMENTS

| | | |
|---|---|---|
| EP | 2671861 | 12/2013 |
| GB | 892789 | 3/1962 |
| WO | WO 1995/030792 | 11/1995 |
| WO | WO 2007/130073 | 11/2007 |
| WO | WO 2011/035064 | 3/2011 |
| WO | WO 2012/142622 | 10/2012 |
| WO | WO 2013/158127 | 10/2013 |
| WO | WO 2014/070687 | 5/2014 |

OTHER PUBLICATIONS

Chan, S. I. et al. Angew. Chem. Int. Ed. 2013 Supporting Information; pp. 1-16.*
Adebajo et al. (Mar. 9, 2012) "Recent Advances in Catalytic/Biocatalytic Conversion of Greenhouse Methane and Carbon Dioxide to Methanol and Other Oxygenates," In; Ch. 2. Greenhouse Gases—Capturing, Utilization and Reduction. Ed.: Liu, G. *In Tech.* p. 38.
Alayon et al. (Nov. 11, 2011) "Catalytic Conversion of Methane to Methanol over Cu-Mordenite," *Chem. Commun.* 48:404-406.
Blanksby et al. (2003) "Bond Dissociation Energies of Organic Molecules," *Acc. Chem. Res.* 36:255-263.
Burness et al. (1963) "Synthesis and Reactions of Quaternary Salts of Glyeidyl Amines," *J. Org. Chem.* 28:2283-2288.
Cambridge Crystallographic Data Center Home Page http://www.ccdc.cam.ac.uk/ [Last Accessed Oct. 29, 2014].
Chan et al. (2000) In; Fmoc Solid Phase Peptide Synthesis: A Practical Approach. Eds.: Chan, W.; White, P. *Oxford University Press.* Oxford, United Kingdom. pp. 41-77.
Chan et al. (2004) "Toward Delineating the Structure and Function of the Particulate Methane Monooxygenase from Methanotrophic Bacteria," *Biochemistry* 43:4421-4430.
Chan et al. (2007) "Redox Potentiometry Studies of Particulate Methane Monooxygenase: Support for a Trinuclear Copper Cluster Active Site," *Angew. Chem., Int. Ed.* 46(12):1992-1994.
Chan et al. (Feb. 18, 2013) "Efficient Oxidation of Methane to Methanol by Dioxygen Mediated by Tricopper Clusters," *Angew. Chem. Int. Ed.* 52:3731-3735.
Chan et al. (Jul. 8, 2008) "Controlled Oxidation of Hydrocarbons by the Membrane-Bound Methane Monooxygenase: The Case for a Tricopper Cluster," *Acc. Chem. Res.* 41(8):969-979.
Chan et al. (Sep. 2012) "Efficient Catalytic Oxidation of Hydrocarbons Mediated by Tricopper Clusters under Mild Conditions," *J. Catalysis* 293:186-194.
Chen et al. (2004) "The Copper Clusters in the Particulate Methane Monooxygenase (pMMO) from *Methylococcus capsulatus* (Bath)," *J. Chin. Chem. Soc.* 51:1081-1098.
Chen et al. (2006) "Theoretical Modeling of the Hydroxylation of Methane as Mediated by the Particulate Methane Monooxygenase," *J. Inorg. Biochem.* 100(4):801-809.
Chen et al. (2007) "Facile O-Atom Insertion into CC and CH Bonds by a Trinuclear Copper Complex Designed to Harness a Singlet Oxene," *Proc. Nat. Acad. Sci. USA* 104:14570-14575.
Chen et al. (Sep. 11, 2013) "Development of the Tricopper Cluster as a Catalyst for the Efficient Conversion of Methane into MeOH," *Chem. Cat. Chem.* 6(2):429-437.
Dietl et al. (Mar. 16, 2012) "Thermal Hydrogen-Atom Transfer from Methane: The Role of Radicals and Spin States in Oxo-Cluster Chemistry," Angew. Chem., Int. Ed. 51:5544-5555.
Ding et al. (1984) "Inhibition of Dihydrofolic Reductase from Rat Liver by Bis (2,4-diaminoquinazol-6-yl-substituted amino)-alkyl or arylalkyl Derivatives," *Yiyao Gongye* 12:6-10. (English Abstract and drawings only).
Elango et al. (1997) "Crystal structure of the hydroxylase component of methane monooxygenase from *Methylosinus trichosporium* OB3b," *Protein Sci.* 6:556-568.
Feig et al. (1994) "Reactions of Non-Heme Iron(II) Centers with Dioxygen in Biology and Chemistry," *Chem. Rev.* 94:759-805.
Freni et al. (2000) "Hydrogen Production from Methane Through Catalytic Partial Oxidation Reactions," *J. Power Sour.* 87:28-38.
Friedle et al. (2010) "Current Challenges of Modeling Diiron Enzyme Active Sites for Dioxygen Activation by Biomimetic Synthetic Complexes," *Chem. Soc. Rev.* 39:2768-2779.
Groothaert et al. (2005) "Selective Oxidation of Methane by the bis(μ-oxo)dicopper Core Stabilized on ZSM-5 and Mordenite Zeolites," *J. Am. Chem. Soc.* 127:1394-1395.
Hammond et al. (Apr. 5, 2012) "Direct Catalytic Conversion of Methane to Methanol in an Aqueous Medium by Using Copper-Promoted Fe-ZSM-5," *Angew. Chem., Int. Ed.* 51:5129-5133.
Hanson et al. (1996) "Methanotrophic Bacteria," *Microbiol. Rev.* 60:439-471.
Hayashi et al. (1971) "Studies on Antitumor Substances. XII. Synthesis of Bis (2,3-epoxypropyl) amine Derivatives and the Reaction with Some Nucleophiles," *Chemical and Pharmaceutical Bulletin* 19(10):2003-2008.
Ho et al. (Jan. 30, 2014) "$CO_2$ Fixation by Dicopper(II) Complexes in Hypodentate Framework of $N_8O_2$," *Dalton Transactions* 43(17):6287-6290.
Kau et al. (1987) "X-Ray Absorption Edge Determination of the Oxidation State and Coordination Number of Copper. Application to the Type 3 Site in *Rhus vernicifera* Laccase and its Reaction with Oxygen," *J. Am. Chem. Soc.* 109:6433-6442.
Kitmitto et al. (2005) "Characterization and Structural Analysis of an Active Particulate Methane Monooxygenase trimer from *Methylococcus capsulatus* (Bath)," *Biochemistry.* 44(33):10954-65.
Lewis et al. (2004) "Reactivity of Dioxygen—Copper Systems," *Chem. Rev.* 104:1047-1076.
Li et al. (2009) "Resonant X-Ray Scattering and Absorption for the Global and Local Structures of Cu-modified Metallothioneins in Solution," *Biophys. J.* 97(2):609-617.
Lieberman et al. (2005) "Crystal Structure of a Membrane-Bound Metalloenzyme that Catalyses the Biological Oxidation of Methane," *Nature* 434:177-182.
Lipscomb (1994) "Biochemistry of the Soluble Methane Monooxygenase," *Annu. Rev. Microbiol.* 48:371-399.
Lunsford (2000) "Catalytic conversion of methane to more useful chemicals and fuels: a challenge for the 21st century," *Catalysis Today* 63:165-174.

(56) References Cited

OTHER PUBLICATIONS

Mahadevan et al. (2000) "Differential Reactivity between Interconvertible Side-On Peroxo and Bis-μ-oxodicopper Isomers Using Peralkylated Diamine Ligands," *J. Am. Chem. Soc.* 122:10249-10250.

Maji et al. (Feb. 22, 2012) "Dioxygen Activation of a Trinuclear $Cu^I Cu^I Cu^I$ Cluster Capable of Mediating Facile Oxidation of Organic Substrates: Competition between O-Atom Transfer and Abortive Intercomplex Reduction," *Chem. Eur. J.* 18:3955-3968.

NaGababu et al. (Dec. 3, 2013) "Developing an Efficient Catalyst for Controlled Oxidation of Small Alkanes Under Ambient Conditions," *Catal. Sci. Technol.* 4:930-935.

Nagababu et al. (Nov. 13, 2012) "Efficient Room-Temperature Oxidation of Hydrocarbons Mediated by Tricopper Cluster Complexes with Different Ligands," *Adv. Synth. Catal.* 354:3275-3282.

Nauli et al. (2007) "Polymer-Driven Crystallization," *Protein Sci.* 16:2542-2551.

Newville (2001) "IFEFFIT: Interactive XAFS Analysis and FEFF Fitting," *J. Synchrotron Rad.* 8:322-324.

Ng et al. (2008) "Probing the Hydrophobic Pocket of the Active Site in the Particulate Methane Monooxygenase (pMMO) from *Methylococcus capsulatus* (Bath) by Variable Stereoselective Alkane Hydroxylation and Olefin Epoxidation," *Chembiochem* 9(7):1116-1123.

Nguyen et al. (1998) "The Particulate Methane Monooxygenase from *Methylococcus capsulatus* (Bath) is a Novel Copper-Containing Three-Subunit Enzyme. Isolation and Characterization," *J. Biol. Chem.* 273(14):7957-7966.

Periana et al. (1993) "A Mercury-Catalyzed, High-Yield System for the Oxidation of Methane to Methanol," *Science* 259:340-343.

Periana et al. (1998) "Platinum Catalysts for the High-Yield Oxidation of Methane to a Methanol Derivative," *Science* 280:560-564.

Rosenzweig et al. (1993) "Crystal Structure of a Bacterial Non-Haem Iron Hydroxylase that Catalyses the Biological Oxidation of Methane," *Nature* 366:537-543.

Semrau et al. (2010) "Methanotrophs and copper," *FEMS Microbiol. Rev.* 34:496-531.

Shearer et al. (2005) "Substrate Oxidation by Copper-Dioxygen Adducts: Mechanistic Considerations," *J. Am. Chem. Soc.* 127:5469-5483.

Shilov et al. (1997) "Activation of C—H Bonds by Metal Complexes," *Chem. Rev.* 97:2879-2932.

Taki et al. (2001) "C—H Bond Activation of External Substrates with a Bis(μ-oxo)dicopper(III) Complex," *J. Am. Chem. Soc.* 123:6203-6204.

Tomita et al. (2008) "Direct Oxidation of Methane to Methanol at Low Temperature and Pressure in an Electrochemical Fuel Cell," *Angew. Chem., Int. Ed.* 47:1462-1464.

United States Environmental Protection Agency (Apr. 2011) "Inventory of U.S. Greenhouse Gas Emissions and Sinks 1990-2009," Document No. EPA 430-R-11-005.

Vincent et al. (1988) "Modeling the Dinuclear Sites of Iron Biomolecules: Synthesis and Properties of $Fe_2O(OAc)_2Cl_2(bipy)_2$ and its Use as an Alkane Activation Catalyst," *J. Am. Chem. Soc.* 110:6898-6900.

Xu et al. (1983) "Studies on Synthetic Antimalarials VI. Synthetic and Antimalarial Activity of Some Tripiperaquines," *Yaoxue Xuebao*. 18(1):20-24. (English Abstract and drawings only).

Yan et al. (1988) "Antitumor Effects of 66 Quinazolines and Pyrimidines in vitro," *Yiyao Gongye*. 19(9):396-400.—English Abstract only.

Yu et al. (2003) "Production of High-Quality Particulate Methane Monooxygenase in High Yields from *Methylococcus capsulatus* (Bath) with a Hollow-Fiber Membrane Bioreactor," *J. Bacteriol.* 185:5915-5924.

Zabinsky et al. (1995) "Multiple-Scattering Calculations of X-Ray-Absorption Spectra," *Phys. Rev. B*. 52:2995.

Zhou et al. (1986) *Yiyao Gongye*. 17(11):489-495. (English Abstract and drawings only).

\* cited by examiner

TEM micrographs of (a) MSN-TP and (b) Al-MSN30-ex samples. The structure of nanochannels display hexagonal arrangement.

MOLECULAR CATALYSTS CAPABLE OF CATALYZING OXIDATION OF HYDROCARBONS AND METHOD FOR OXIDIZING HYDROCARBONS

CROSS-REFERENCE TO RELATED APPLICATIONS

This application claims the benefit of U.S. Provisional Application No. 61/886,676, filed Oct. 4, 2013, which is hereby incorporated by reference in its entirety to the extent not inconsistent herewith.

STATEMENT REGARDING FEDERALLY SPONSORED RESEARCH OR DEVELOPMENT

Not applicable.

BACKGROUND OF INVENTION

The development of catalysts for efficient conversion of methane to methanol has received increasing attention in recent years with the search for alternative fuels to replace the dwindling supply of petroleum. Recent advancements in natural gas exploration and production technology have led to a dramatic increase in both natural gas production and known natural gas reserves. Natural gas is composed primarily of methane mixed with other volatile hydrocarbons such as ethane, propane, butanes, pentanes and hexanes. Although natural gas is used as a primary combustible fuel, there is a substantial interest in technologies that are capable of converting natural gas into a more efficient and transportable fuel. One potentially attractive conversion pathway is oxidation of natural gas into oxidation products, such as alcohols, which have higher specific energies, lower volatility and more chemical versatility.

Methanol has a range of commercial applications including its use as a feedstock for the manufacture of industrial chemicals (e.g. formaldehyde, di methyl ether, etc.), as a fuel or fuel additive (e.g., automobiles) and as a solvent for synthesis and manufacturing applications. Currently, the most common process for the synthesis of methanol is the reaction of carbon monoxide with hydrogen gas using a copper-based catalyst. This process is endothermic, however, and requires both high temperature (~250° C.) and pressure (50-100 atm). Natural gas or pure methane can be used as a feedstock to generate carbon monoxide and hydrogen, typically by reacting methane with steam using a nickel catalyst, which can be subsequently used to generate methanol. Again, however, this reaction is endothermic and requires high temperature (~850° C.) and high pressure (~40 atm). Thus, many conventional methods for converting methane to methanol are resource intensive and costly in that these methods require multiple steps, expensive catalysts and significant input of energy.

Direct conversion of methane to methanol, a gas-to-liquid process, is challenging because the C—H bond in methane has a very high bond-energy (104 kcal/mole) and, thus, is largely inert chemically. In addition, the methanol reaction product of this reaction is prone to further oxidation under many conditions, thereby make selective generation of methanol at high yields difficult. Similarly, the oxidation of short length alkanes other than methane to their corresponding alcohols is also challenging as the C—H bond energies in these molecules are just slightly lower than the C—H bond energy of methane, with similar problems of over-oxidation.

Methanotrophic bacteria, such as *Methylococcus capsulatus* and *Methylosinus trichosporium*, are capable of the facile conversion of methane to methanol even at ambient temperatures and pressures. These bacteria mediate oxidation of methanol by using the enzyme methane monooxygenase (MMO) and dioxygen [See, e.g., Chan, Sunney et al. (2004) Toward delineating the Structure and Function of the Particulate Methane Monooxygenase from Methanotropic Bacteria. *Biochemistry*, 43 (15), 4421-4430.] There are two different forms of MMO: particulate (pMMO) and soluble (sMMO). In particular, the pMMO enzyme exhibits amazing regiospecificity and stereoselectivity in the oxidation of straight-chain alkanes from C1 to C5.

Researchers have studied the biochemical reactions in which pMMO facilitates the conversion of alkanes to alkanols with a potential goal of producing a biomimetic catalyst capable of oxidizing hydrocarbons under ambient conditions. As a result of this research, consensus has begun to develop supporting an understanding that the enzyme incorporates a multicopper cluster as an active site for oxidation [See, e.g., Chan, Sunney et al. (2008) Controlled Oxidation of Hydrocarbons by the Membrane-Bound Methane Monooxygenase: The Case for a Tricopper Cluster, *Accounts of Chem. Research*, 41 (8), 969-979.] Such research has also demonstrated that enzymes such a sMMO and pMMO require tight kinetic control in order to efficiently regenerate the catalyst back to the precursor state, presenting a further challenge for development of a viable biomimetic catalyst. The need for kinetic control can be potentially circumvented in transition metal catalysts, however, by operating a metal ion at a higher oxidation state or by resorting to Fenton-type chemistry [See, e.g., Chan, Sunney et al. (2012) Efficient catalytic oxidation of hydrocarbons mediated by tricopper clusters under mild conditions, *J. Catal.*, 293, 186-194.] Previous efforts to develop functional biomimetic catalysts based on sMMO or pMMO have met with limited success.

PCT Publication No. WO 2011/035064 A2 to Elgammal, for example, is directed to a catalyst for the oxidation of hydrocarbons comprising a 1,2,4-triazole ligand and a transition metal. The catalyst operates at temperatures between 0-25° C. The yield of the oxidation of methane to methanol, however, remains under 30%, and in most cases much lower. Further, in reactions to oxidize larger alkanes, low regiospecificity and over-oxidation both remain major problems.

It will be appreciated from the foregoing that there is currently a need in the art for an improved molecular catalyst and methods capable of the facile oxidation of hydrocarbons at ambient conditions with a high degree of regiospecificity and stereoselectivity. In particularly, catalysts are needed that provide catalytic oxidation of hydrocarbons from natural gas exhibiting high turnover frequencies and specificity for formation of useful oxidation products, such as methanol.

SUMMARY OF THE INVENTION

This invention relates to molecular catalysts and chemical reactions utilizing the same, and particularly to molecular catalysts for efficient catalytic oxidation of hydrocarbons, such as hydrocarbons from natural gas. The molecular catalytic platform provided herein is capable of the facile oxidation of hydrocarbons, for example, under ambient conditions such as near room temperature and atmospheric pressure.

Provided herein are catalyst compositions, catalytic systems, and methods for the oxidation of hydrocarbons. Copper catalysts and catalyst formulations of the invention, for example, exhibit high catalytic efficiencies, and with good turnovers and oxidation product yields under conditions supporting a range of industrial and energy-related applications. The invention provides a versatile class of copper catalysts having compositions that can be tailored to achieve substrate recognition and product selectivity for the oxidation of range of hydrocarbons to specific oxidation products. The present copper catalysts and methods are flexible, thereby supporting both heterogeneous and homogeneous catalysis. The present copper catalyst systems are capable of kinetically driven catalyst activation and regeneration steps using a variety of readily available oxidizing agents and reducing agents.

In an embodiment, the invention provides biomimetic copper catalysts and catalytic methods for efficient conversion of gas-phase hydrocarbons in natural gas to transportable fuels and commercially useful products, such as akanols, alkanones and alkane diols. In an embodiment, the catalyst compositions and methods combine substrate recognition and oxygen atom transfer supporting an efficient pathway for regiospecific alkane hydroxylation. Specific copper catalysts of the invention, for example, are capable of efficient oxidation of methane to methanol at high yields without over oxidation. In an embodiment, for example, the yield of methanol from the catalytic oxidation of methane is greater than or equal to 75%, and optionally for some applications greater than or equal to 90%. This aspect of the invention is particularly auseful for providing a selective pathway for conversion of natural gas to liquid oxidation products under ambient conditions.

In an aspect, the invention provides a catalytic process for oxidation of a hydrocarbon to generate an oxidation product, the process comprising the steps of: (i) contacting the hydrocarbon with a copper catalyst in the presence of an oxidizing agent, thereby generating the oxidation product and (ii) regenerating the copper catalyst, wherein the copper catalyst comprises a tricopper complex comprising three Cu ions and a ligand (L) having the formula (FX1):

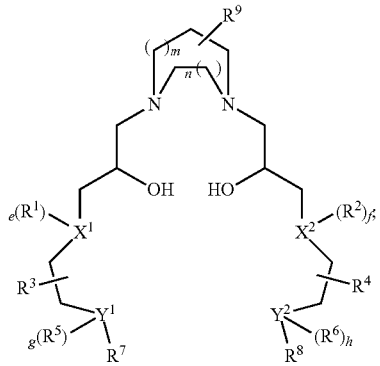

(FX1)

wherein each of m and n is independently 0, 1, or 2; each of e, f, g and h is independently 0 or 1; each of $X^1$ and $X^2$ is independently O, S, N, or P; each of $Y^1$ and $Y^2$ is independently O, S, N, or P; and each of $R^1$, $R^2$, $R^3$, $R^4$, $R^5$, $R^6$, $R^7$, $R^8$ and $R^9$ is independently hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_2$-$C_{10}$ alkenyl, $C_3$-$C_{10}$ cycloalkenyl, $C_2$-$C_{10}$ alkynyl, $C_5$-$C_{10}$ alkylaryl, —OH, —CH$_2$OH, —COOH, —NH$_2$ or —CO(NH$_2$); or wherein $R^1$ and $R^5$ combine to form a $C_2$-$C_4$ alkylene thereby forming with adjacent moieties a hetero- cyclic 6-, 7- or 8-member ring and wherein $R^2$ and $R^6$ combine to form a $C_2$-$C_4$ alkylene, thereby forming with adjacent moieties a heterocyclic 6-, 7- or 8-member ring. In an embodiment, the hydrocarbon, the copper catalyst, and the oxidizing agent are brought in physical contact with each other, for example, in a solution phase, a liquid phase, a gas phase or a combination of these. In an embodiment, for example, regenerated copper catalyst subsequently participates in further reaction with oxidizing agent and hydrocarbon to achieve catalytic oxidation.

In certain embodiments, the hydrocarbon is a $C_1$-$C_8$ alkane or a $C_2$-$C_6$ alkene, including linear, branch and cyclical $C_1$-$C_8$ alkanes or a $C_2$-$C_6$ alkenes. Optionally, for example, the hydrocarbon is methane, ethane, propane, butane, or any combination of these. In an embodiment, the hydrocarbon is methane from a natural gas sample. In a specific embodiment, for example, the hydrocarbon is provided in a sample of natural gas. In embodiments, the oxidation product is an alcohol, a ketone or a diol. In certain embodiments for example, the oxidation product is an alcohol, such as methanol, ethanol, propanol. In embodiments, the catalytic process is capable of occurring at a temperature equal to or less than 25° C. and at a pressure equal to or less than 1 atmosphere.

In the context of formula (FX1), designation of e, f, g, and/or h as 0, corresponds to a ligand having the formula (FX1) wherein $R^1$, $R^2$, $R^5$ and $R^6$, respectively, is not present; and designation of e, f, g, and/or h as 1 corresponds to a ligand having the formula (FX1) wherein $R^1$, $R^2$, $R^5$ and $R^6$, respectively, is present. In specific embodiments, the invention provides methods, formulations and compositions using the present copper catalysts comprising ligand (L) having formula (FX1) wherein one or more of e, f, g, and/or h is 0, for example, wherein $X^1$, $X^2$, $Y^1$ or $Y^2$ is sulfur or oxygen. In a specific embodiment, the invention provides methods, formulations and compositions using the present copper catalysts comprising ligand (L) having formula (FX1) wherein each of m and n is 0 or 1. In a specific embodiment, the invention provides methods, formulations and compositions using the present copper catalysts comprising ligand (L) having formula (FX1) wherein each of e, f, g and h is 1. In a specific embodiment, the invention provides methods, formulations and compositions using the present copper catalysts comprising ligand (L) having formula (FX1) wherein each of e, f, g, and h is 0.

An important property of the invention is the catalytic nature of the oxidation process, for example, wherein after generation of an oxidation product the copper catalyst is efficiently regenerated and, thus, available to subsequently react with hydrocarbon and further generate oxidation product. In some embodiments, for example, the process is characterized by catalyst activation and regeneration steps that are capable of kinetic control, for example, via providing sufficient oxidizing agents and/or reducing agents to kinetically drive catalyst activation and regeneration steps. The present processes are compatible with a range of different oxidizing agents for kinetically driving catalyst activation, such as hydrogen peroxide, air and oxygen, and reducing agents for kinetically driving catalyst regeneration, such as hydrogen peroxide. In some embodiments, the invention comprises the step of providing the oxidizing agent at a concentration and/or amount capable of kinetically driving catalysis activation. In some embodiments, the invention comprises the step of providing the reducing agent at a concentration and/or amount capable of kinetically driving catalysis regeneration. In some embodiments, the invention comprises the step of replenishing the concentrations and/or amounts of the copper catalyst, oxidizing agent, the reducing agent, hydrocarbon or combinations thereof.

In a specific embodiment, the copper catalyst comprises a tricopper complex having the formula: $[Cu^I Cu^I Cu^I(L)_q]$, wherein is q is an integer from 1 to 3 and wherein L is the ligand. In an embodiment, for example, the copper catalyst comprises a tricopper complex having the formula $[Cu^I Cu^I - Cu^I(L)]+$, wherein L is the ligand. In an embodiment, for example, the copper catalyst is contacted with a oxidizing agent, thereby generating an oxygenated activated copper catalyst. In embodiments, for example, the oxygenated activated copper catalyst has the formula $[Cu^{II}Cu^{II}(\mu-O)_2 Cu^{III}(L)]^+$, wherein L is the ligand. In a specific embodiment, the oxygenated activated copper catalyst has the formula (FX12):

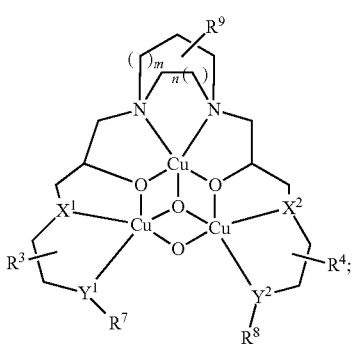

(FX12)

wherein m, n, $X^1$, $X^2$, $Y^1$, $Y^2$, $R^3$, $R^4$ $R^7$, $R^8$ and $R^9$ are as defined in connection with (FX1).

In a certain embodiment, for example, the oxygenated activated copper catalyst has a structure characterized by a hydrophobic binding pocket providing for molecular recognition of the hydrocarbon, for example, providing molecular recognition for methane, ethane, propane and/or butane.

In an embodiment, a reaction of the oxygenated activated copper catalyst and the hydrocarbon results in transfer of an O atom from the oxygenated activated copper catalyst to the hydrocarbon, thereby generating the oxidation product. Optionally, for example, the O atom is inserted into a C—H bond of the hydrocarbon, for example to generate an alcohol, ketone or diol reaction product. In an embodiment, the reaction of the oxygenated activated copper catalyst and the hydrocarbon generates a partially oxidized tricopper complex reaction product, the process further comprising reducing the partially oxidized tricopper complex reaction product so as to regenerate the copper catalyst. In an embodiment, for example, the partially oxidized tricopper complex reaction product has the formula, $[Cu^I Cu^{II}(\mu-O)Cu^{II}(L)]^+$, wherein L is the ligand. In an embodiment, the partially oxidized tricopper complex reaction product has the formula (FX13):

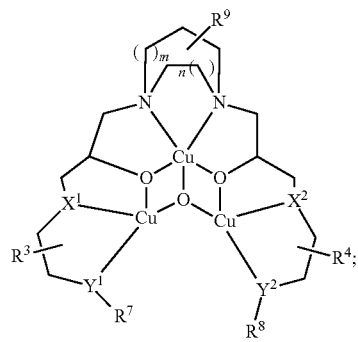

(FX13)

wherein m, n, $X^1$, $X^2$, $Y^1$, $Y^2$, $R^3$, $R^4$ $R^7$, $R^8$ and $R^9$ are as defined in connection with (FX1). In a specific embodiment, the step of reducing the partially oxidized tricopper complex reaction product is achieved by contacting the partially oxidized tricopper complex reaction product with a reducing agent. Optionally, for example, the reducing agent is $H_2O_2$, $H_2$, formate or ascorbate. In embodiments, the copper catalyst regenerated in the process contacts a hydrocarbon in the presence of an oxidizing agent in the catalytic process to further generate the oxidation product. In a specific embodiment, the hydrocarbon is methane, ethane and propane; and the oxidation product does not undergo further oxidation when in contact with said copper catalyst in the presence of said oxidizing agent. In some embodiments, the process is characterized by a turnover frequency greater than or equal to $1 \times 10^{-2}$ sec$^{-1}$, optionally for some applications greater than or equal $5 \times 10^{-2}$ sec$^{-1}$. In some embodiments, the process is characterized by a catalytic efficiency greater than or equal to 50%, optionally for some applications greater than or equal to 75%.

In specific embodiments, the copper catalyst further comprises one or more counterions, for example, counterions are selected from the group consisting of: $ClO_4^-$ or $BF_4^-$.

The invention provides a class of copper catalyst having compositions useful for oxidation of a range of hydrocarbons. In embodiment, for example, the composition of the ligand (L) of the copper catalysts is capable of being tuned to provide selectivity as to molecular recognition of the hydrocarbon substrate and/or specificity as to the composition of the oxidation product. As will be recognized by one having skill in the art, any of the copper catalysts described herein can be used in the present processes and formulations.

In an embodiment, for example, the processes and compositions of the invention include a catalyst comprising a ligand (L) having formula (FX1) wherein each of $X^1$, $X^2$, $Y^1$ and $Y^2$ is N. In certain embodiments, the processes and compositions of the invention include a catalyst comprising a ligand (L) having formula (FX1) wherein $R^1$ and $R^5$ join together to form an ethylene or propylene group, thereby forming with an adjacent ethylenediamine group a piperazine ring or a homopiperazine ring; and wherein $R^2$ and $R^6$ join together to form an ethylene or propylene group, thereby forming with an adjacent ethylenediamine group a piperazine ring or a homopiperazine ring. In an embodiment, the processes and compositions of the invention include a catalyst comprising a ligand (L) having formula (FX1) wherein each of $R^7$ and $R^8$ is an ethyl group. In certain embodiments, the processes and compositions of the invention include a catalyst comprising a ligand (L) having formula (FX1) wherein each of $R^7$ and $R^8$ is not a methyl group. In embodiments, each of $R^3$, $R^4$, $R^7$, $R^8$ and $R^9$ is independently hydrogen or $C_1$-$C_5$alkyl. In a specific embodiment, the processes and compositions of the invention include a catalysts comprising a ligand (L) having formula (FX1) wherein, $R^9$ is —OH, —$CH_2OH$, —COOH, —$NH_2$ or —$CO(NH_2)$.

In certain embodiments, the copper catalyst comprises a ligand (L) having the formula (FX2) or (FX3):

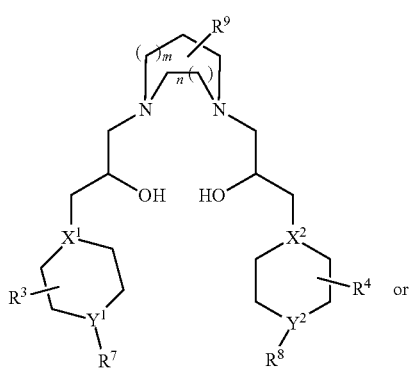

(FX2)

(FX3)

wherein m, n, $X^1$, $X^2$, $Y^1$, $Y^2$, $R^3$, $R^4$ $R^7$, $R^8$ and $R^9$ are as defined in connection with (FX1); and optionally wherein each of $R^7$ and $R^8$ is an ethyl group. In some embodiments, each of $R^7$ and $R^8$ is not a methyl group.

In certain embodiments, the copper catalyst comprises a ligand (L) having the formula (FX4) or (FX5):

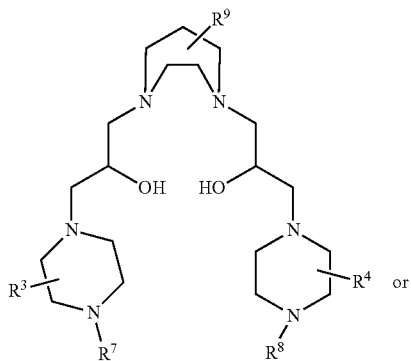

(FX4)

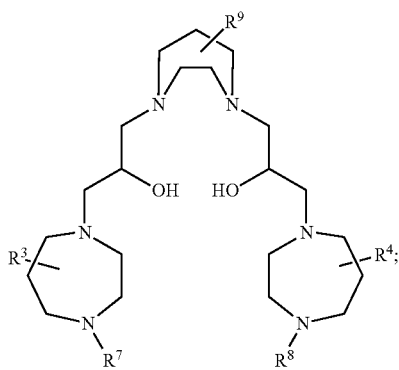

(FX5)

wherein $R^3$, $R^4$ $R^7$, $R^8$ and $R^9$ are as defined in connection with (FX1); and optionally wherein each of $R^7$ and $R^8$ is an ethyl group. In some embodiments, each of $R^7$ and $R^8$ is not a methyl group.

In certain embodiments, the copper catalyst comprises a ligand (L) having the formula (FX6) or (FX7):

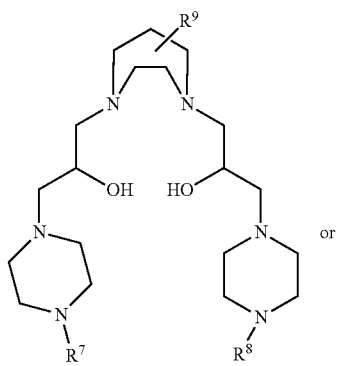

(FX6)

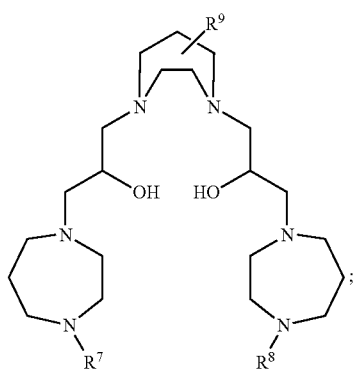

(FX7)

wherein $R^7$ and $R^8$ are as defined in connection with (FX1); and optionally wherein each of $R^7$ and $R^8$ is an ethyl group. In other embodiments, each of $R^7$ and $R^8$ is not a methyl group.

In certain embodiments, the copper catalyst comprises a ligand (L) having the formula (FX8):

(FX8)

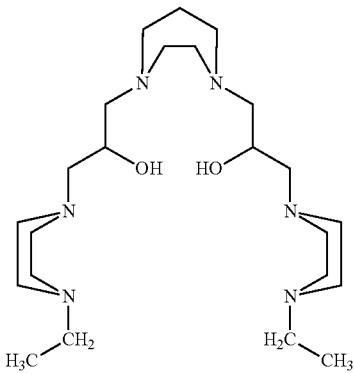

In certain embodiments, the copper catalyst comprises a ligand (L) having the formula (FX9), (FX10) or (FX11):

(FX9)

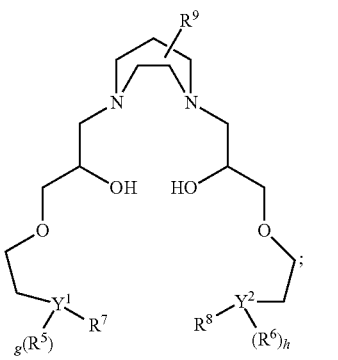

(FX10)

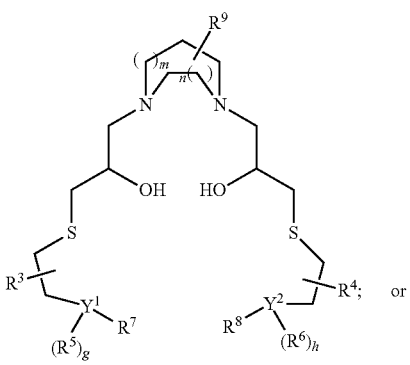

(FX11)

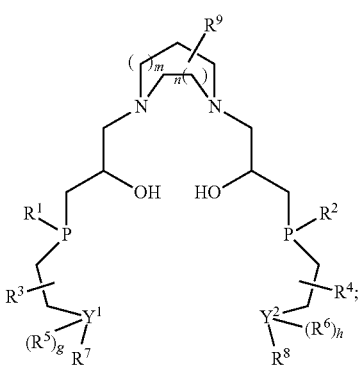

wherein m, n, $Y^1$, $Y^2$, $R^1$-$R^9$ are as defined in connection with (FX1); and optionally wherein each of $R^7$ and $R^8$ is an ethyl group. In some embodiments, each of $R^7$ and $R^8$ is not a methyl group.

The copper catalysts provided herein are capable of oxidizing a wide range of hydrocarbons with a high degree of regiospecificity and little, or in some embodiments, no over-oxidation. Some copper catalysts of the invention, for example, are capable of alkane oxidation to an alkanol oxidation product such as methanol, with little or no over oxidation to generate alkanone or alkane diol products. Specific ligands have a high degree of recognition in regards to the composition of the hydrocarbon substrate.

In an embodiment, the hydrocarbon is a linear, branched or cyclic alkane or alkene. In another embodiment, for example, the hydrocarbon is a $C_1$-$C_8$ alkane or $C_2$-$C_8$ alkene, and optionally for some embodiments, $C_1$-$C_6$ alkane or $C_2$-$C_6$ alkene; and optionally for some embodiments, $C_1$-$C_4$ alkane or $C_2$-$C_4$ alkene. Optionally, for example the hydrocarbon is methane, ethane, propane and/or n-butane. Optionally, for example the hydrocarbon is methane. In embodiments, the hydrocarbon is provided in a gas phase, liquid phase, solution phase or a combination of these.

The disclosed catalyst compositions are versatile with regard to oxidizing agents useful in the present catalytic processes. In a specific embodiment, for example, the oxidizing agent is one or more dioxygen species. Optionally, the oxidizing agent is $O_2$, $H_2O_2$ or air. In embodiments, the oxidizing agent is provided in a gas phase, a liquid phase, a solution phase or a combination of these.

The catalytic methods, compositions, and processes of the present invention are capable of facilitating both homogeneous and heterogeneous catalysis.

In some embodiments, the copper catalyst is a homogeneous catalyst. For example, in embodiments, the copper catalyst, the oxidizing agent and the hydrocarbon are each dissolved in a solvent, wherein the step of contacting the hydrocarbon with a copper catalyst in the presence of an oxidizing agent is carried out in a homogeneous solution comprising the solvent, the dissolved copper catalyst, the oxidizing agent and the hydrocarbon.

In embodiments, the copper catalyst is a heterogeneous catalyst. In some embodiments, the copper catalyst is immobilized on one or more surfaces of a solid catalyst support scaffold. In an embodiment, the catalyst support scaffold is a plurality of mesoporous particles. In certain embodiments, the copper catalyst is covalently attached to a polymeric support, glass bead, or resin. In an embodiment, for example, the solid catalyst support scaffold comprises a mesoporous material and the copper catalyst is provided on the surface of a network of pores with the mesoporous material. In some embodiments, the solid catalyst support scaffold is mesoporous silicate, mesoporous carbon, or a sol gel. In an embodiment, the mesoporous material is functionalized to generate a negatively charged surface to achieve immobilization of the copper catalyst. In an embodiment, for example, mesoporous material is functionalized by contact with Al or anionic 3-trihydroxysilypropyl-methyl-phosphonate (TP).

In some embodiments, for example, the concentration of the catalyst in the solution is selected from the range of 0.1-10 mM, and optionally for some applications 1-10 mM. In some embodiments, the concentration of the hydrocarbon in the solution is selected from the range of 0.01-1.0 M, and optionally for some applications 0.1-0.5 M. In some embodiments, the concentration of the oxidizing agent in the solution is selected from the range of 0.05-1 M, optionally for some embodiments 0.05-0.2 M. In some embodiments the solvent is a nonaqueous solvent, such as a polar or nonpolar nonaqueous solvent. In a specific embodiment, the solvent is MeCN or a fluorohydrocarbon, for example, a $C_2$-$C_{20}$ fluorocarbon. In an embodiment, the one or more solvents is not $H_2O$.

The catalyst methods, compositions, and processes contained herein support a range of applications including conversion of natural gas to liquid fuels. The catalyst methods and compositions are useful for a variety of other applications including production of industrially and commercially relating materials, including alcohols, ketones and diols. In an embodiment, for example, (i) the hydrocarbon is methane and the oxidation product is methanol; (ii) the hydrocarbon is ethane and the oxidation product is ethanol; (iii) the hydrocarbon is propane and the oxidation product is propanol; (iv) the hydrocarbon is butane and the oxidation product is butanol, butanone, 2,3-butanediol; or (v) any combination of these. In an embodiment, the catalytic process is for converting a natural gas into a liquid fuel. In an embodiment, the process is for oxidizing hydrocarbons in a petroleum sample, including samples derived from petroleum processing. In an embodiment, for example, the catalytic process is for alkane hydroxylation of methane, ethane, propane or butane in natural gas. In embodiments, the natural gas is converted into the liquid fuel using air as the oxidizing agent. In an embodiment, for example, the natural gas is converted to the liquid fuel comprising an alcohol, a ketone, a diol or any combination of these. In an embodiment, for example, the process is for generating the liquid fuel at a temperature equal to or less than 25° C. and at a pressure equal to or less than 1 atmosphere. In some embodiments, the process further comprises isolating the oxidation product. In embodiments, the process further comprises recovering the copper catalyst.

In an embodiment, the invention provides a process for conversion of natural gas into one or more liquid fuels. In an embodiment, for example, the invention provides a catalytic process for converting a natural gas into a liquid fuel, the process comprising the steps of: (i) contacting methane, ethane, propane or butane in the natural gas with a copper catalyst in the presence of an oxidizing agent; thereby generating the liquid fuel comprising an alcohol, a ketone, a diol or any combination of these; and (ii) regenerating the copper catalyst; wherein, the copper catalyst comprises a tricopper complex comprising three Cu ions and a ligand (L) having the formula (FX1):

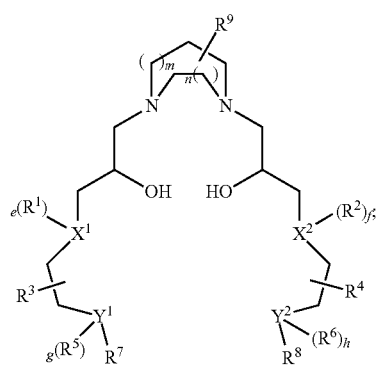

(FX1)

wherein each of m and n is independently 0, 1, or 2; each of e, f, g and h is independently 0 or 1; each of $X^1$ and $X^2$ is independently O, S, N, or P; each of $Y^1$ and $Y^2$ is independently O, S, N, or P; and each of $R^1$, $R^2$, $R^3$, $R^4$, $R^5$, $R^6$, $R^7$, $R^8$ and $R^9$ is independently hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_2$-$C_{10}$ alkenyl, $C_3$-$C_{10}$ cycloalkenyl, $C_2$-$C_{10}$ alkynyl, $C_5$-$C_{10}$ alkylaryl, —OH, —$CH_2OH$, —COOH, —$NH_2$ or —$CO(NH_2)$; or wherein $R^1$ and $R^5$ combine to form a $C_2$-$C_4$ alkylene thereby forming with adjacent moieties a heterocyclic 6-, 7- or 8-member ring and wherein $R^2$ and $R^6$ combine to form a $C_2$-$C_4$ alkylene, thereby forming with adjacent moieties a heterocyclic 6-, 7- or 8-member ring. In an embodiment, for example, the oxidizing agent is air.

In another aspect, the invention provides catalysts formulations for the oxidation of hydrocarbons. In an embodiment, for example, the invention provides a catalyst formulation for oxidation of a hydrocarbon to generate an oxidation product, the formulation comprising: (i) a copper catalyst comprising a tricopper complex comprising three Cu ions and a ligand (L) having the formula (FX1):

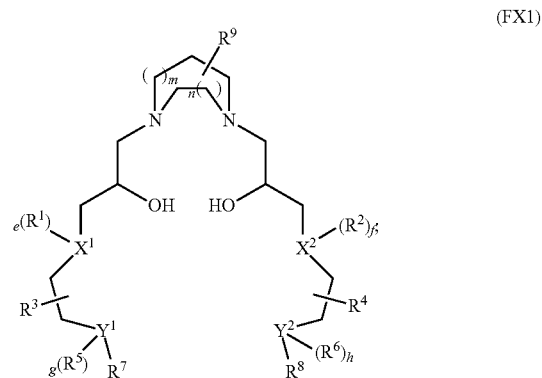

(FX1)

wherein, wherein each of m and n is independently 0, 1, or 2; each of e, f, g and h is independently 0 or 1; each of $X^1$ and $X^2$ is independently O, S, N, or P; each of $Y^1$ and $Y^2$ is independently O, S, N, or P; and each of $R^1$, $R^2$, $R^3$, $R^4$, $R^5$, $R^6$, $R^7$, $R^8$ and $R^9$ is independently hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_2$-$C_{10}$ alkenyl, $C_3$-$C_{10}$ cycloalkenyl, $C_2$-$C_{10}$ alkynyl, $C_5$-$C_{10}$ alkylaryl, —OH, —$CH_2OH$, —COOH, —$NH_2$ or —$CO(NH_2)$; or wherein $R^1$ and $R^5$ combine to form a $C_2$-$C_4$ alkylene thereby forming with adjacent moieties a heterocyclic 6-, 7- or 8-member ring and wherein $R^2$ and $R^6$ combine to form a $C_2$-$C_4$ alkylene, thereby forming with adjacent moieties a heterocyclic 6-, 7- or 8-member ring; (ii) an oxidizing agent for activating the copper catalyst to generate an oxygenated activated copper catalyst that reacts with the hydrocarbon to generate the oxidation product and a partially oxidized tricopper complex reaction product; and (iii) a reducing agent for reducing the partially oxidized tricopper complex reaction product so as to regenerate the copper catalyst. In an embodiment, for example, the catalyst formulation further comprises one or more solvents. As will be generally understood by those having skill in the art, any of the catalyst compositions, oxidizing agents, reducing agents and solvents described herein can be used in the present catalyst formulations. In some embodiments, for example, the copper catalyst of the present catalyst formulations comprises the tricopper complex having the formula $[Cu^ICu^ICu^I(L)]^+$, wherein L is the ligand. In embodiments, for example, the oxygenated activated copper catalyst of the present catalyst formulations has the formula $[Cu^{II}Cu^{II}(\mu$-

$O)_2Cu^{III}(L)]^+$, wherein L is the ligand. In embodiments, for example, the partially oxidized tricopper complex reaction product has the formula $[Cu^ICu^{II}(\mu-O)Cu^{II}(L)]^+$, wherein L is the ligand. In embodiments, the oxidizing agent is $O_2$, $H_2O_2$ or air. Additionally, in some embodiments, the reducing agent is $H_2O_2$, $H_2$, formate or ascorbate. Optionally, in some embodiments, the oxidizing agent and the reducing agent are each $H_2O_2$. In an embodiment, the catalyst formulation of the invention is in a substantially purified state.

In another aspect, the present invention provides copper complex compositions, for example, for applications in chemical synthesis. In an embodiment, for example, the invention provides a copper complex comprising three Cu ions and a ligand (L) having the formula (FX1):

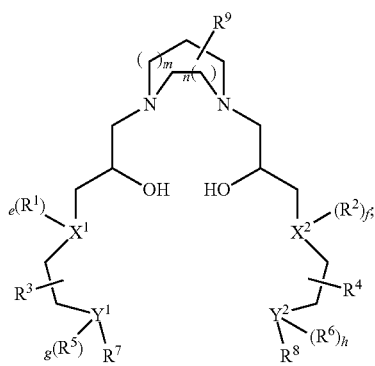

(FX1)

wherein, each of m and n is independently 0, 1, or 2; each of e, f, g and h is independently 0 or 1; each of $X^1$ and $X^2$ is independently O, S, N, or P; each of $Y^1$ and $Y^2$ is independently O, S, N, or P; and each of $R^1$, $R^2$, $R^3$, $R^4$, $R^5$, $R^6$, $R^7$, $R^8$ and $R^9$ is independently hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_2$-$C_{10}$ alkenyl, $C_3$-$C_{10}$ cycloalkenyl, $C_2$-$C_{10}$ alkynyl, $C_5$-$C_{10}$ alkylaryl, —OH, —$CH_2OH$, —COOH, —$NH_2$ or —$CO(NH_2)$; or wherein $R^1$ and $R^5$ combine to form a $C_2$-$C_4$ alkylene thereby forming with adjacent moieties a heterocyclic 6-, 7- or 8-member ring and wherein $R^2$ and $R^6$ combine to form a $C_2$-$C_4$ alkylene, thereby forming with adjacent moieties a heterocyclic 6-, 7- or 8-member ring; with the proviso that when each of $R^1$ and $R^5$ and $R^2$ and $R^6$ independently combine to form a $C_2$-$C_4$ alkylene thereby generating a heterocyclic 6-, 7- or 8-member ring with adjacent moieties, then $R^7$ and $R^8$ are not each methyl; with the proviso that when $R^1$ and $R^2$ are each methyl then $R^7$ and $R^8$ are not each methyl; with the proviso that when $R^1$ and $R^2$ are each ethyl then $R^7$ and $R^8$ are not each ethyl. In certain embodiments, the copper complex further comprises one or more counterions. In embodiments, the copper complex has the formula $[Cu^ICu^ICu^I(L)]^+$, wherein L is the ligand. In embodiments, the copper complex has a structure characterized by a hydrophobic binding pocket providing for molecular recognition of methane, ethane, propane, or butane. In a specific embodiment, for example, each of m and n is 1; wherein each of $X^1$, $X^2$, $Y^1$ and $Y^2$ is N; and wherein $R^1$ and $R^5$ join together to form an ethylene or propylene group, thereby forming with an adjacent ethylenediamine group a piperazine ring or a homopiperazine ring; and wherein $R^2$ and $R^6$ join together to form an ethylene or propylene group, thereby forming with an adjacent ethylenediamine group a piperazine ring or a homopiperazine ring. Optionally, for example, wherein each of $R^7$ and $R^8$ is an ethyl group. In an embodiment, the copper complex of the invention is in a substantially purified state.

In another aspect, the invention provides an oxygenated copper complex having the formula $[Cu^{II}Cu^{II}(\mu-O)_2Cu^{III}(L)]^+$; wherein L is a ligand having the formula (FX1):

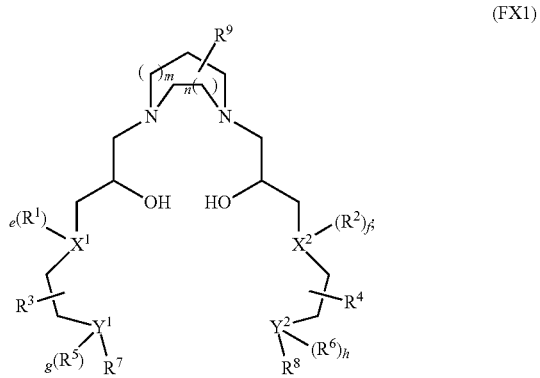

(FX1)

wherein each of m and n is independently 0, 1, or 2; each of e, f, g and h is independently 0 or 1; each of $X^1$ and $X^2$ is independently O, S, N, or P; each of $Y^1$ and $Y^2$ is independently O, S, N, or P; and each of $R^1$, $R^2$, $R^3$, $R^4$, $R^5$, $R^6$, $R^7$, $R^8$ and $R^9$ is independently hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_2$-$C_{10}$ alkenyl, $C_3$-$C_{10}$ cycloalkenyl, $C_2$-$C_{10}$ alkynyl, $C_5$-$C_{10}$ alkylaryl, —OH, —$CH_2OH$, —COOH, —$NH_2$ or —$CO(NH_2)$; or wherein $R^1$ and $R^5$ combine to form a $C_2$-$C_4$ alkylene thereby forming with adjacent moieties a heterocyclic 6-, 7- or 8-member ring and wherein $R^2$ and $R^6$ combine to form a $C_2$-$C_4$ alkylene, thereby forming with adjacent moieties a heterocyclic 6-, 7- or 8-member ring; with the proviso that when each of $R^1$ and $R^5$ and $R^2$ and $R^6$ independently combine to form a $C_2$-$C_4$ alkylene thereby generating a heterocyclic 6-, 7- or 8-member ring with adjacent moieties, then $R^7$ and $R^8$ are not each methyl; with the proviso that when each of $R^1$ and $R^5$ and $R^2$ and $R^6$ independently combine to form a $C_2$-$C_4$ alkylene thereby generating a heterocyclic 6-, 7- or 8-member ring with adjacent moieties, then $R^5$ and $R^8$ are not each ethyl; with the proviso that when $R^1$ and $R^2$ are each methyl then $R^7$ and $R^8$ are not each methyl; with the proviso that when $R^1$ and $R^2$ are each ethyl then $R^7$ and $R^8$ are not each ethyl. In an embodiment, the oxygenated copper complex has the formula (FX12). In some embodiments, the oxygenated copper complex reacts with a hydrocarbon to generate a partially oxidized tricopper complex reaction product having the formula $[Cu^ICu^{II}(\mu-O)Cu^{II}(L)]^+$, wherein L is the ligand. In an embodiment, for example, the partially oxidized tricopper complex reaction product has the formula (FX13).

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

Statements Regarding Chemical Compounds and Nomenclature

Figure 1:
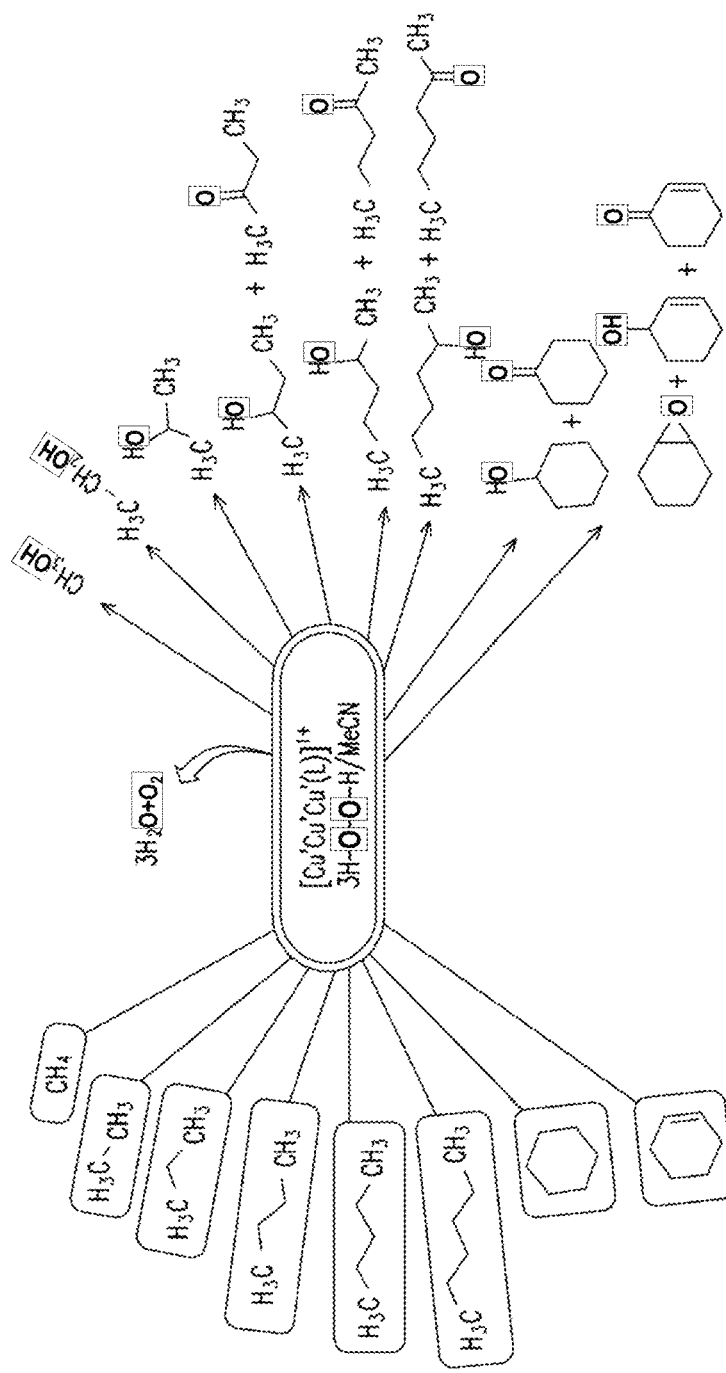
FIG. 1 illustrates oxidation of n-alkanes, cycloalkanes and cycloalkenes by hydrogen peroxide ($H_2O_2$) catalyzed by the tricopper complex [Cu$^I$Cu$^I$Cu$^I$(7-N-Etppz)]$^{1+}$ at room temperature in Example 1 of this invention.

In an embodiment, a composition or compound of the invention, such as a copper catalyst composition or formulation, is isolated or substantially purified. In an embodiment, an isolated or purified compound is at least partially isolated or substantially purified as would be understood in the art. In an embodiment, a substantially purified composition, compound or formulation of the invention has a chemical purity of 95%, optionally for some applications 99%, optionally for some applications 99.9%, optionally for some applications 99.99%, and optionally for some applications 99.999% pure.

Many of the molecules disclosed herein contain one or more ionizable groups. Ionizable groups include groups from which a proton can be removed (e.g., —COOH) or added (e.g., amines) and groups that can be quaternized (e.g., amines). All possible ionic forms of such molecules and salts thereof are intended to be included individually in the disclosure herein. With regard to salts of the compounds herein, one of ordinary skill in the art can select from among a wide variety of available counterions that are appropriate for preparation of salts of this invention for a given application. In specific applications, the selection of a given anion or cation for preparation of a salt can result in increased or decreased solubility of that salt.

The compounds of this invention can contain one or more chiral centers. Accordingly, this invention is intended to include racemic mixtures, diasteromers, enantiomers, tautomers and mixtures enriched in one or more stereoisomer. The scope of the invention as described and claimed encompasses the racemic forms of the compounds as well as the individual enantiomers and non-racemic mixtures thereof.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc. valence states.

As used herein, the term "substituted" refers to a compound wherein a hydrogen is replaced by another functional group.

As is customary and well known in the art, hydrogen atoms in formulas (FX1)-(FX13) are not always explicitly shown, for example, hydrogen atoms bonded to the carbon atoms of alkylene groups and/or alicyclic rings are not always explicitly shown in formulas (FX1)-(FX13). The structures provided herein, for example in the context of the description of formulas (FX1)-(FX13), are intended to convey to one of reasonable skill in the art the chemical composition of compounds of the methods and compositions of the invention, and as will be understood by one of skill in the art, the structures provided do not indicate the specific positions of atoms and bond angles between atoms of these compounds.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alky group having a ring structure such as ring structure comprising 3-30 carbon atoms, optionally 3-20 carbon atoms and optionally 2-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, 7- or 8-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO— refers to $CH_3O$—.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9- or 10-member carbon ring(s) and particularly those having a 3-, 4-, 5-, 6-, 7- or 8-member ring(s). The carbon rings in cycloalkenyl groups can also carry alkyl groups. Cycloalkenyl groups can include bicyclic and tricyclic alkenyl groups. Alkenyl groups are optionally substituted. Substituted alkenyl groups include among others those that are substituted with alkyl or aryl groups, which groups in turn can be optionally substituted. Specific alkenyl groups include ethenyl, prop-1-enyl, prop-2-enyl, cyclo-prop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms.

Aryl groups include groups having one or more 5-, 6-, 7- or 8-member aromatic rings, including heterocyclic aromatic rings. The term heteroaryl specifically refers to aryl groups having at least one 5-, 6-, 7- or 8-member heterocyclic aromatic rings. Aryl groups can contain one or more fused aromatic rings, including one or more fused heteroaromatic rings, and/or a combination of one or more aromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those that are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocyclic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein provided in a covalently bonded configuration in the compounds of the invention at any suitable point of attachment. In embodiments, aryl groups contain between 5 and 30 carbon atoms. In embodiments, aryl groups contain one aromatic or heteroaromatic six-member ring and one or more additional five- or six-member aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms.

As used herein, the terms "alkylene" and "alkylene group" are used synonymously and refer to a divalent group derived from an alkyl group as defined herein. The invention includes compounds having one or more alkylene groups. Alkylene groups in some compounds function as attaching and/or spacer groups. Compounds of the invention may have substituted and/or unsubstituted $C_1$-$C_{20}$ alkylene, $C_1$-$C_{10}$ alkylene and $C_1$-$C_5$ alkylene groups.

As used herein, the terms "cycloalkylene" and "cycloalkylene group" are used synonymously and refer to a divalent group derived from a cycloalkyl group as defined herein. The invention includes compounds having one or more cycloalkylene groups. Cycloalkyl groups in some compounds function as attaching and/or spacer groups. Compounds of the invention may have substituted and/or unsubstituted $C_3$-$C_{20}$ cycloalkylene, $C_3$-$C_{10}$ cycloalkylene and $C_3$-$C_5$ cycloalkylene groups.

As used herein, the terms "arylene" and "arylene group" are used synonymously and refer to a divalent group derived from an aryl group as defined herein. The invention includes compounds having one or more arylene groups. In some embodiments, an arylene is a divalent group derived from an aryl group by removal of hydrogen atoms from two intra-ring carbon atoms of an aromatic ring of the aryl group. Arylene groups in some compounds function as attaching and/or spacer groups. Arylene groups in some compounds function as chromophore, fluorophore, aromatic antenna, dye and/or imaging groups. Compounds of the invention include substituted and/or unsubstituted $C_3$-$C_{30}$ arylene, $C_3$-$C_{20}$ arylene, $C_3$-$C_{10}$ arylene and $C_1$-$C_5$ arylene groups.

As used herein, the terms "heteroarylene" and "heteroarylene group" are used synonymously and refer to a divalent group derived from a heteroaryl group as defined herein. The invention includes compounds having one or more heteroarylene groups. In some embodiments, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as attaching and/or spacer groups. Heteroarylene groups in some compounds function as chromophore, aromatic antenna, fluorophore, dye and/or imaging groups. Compounds of the invention include substituted and/or unsubstituted $C_3$-$C_{30}$ heteroarylene, $C_3$-$C_{20}$ heteroarylene, $C_1$-$C_{10}$ heteroarylene and $C_3$-$C_5$ heteroarylene groups.

As used herein, the terms "alkenylene" and "alkenylene group" are used synonymously and refer to a divalent group derived from an alkenyl group as defined herein. The invention includes compounds having one or more alkenylene groups. Alkenylene groups in some compounds function as attaching and/or spacer groups. Compounds of the invention include substituted and/or unsubstituted $C_2$-$C_{20}$ alkenylene, $C_2$-$C_{10}$ alkenylene and $C_2$-$C_5$ alkenylene groups.

As used herein, the terms "cycloalkenylene" and "cycloalkenylene group" are used synonymously and refer to a divalent group derived from a cycloalkenyl group as defined herein. The invention includes compounds having one or more cycloalkenylene groups. Cycloalkenylene groups in some compounds function as attaching and/or spacer groups. Compounds of the invention include substituted and/or unsubstituted $C_3$-$C_{20}$ cycloalkenylene, $C_3$-$C_{10}$ cycloalkenylene and $C_3$-$C_5$ cycloalkenylene groups.

As used herein, the terms "alkynylene" and "alkynylene group" are used synonymously and refer to a divalent group derived from an alkynyl group as defined herein. The invention includes compounds having one or more alkynylene groups. Alkynylene groups in some compounds function as attaching and/or spacer groups. Compounds of the invention include substituted and/or unsubstituted $C_2$-$C_{20}$ alkynylene, $C_2$-$C_{10}$ alkynylene and $C_2$-$C_5$ alkynylene groups.

As used herein, the term "halo" refers to a halogen group such as a fluoro (—F), chloro (—Cl), bromo (—Br), iodo (—I) or astato (—At).

The term "heterocyclic" refers to ring structures containing at least one other kind of atom, in addition to carbon, in the ring. Examples of such heteroatoms include nitrogen, oxygen and sulfur. Heterocyclic rings include heterocyclic alicyclic rings and heterocyclic aromatic rings. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and functional groups, for example, provided as substituents.

The term "carbocyclic" refers to ring structures containing only carbon atoms in the ring. Carbon atoms of carbocyclic rings can be bonded to a wide range of other atoms and functional groups, for example, provided as substituents.

The term "alicyclic ring" refers to a ring, or plurality of fused rings, that is not an aromatic ring. Alicyclic rings include both carbocyclic and heterocyclic rings.

The term "aromatic ring" refers to a ring, or a plurality of fused rings, that includes at least one aromatic ring group. The term aromatic ring includes aromatic rings comprising carbon, hydrogen and heteroatoms. Aromatic ring includes carbocyclic and heterocyclic aromatic rings. Aromatic rings are components of aryl groups.

The term "fused ring" or "fused ring structure" refers to a plurality of alicyclic and/or aromatic rings provided in a fused ring configuration, such as fused rings that share at least two intra ring carbon atoms and/or heteroatoms.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)n-alkoxy wherein n is an integer from 1 to 10, preferably 1 to 4, and more preferably for some embodiments 1 to 3.

Amino acids include glycine, alanine, valine, leucine, isoleucine, methionine, proline, phenylalanine, tryptophan, asparagine, glutamine, glycine, serine, threonine, serine, asparagine, glutamine, tyrosine, cysteine, lysine, arginine, histidine, aspartic acid, glutamic acid, selenocysteine and pyrrolysine. As used herein, reference to "a side chain residue of a natural α-amino acid" specifically includes the side chains of the above-referenced amino acids.

As to any of the groups described herein that contain one or more substituents, it is understood that such groups do not contain any substitution or substitution patterns which are sterically impractical and/or synthetically non-feasible. In addition, the compounds of this invention include all stereochemical isomers arising from the substitution of these compounds. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl and aryl group includes substitution with one or more of the following substituents, among others:

halogen, including fluorine, chlorine, bromine or iodine; pseudohalides, including —CN;

—COOR, where R is a hydrogen or an alkyl group or an aryl group and more specifically where R is a methyl, ethyl, propyl, butyl, or phenyl group all of which groups are optionally substituted;

—COR, where R is a hydrogen or an alkyl group or an aryl group and more specifically where R is a methyl, ethyl, propyl, butyl, or phenyl group all of which groups are optionally substituted;

—CON(R)$_2$, where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—OCON(R)$_2$, where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—N(R)$_2$, where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring that can contain one or more double bonds and can contain one or more additional carbon atoms;

—SR, where R is hydrogen or an alkyl group or an aryl group and more specifically where R is hydrogen, methyl, ethyl, propyl, butyl, or a phenyl group, which are optionally substituted;

—SO$_2$R, or —SOR, where R is an alkyl group or an aryl group and more specifically where R is a methyl, ethyl, propyl, butyl, or phenyl group, all of which are optionally substituted;

—OCOOR, where R is an alkyl group or an aryl group;

—SO$_2$N(R)$_2$, where each R, independently of each other R, is a hydrogen, or an alkyl group, or an aryl group all of which are optionally substituted and wherein R and R can form a ring that can contain one or more double bonds and can contain one or more additional carbon atoms;

—OR, where R is H, an alkyl group, an aryl group, or an acyl group all of which are optionally substituted. In a particular example R can be an acyl yielding —OCOR", wherein R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

As to any of the above groups that contain one or more substituents, it is understood that such groups do not contain any substitution or substitution patterns which are sterically impractical and/or synthetically non-feasible. In addition, the compounds of this invention include all stereochemical isomers arising from the substitution of these compounds.

The compounds of this invention can contain one or more chiral centers. Accordingly, this invention is intended to include racemic mixtures, diasteromers, enantiomers, tautomers and mixtures enriched in one or more stereoisomer. The scope of the invention as described and claimed encompasses the racemic forms of the compounds as well as the individual enantiomers and non-racemic mixtures thereof.

DETAILED DESCRIPTION OF THE INVENTION

In general, the terms and phrases used herein have their art-recognized meaning, which can be found by reference to standard texts, journal references and contexts known to those skilled in the art. The following definitions are provided to clarify their specific use in the context of the invention.

Oxidation generally refers to a process involving the loss of one or more electrons or an increase in the oxidation state of an atom or group of atoms in a molecule or ion. Oxidation may refer to an oxidation half reaction in an oxidation—reduction reaction (i.e., Redox reaction). Oxidation may involve reaction of a reactant undergoing oxidation with an oxidizing agent, thereby resulting in an oxidation product having one or more atoms characterized by a higher oxidation state as compared to the reactant undergoing oxidation. In some embodiments, for example, oxidation results in the formation of an oxygen-containing product, such as in the oxidation of a hydrocarbon to yield an alcohol, ketone or diol.

"Oxidation product" refers to a reaction product of an oxidation reaction. An oxidation product may be characterized by one or more atoms having a higher oxidation state as compared to that of a reactant undergoing oxidation. For example, a hydrocarbon substrate such as methane ($CH_4$) can be oxidized to form the oxidation product methanol ($CH_3OH$).

"Copper complex" refers to a composition comprising one or more copper atoms or ions bound to one or more ligands. In some embodiments, copper complex refers to a coordination complex comprising copper ions surround by one or more ligand. The invention includes tricopper complexes comprising three Cu ions bound to or otherwise associated with one or more ligand (L).

"Catalyst" refers to a composition that increases the rate of one or more chemical reactions of one or more reactants and is not consumed in the chemical reaction. In some embodiment, for example, a catalyst lowers the activation energy of a chemical reaction, thereby requiring less energy to achieve the transition state. Catalysts may participate in multiple chemical transformations in a reaction sequence, thereby increasing the rate of on overall transformation of reactants to products. In some embodiments, the invention provides catalysts for oxidation of a hydrocarbon, for example, copper catalysts comprising a tricopper complex.

"Partially oxidized tricopper complex reaction product" refers to tricopper complex that is not fully oxidized and is formed as a reaction product, for example, formed as a product of a reaction of an oxygenated activated copper catalyst and a hydrocarbon. In an embodiment, for example, a partially oxidized tricopper complex reaction product is characterized by one or more atoms having a lower oxidation state than that of an oxygenated activated copper catalyst.

This invention is further explained with the following embodiments, which are not intended to limit the scope of this invention.

Structure of Molecular Catalyst

The present invention provides copper catalysts comprising tricopper complexes useful for the oxidation of hydrocarbons.

In an embodiment, the tricopper complex in the molecular catalyst of this invention may be expressed as "[$Cu^I Cu^I Cu^I$(L)]$^{1+}$", wherein "$Cu^I Cu^I Cu^I$" means the tricopper cluster and "L" means the ligand expressed by the above formula (1). The molecular catalyst may also include a counter ion, such as $ClO_4^-$ or $BF_4^-$.

In an embodiment, in the above formula (1) expressing the ligand, X, Y=N, $R^1$ and $R^2$ join together to form an ethylene group and form a 6-member ring (piperazine ring) with the ethylenediamine moiety bonded thereto, $R^{1\prime}$ and $R^{2\prime}$ also join together to form an ethylene group, $R^3$ and $R^{3\prime}$ are ethyl, and $R^4$, $R^{4\prime}$ and $R^5$ are hydrogen. Such ligand is called "7-N-Etppz" hereafter and expressed by formula (2):

(2)

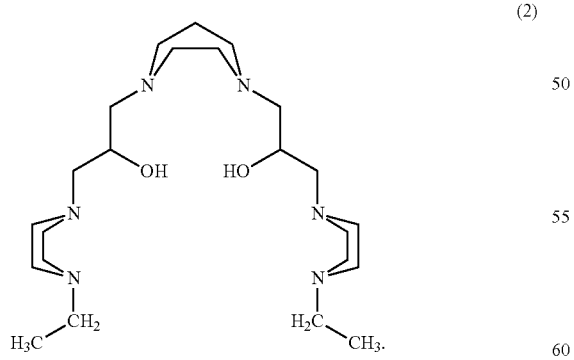

Many tricopper complexes have been constructed and evaluated as molecular catalysts for the oxidation of various hydrocarbons, including, but not limiting to, those based on the organic ligands depicted in Scheme 1.

Scheme 1

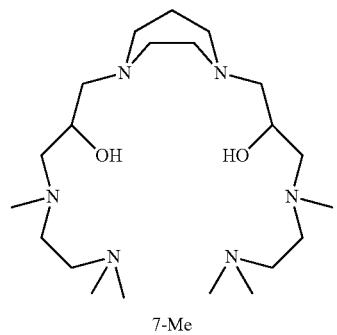

7-Me

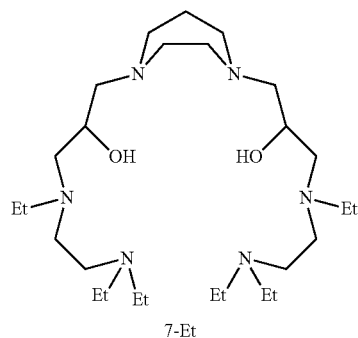

7-Et

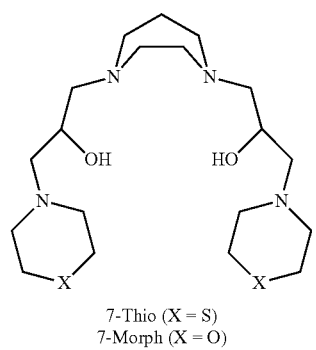

7-Thio (X = S)
7-Morph (X = O)

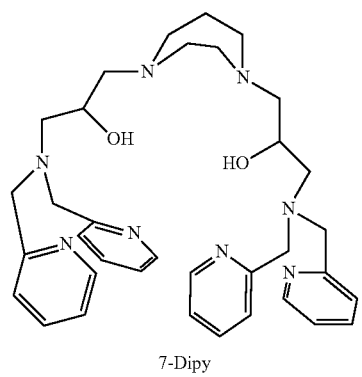

7-Dipy

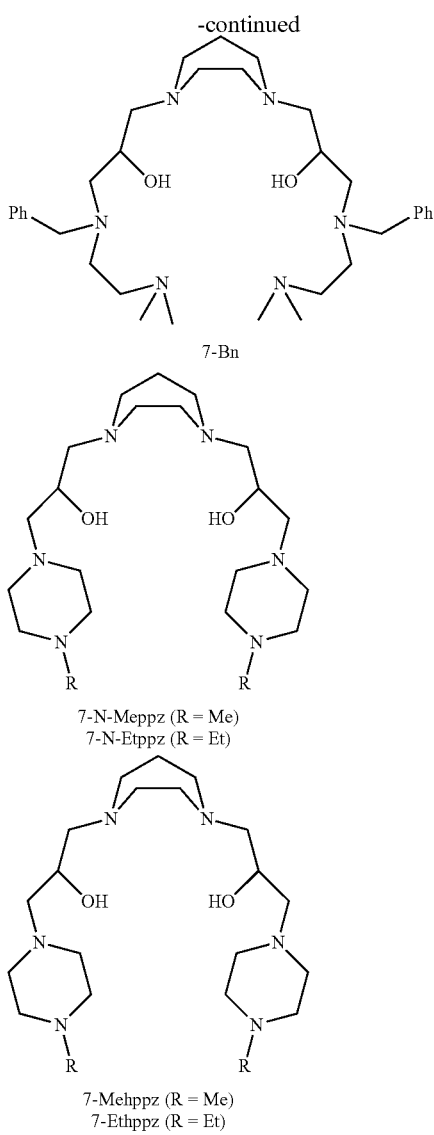

7-Bn

7-N-Meppz (R = Me)
7-N-Etppz (R = Et)

7-Mehppz (R = Me)
7-Ethppz (R = Et)

Method for Oxidizing Hydrocarbons with the Molecular Catalyst

In the method for oxidizing a hydrocarbon of the invention, the hydrocarbon and an oxidizing agent are made contact with the molecular catalyst to form at least one oxidation product of the hydrocarbon.

Examples of the oxidizing agent include dioxygen ($O_2$), air, and $H_2O_2$.

In a case where the hydrocarbon is in a gas state, it may be dissolved in a solvent containing the molecular catalyst to contact with the same, or be directly made contact with the molecular catalyst. Examples of such hydrocarbons include methane, ethane, propane, n-butane, and natural gas containing about 70-90% of methane and about 0-30% of ethane, propane and n-butane. In a case where the hydrocarbon is in a liquid state, it may be dissolved in a solvent containing the molecular catalyst to contact with the same, or be directly made contact with the molecular catalyst in the pure liquid state. Examples of such hydrocarbons include n-pentane, n-hexane, cyclohexane, and cyclohexene.

An example of the above solvent is acetonitrile (MeCN).

In an embodiment of the method of this invention, the hydrocarbons to be oxidized is added in an organic solvent containing the molecular catalyst (Method 1: homogeneous catalyst), or the molecular catalyst immobilized in MSNs (Method 2: heterogeneous catalyst), and air or $O_2$, or a liquid oxidizing agent, such as $H_2O_2$, is then, or simultaneously, added in the solution.

Catalysis Mechanism of Molecular Catalyst

In an embodiment, when the oxidizing agent is $O_2$, the tricopper cluster is firstly activated by $O_2$, as expressed by the following formula:

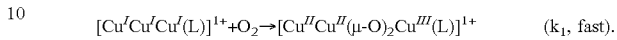

When the oxidizing agent is $H_2O_2$, the tricopper cluster is firstly activated by $H_2O_2$, as expressed by the following formulae:

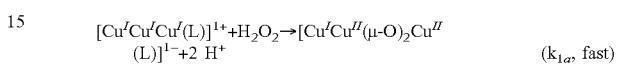

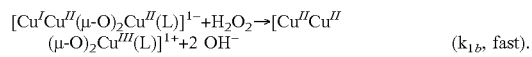

The intermediate $[Cu^{II}Cu^{II}(\mu\text{-}O)_2Cu^{III}(L)]^{1+}$ then reacts with the hydrocarbon to transfer one of the oxygen atoms into the latter, and the oxidation product may be further oxidized by the oxidizing agent through an additional catalytic cycle of the molecular catalyst.

When the oxidizing agent is $H_2O_2$, the above reactions may be expressed by Scheme 2, wherein the substrate A is oxidized to the oxo-substrate B, followed by rearrangement to give a product C or further direct oxidation by $H_2O_2$ to produce D.

Scheme 2

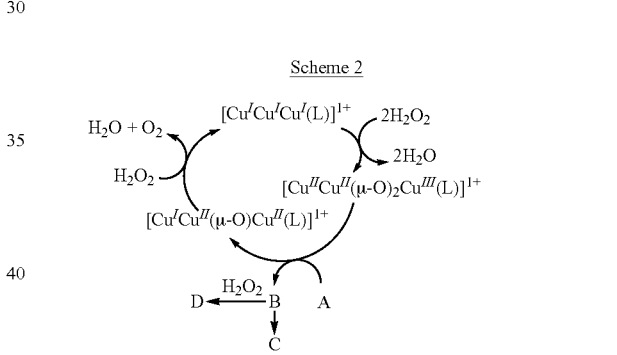

Some examples are provided below to further exemplify specific aspects of the present catalysts and catalytic methods, which are however not intended to restrict the scope of this invention.

EXAMPLE 1

Homogeneous Catalysis

This Example provides a description of exemplary homogeneous catalyst compositions, formulations and methods of the invention. The molecular catalyst used in this example is $[Cu^ICu^ICu^I(7\text{-N-Etppz})](ClO_4)$ according to the first embodiment of this invention.

In this example, 22.7 μmoles (I equiv.) of $[Cu^ICu^ICu^I(7\text{-N-Etppz})]^{1+}$ was used to catalyze the oxidation of various hydrocarbons by $H_2O_2$ in 3 ml of MeCN (or EtCN) in a 60 ml glass sample bottle at room temperature. The studied hydrocarbons included methane, ethane, propane, n-butane, n-pentane, n-hexane, cyclohexane and cyclohexene, wherein n-pentane, n-hexane, cyclohexane and cyclohexene were liquids. Although each of these liquid substrates was not miscible with MeCN in all proportions, it had sufficient solubility and the substrate oxidation could be initiated by adding appropriate amounts of the hydrocarbon to the solvent containing the tricopper catalyst followed by adding the desired amounts of $H_2O_2$, and the solution was mixed vigorously.

The data for these hydrocarbons were obtained with 11.3 mmoles (500 equiv.) of the hydrocarbon in each case, and the turnover was driven by 200 equiv. of $H_2O_2$ from a 33% aqueous solution in the experiment. In the case of methane, ethane, propane and n-butane, the glass sample bottle is first sealed tightly with a rubber cap and evacuated before one of these gas substrates (100 ml NTP or $4.17\times10^{-3}$ mole, about 200 equiv.) was injected into the solvent containing the tricopper catalyst using a gas syringe. Then, 2.27 mmoles of $H_2O_2$ (100 equiv.) from a 33% aqueous solution was injected using a separate syringe to initiate the oxidation of ethane, propane or n-butane. Again, the reactions were carried out with vigorous agitation of the solution.

In the case of methane, 0.39 mmoles (20 equiv.) of $H_2O_2$ was used and the $H_2O_2$ solution was added dropwise over 2 to 3 minutes. Given the limited solubility of these hydrocarbon gases in MeCN, the extent of hydrocarbon oxidation depends on the gas pressure in the overhead space (starting pressure 1.67 atm), as well as the amount of the gas dissolved in the solution. With the low solubility of methane in MeCN, only 20 equivalents of $H_2O_2$ were used in the initial experiments to mitigate abortive cycling of the catalyst. The amounts of $H_2O_2$ added have a dramatic effect on the turnover, which will be discussed later. The findings are summarized in FIG. 1 and Table 1.

TABLE 1

Catalytic oxidation of various hydrocarbons by $H_2O_2$.

| Substrates | | | Products (equiv.) | | |
|---|---|---|---|---|---|
| (C—H bond energy, kcal/mol) | Substrate (moles) | $H_2O_2$ (equiv.)[a] | alkanol (A) | alkanone (B) | alkane diol (C) |
| Methane (104.5) | $4.17 \times 10^{-3}$ | 20 | 6.5 | — | — |
| Ethane (101.1) | $4.17 \times 10^{-3}$ | 100 | 11 | — | — |
| Propane (100.4) | $4.17 \times 10^{-3}$ | 100 | 18.2 | — | — |
| n-Butane (98.2) | $4.17 \times 10^{-3}$ | 100 | 6 | 4 | 4.4 |
| n-Pentane (98) | $1.13 \times 10^{-2}$ | 200 | 1.2 | 13.8 | — |
| n-Hexane (98) | $1.13 \times 10^{-2}$ | 200 | 5.2 | 18 | — |
| Cyclohexane (99.3) | $1.13 \times 10^{-2}$ | 200 | 26 | 17 | — |

| Substrate (C—H bond energy, kcal/mol) | | | alkanol (A) | alkanone (B) | epoxide (D) |
|---|---|---|---|---|---|
| Cyclohexene (83.9) | $1.13 \times 10^{-2}$ | 200 | 4.2 | 21 | 18 |

[a]1 equiv. of catalyst corresponds to 22.7 μmoles.

Only methanol, ethanol, and 2-propanol are produced in the catalytic oxidation of methane, ethane, and propane mediated by the tricopper cluster, respectively. There is no evidence for over-oxidation of these hydrocarbons to form their corresponding aldehydes or ketones. In the case of n-butane, however, the formation of 2-butanol, 2-butanone and 2,3-butanediol was observed. For n-pentane, the products were 2-pentanol and 2-pentanone, and for n-hexane, 2-hexanol and 2-hexanone, with preference for the ketone in both cases. With cyclohexane, cyclohexanol and cyclohexanone were formed in roughly equal proportions. For cyclohexene, the oxidation yielded the epoxide, cyclohexenol and cyclohexenone.

Cyclohexane is the benchmark substrate for the type of catalytic reactions under discussion here. The bond energy associated with the C—H bond is 99.5 kcal/mole. The oxidation of cyclohexane mediated by the $[Cu^{I}Cu^{I}Cu^{I}(7\text{-N-Etppz})]^{1+}$ complex with $H_2O_2$ as the O-atom source was extremely efficient. Under the conditions of those experiments, there was essentially no abortive cycling. A time-course study indicated that practically all the $H_2O_2$ used to turn over the catalyst for substrate oxidation is consumed within 30 min, as described in FIGS. 2 and 3.

As with cyclohexane and cyclohexene, some over-oxidation was observed for n-butane, n-pentane and n-hexane. The most likely explanation is that the smaller alcohols did not have sufficient binding affinity for the "active-site" pocket and were released as soon as the product was formed. This was apparently not the case with the alcohols formed with the other hydrocarbons. For example, in the case of n-butane, the 2-butanol evidently resided in the active site long enough for another round of oxidation to produce 2-butanone and 2,3-butanediol. Since 2-butanol by itself was not a good substrate of the tricopper complex for conversion to 2-butanone or 2,3-butanediol, the over-oxidation was evidently kinetically controlled.

Surprisingly, with n-pentane, n-hexane and cyclohexane, the alcohol is only further oxidized to give the ketone but a diol was not formed. This result suggests that the details of the interaction between the molecular binding surfaces of the tricopper complex and the substrate are important for the regio-specificity of the oxidation. For the longer alkanes, cyclohexane and cyclohexene, van der Waals interactions between the aliphatic parts of the substrate and the binding surface of the activating tricopper complex may dictate the positioning and orientation of these hydrocarbon substrates in the binding pocket.

Figure 4:
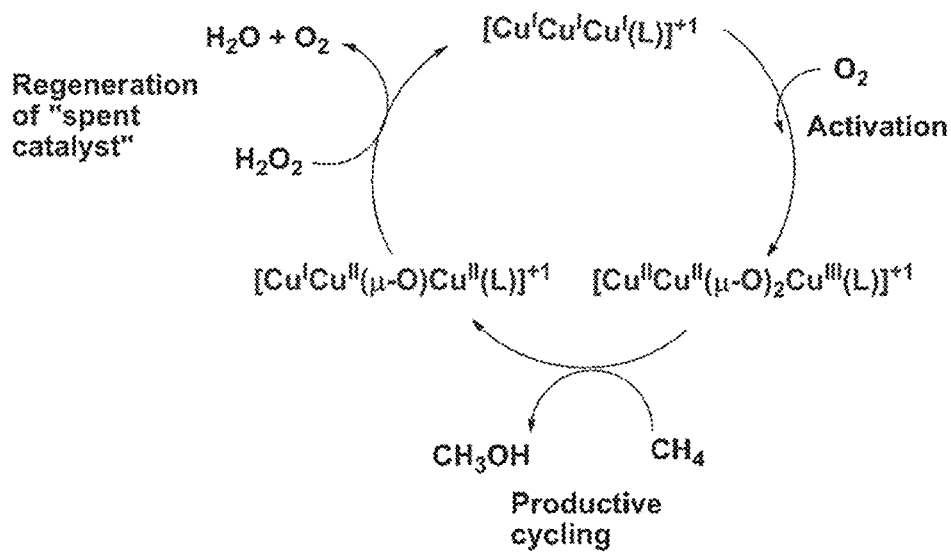
FIG. 4 compares productive cycling (A) and abortive cycling (B) in the oxidation of methane by O$_2$ mediated by the [Cu$^I$Cu$^I$Cu$^I$(7-N-Etppz)]$^{1+}$ complex in the presence of H$_2$O$_2$ as a "sacrificial" reductant to regenerate the molecular catalyst in Example 1 of this invention. [*Angew. Chem. Int. Ed.* 52, 3731-3735 (2013).]
Figure 4:
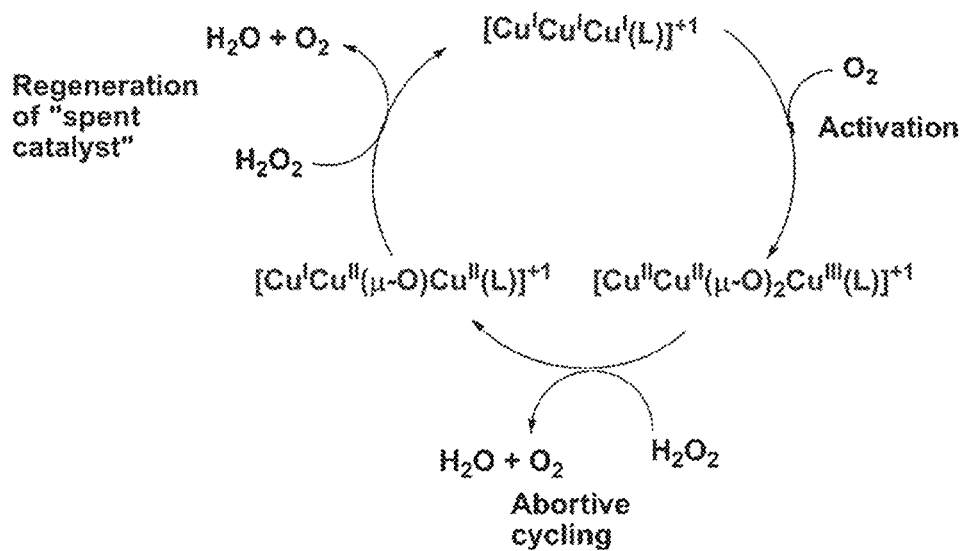

A measure of the effectiveness of the catalytic system for the oxidation of the various hydrocarbons examined in this study is given by the percentage of the $H_2O_2$ consumed by productive cycling for the amount of $H_2O_2$ used to drive the turnover. $H_2O_2$ is also a reductant, and can abort by reduction the $O_2$-activated $[Cu^{II}Cu^{II}(\mu\text{-}O)_2Cu^{III}(L)]^{1+}$ intermediate if the oxidizing equivalent stored in this intermediate is not transferred to the substrate sufficiently rapidly. FIG. 4 illustrates the difference between productive cycling (A) and abortive cycling (B) in the oxidation of methane by $O_2$ mediated by the $[Cu^{I}Cu^{I}Cu^{I}(7\text{-N-Etppz})]^{1+}$ complex in the presence of $H_2O_2$ used as a "sacrificial" reductant to regenerate the molecular catalyst in Example 1 of this invention.

The number of productive turnovers as a fraction of the total turnover of the catalyst including both productive and abortive cycles is listed in Table 2. Three $H_2O_2$ molecules are consumed per productive cycle, and four for an abortive cycle. In this analysis, it had been assumed that the total amount of $H_2O_2$ introduced into the medium to drive the substrate oxidation had been exhausted during the 1 h experiment, a good approximation when 200 equiv. of $H_2O_2$ were used. In any case, according to this indicator, the tricopper complex $[Cu^{I}Cu^{I}Cu^{I}(7\text{-N-Etppz})]^{1+}$ is indeed an efficient catalyst for the oxidation of hydrocarbons at room temperature.

TABLE 2

Efficiency of the catalyst for different substrates.[a]

| Substrate | Catalytic turnovers (A + 2B + 2C) | Abortive cycles | Catalytic Efficiency (%) |
|---|---|---|---|
| Methane | 6.5 | 0.125 | 98 |
| Ethane | 11 | 16.75 | 40 |
| Propane | 18.2 | 11.35 | 62 |
| n-Butane | 22.8 | 7.9 | 74 |
| n-Pentane | 28.8 | 28.4 | 50 |
| n-Hexane | 41.2 | 19.1 | 68 |
| Cyclohexane | 60 | 5 | 92 |

| Substrate | Catalytic turnovers (A + 2B + D) | | |
|---|---|---|---|
| Cyclohexene | 64.2 | 1.85 | 97 |

[a]Catalytic efficiency denotes the effectiveness of the $[Cu^{I}Cu^{I}Cu^{I}(7\text{-N-Etppz})]^{1+}$ complex as a catalyst for hydrocarbon oxidation based on the amount of $H_2O_2$ used to drive the turnover. It is given by the ratio of the productive turnovers of the catalyst to the total number of turnovers of the catalyst including both productive and futile cycles during the course of the 1-hour experiment.

Figure 2:
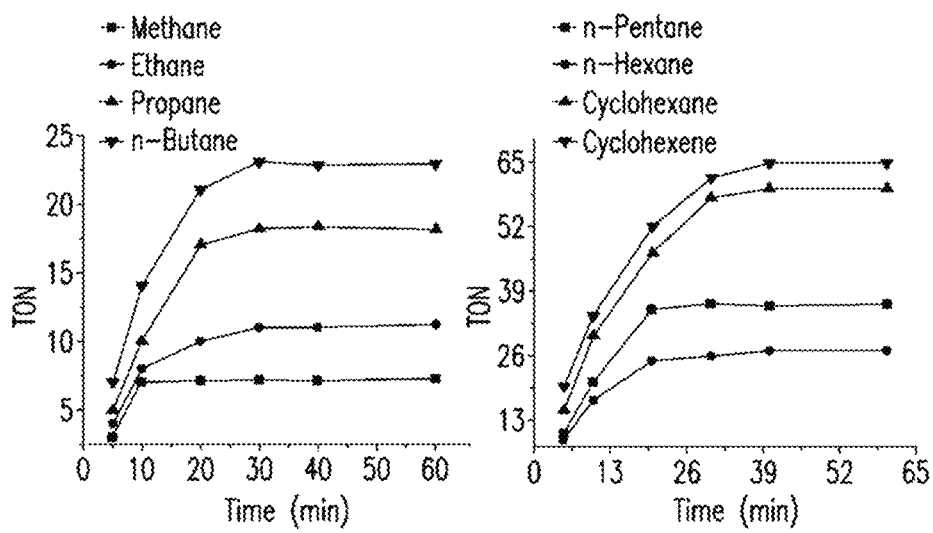
FIG. 2 shows the time courses of the oxidation of various hydrocarbon substrates by H$_2$O$_2$ mediated by the [Cu$^I$Cu$^I$Cu$^I$(7-N-Etppz)]$^{1+}$ complex in Example 1 of this invention. [*Catal. Sci. Technol.*, 4, 930-935 (2014).]

The time courses of the oxidation of the various hydrocarbons are shown in FIG. 2, where the equivalents of the oxo-products produced at various times up to one hour are plotted, weighted according to the number of oxidizing equivalents transferred (TON). These data reveal that the oxidation was indeed very rapid for all the hydrocarbons studied. In every case, the $H_2O_2$ used to drive the turnover was almost exhausted in less than 20 min, well before the completion of the one-hour study. This was true even in the case of methane. In the methane oxidation experiments described earlier, only 20 equiv. of $H_2O_2$ was used to drive the turnover. Of course, with the lower amount of $H_2O_2$ employed to drive the oxidation, the TON was low. It also slowed down the turnover of the tricopper catalyst, but more importantly, the lower $H_2O_2$ concentration mitigates abortion of the activated catalyst, keeping more of the $H_2O_2$ for productive oxidative turnover, as evidenced by high fraction of the $H_2O_2$ that was consumed by productive cycling of the catalyst (catalytic efficiency 98%) (see Table 2). As expected, when a greater amount of $H_2O_2$ was used to oxidize methane, the TON diminished abruptly. With 40 equiv. of $H_2O_2$, the catalytic efficiency was only 30%, and with 80 equiv., only a meager 6% of the turnover of the catalyst results in the formation of methanol.

In the case of methane, the factor limiting the turnover was the low solubility of the gas in MeCN. Of the four gases studied, methane has the lowest solubility in MeCN. Higher amounts of $H_2O_2$ can be used if the concentration of $CH_4$ in the solution was higher to speed up the second-order O-atom transfer reaction mediated by the catalyst. Although there was an excess of $CH_4$ in the system, the methane concentration was limited by the solubility of the gas in the solvent under the headspace gas pressure.

Figure 3:
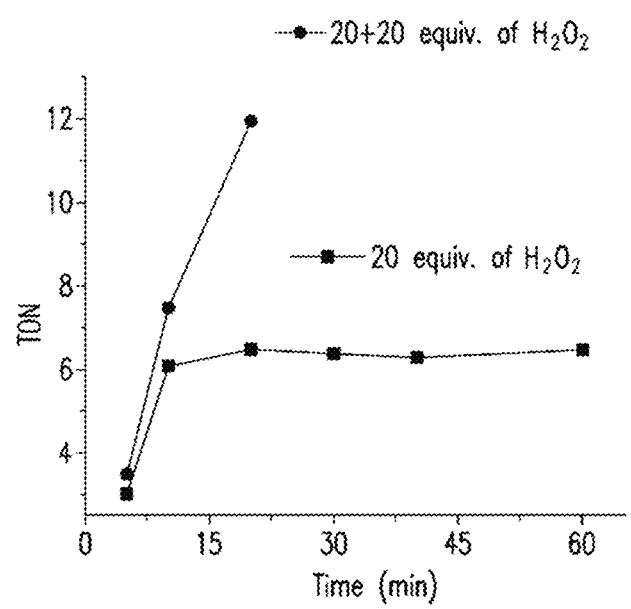
FIG. 3 shows the effect of the amount of H$_2$O$_2$ to the oxidation of methane mediated by the [Cu$^I$Cu$^I$Cu$^I$(7-N-Etppz)]$^{1+}$ complex in Example 1 of this invention.

The oxidation experiment was repeated with the volume of the solvent increased from 3 ml to 6 ml to ensure that the process was not limited by the availability of the hydrocarbon. The same amount of the tricopper catalyst was used and the same amount of $H_2O_2$ was used to drive the turnover. Thus, the concentration of the tricopper catalyst and the starting concentration of the $H_2O_2$ were a factor of 2 lower, but the $CH_4$ concentration remained the same. Accordingly, the turnover should be slower, but interestingly, the same TON was obtained at the end of the 1 h experiment. Thus, it was not the availability of $CH_4$ that limited the TON, rather the amount of $H_2O_2$ used to drive the process. To corroborate this conclusion, additional 20 equivalents of $H_2O_2$ were added after 8-10 min when it was apparent that the initial amount had already been consumed. As expected, the turnover of the catalyst quickly proceeded to yield additional product, the TON rapidly doubling to about 12 within another 15 min, as shown in FIG. 3. With incremental additions of the same amount of $H_2O_2$ at 15 min intervals, the TON increased proportionally, but leveled off as the methane was consumed. These observations underscore the interplay between productive cycling and abortive cycling in the catalytic methane oxidation as well as the importance of matching the input and output operating conditions of the catalyst to attain optimal performance of the system.

In summary, the $[Cu^{I}Cu^{I}Cu^{I}(7\text{-N-Etppz})]^{1+}$ catalyst system used in this example promoted efficient oxidation of hydrocarbons with $H_2O_2$ as the oxidant in MeCN at room temperature. The turnover frequency (TOF) of the catalyst was typically ca. $1 \times 10^{-2}$ s$^{-1}$ at a $H_2O_2$ concentration of 200 equiv. The oxidation is regio-specific, and the turnover number is only limited by the amount of $H_2O_2$ used to drive the process.

EXAMPLE 2

Heterogeneous Catalysis

This Example provides a description of exemplary heterogeneous catalyst compositions, formulations and methods of the invention. Two molecular catalysts are used in this example: the $[Cu^{I}Cu^{I}Cu^{I}(7\text{-N-Etppz})](ClO_4)$ complex described in the first embodiment of this invention, as well as $[Cu^{I}Cu^{I}Cu^{I}(7\text{-Ethppz})](ClO_4)$, a tricopper complex constructed from the ligand 7-Ethppz depicted in Scheme 1. The ligand 7-Ethppz differs slightly from 7-N-Etppz by the replacement of the 6-member piperazine ring by the 7-member homopiperazine ring.

Figure 5:
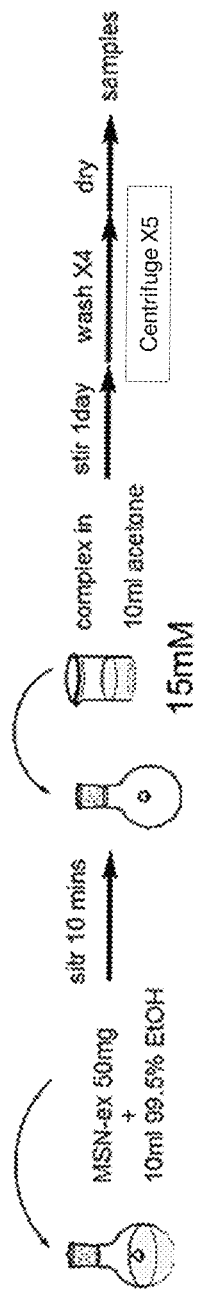
FIG. 5 shows the procedure for immobilization of the [Cu$^{II}$Cu$^{II}$Cu$^{II}$(7-N-Etppz)]$^{4+}$ complex, the [Cu$^{II}$Cu$^{II}$(μ$_3$-O)(Cu$^{II}$]7-N-Etppz)]$^{2+}$ complex, the [Cu$^{II}$Cu$^{II}$Cu$^{II}$(7-Ehppz)]$^{4+}$ complex, or the [Cu$^{II}$Cu$^{II}$(μ-O)(Cu$^{II}$]7-Ehppz)]$^{2+}$ complex in mesoporous silicate nanoparticles (MSN) of 5 nm pore size with high amounts of adsorption to be used as a heterogeneous catalyst for methane oxidation under ambient conditions in Example 2 of this invention.
Figure 5:
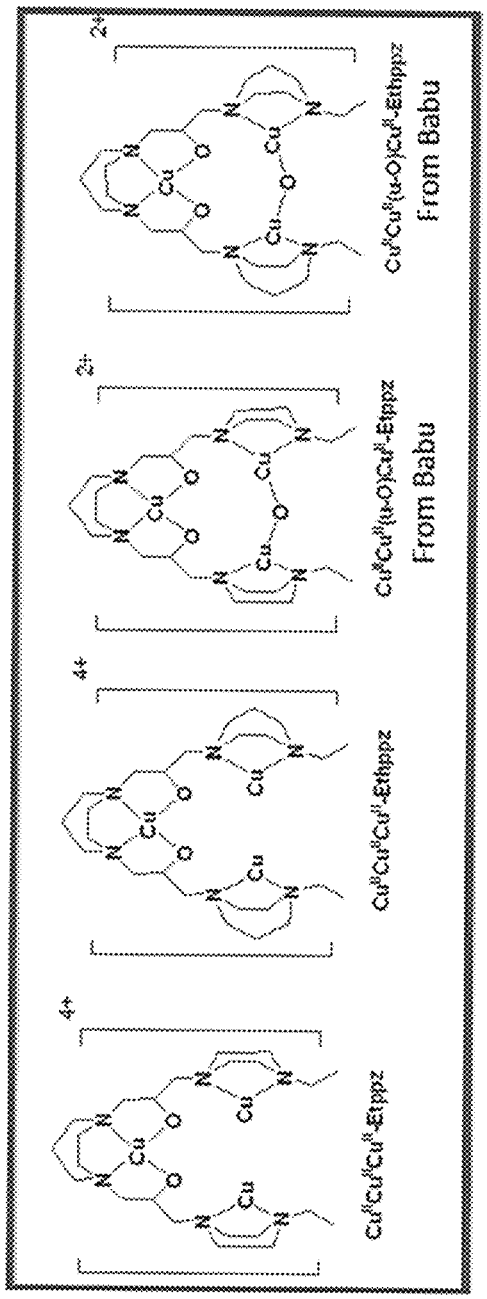

These two tricopper complexes have been formulated as heterogeneous catalysts for hydrocarbon oxidation by immobilization in mesoporous silicate nanoparticles (MSNs) as shown in FIG. 5. To prepare the heterogeneous catalyst, 50 mg of MSNs (pore size 5 nm) was first added to 10 ml of 99.5 ethanol (EtOH) and stirred for 10 min. A 15 mM solution of the tricopper complex in 10 ml acetone was then added to the MSNs, stirred for 1 day, centrifuged, washed and centrifuged for four additional times.

Figure 6:
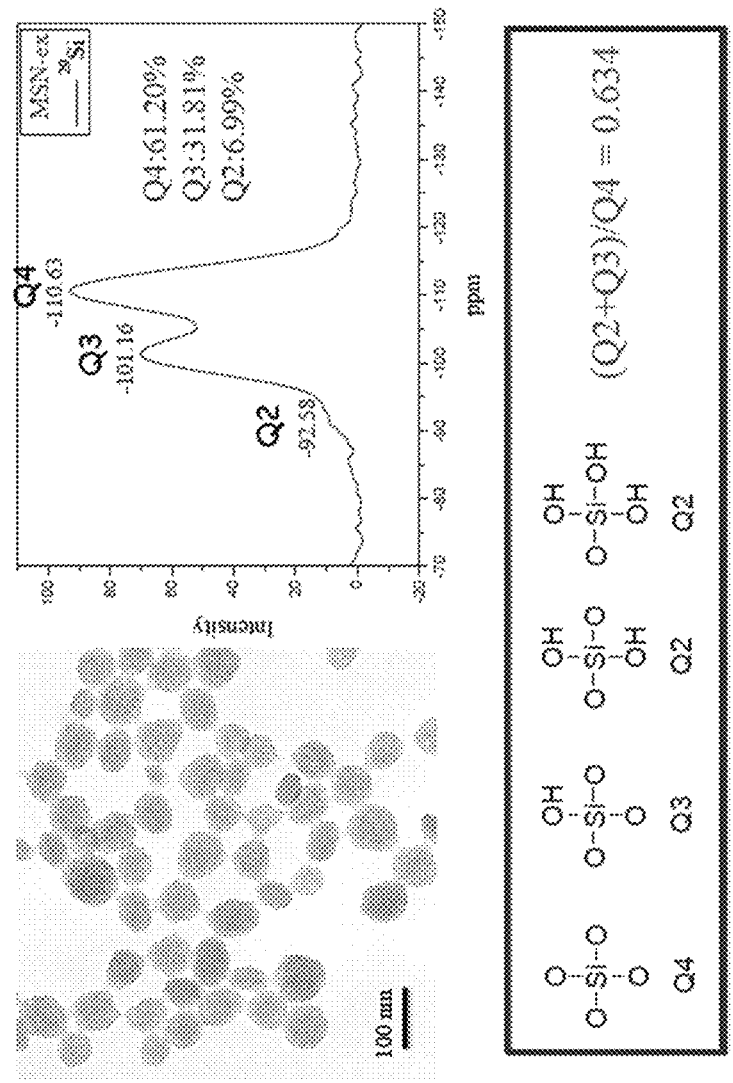
FIG. 6 shows the characterization of the MSN-ex material (pore size 5 nm) used to immobilize the tricopper complexes by transmission electron microscopy and solid-state $^{29}$Si nuclear magnetic resonance spectroscopy in Example 2 of this invention.

The MSN material used to immobilize the tricopper complexes has been characterized by transmission electron microscopy (TEM) and solid-state $^{29}$Si nuclear magnetic resonance spectroscopy (NMR), as shown in FIG. 6. The distribution of silicate environments in the MSNs is provided by the assignment of the various resonance peaks in the $^{29}$Si NMR.

As shown in Table 3, the tricopper complexes are tightly immobilized in the nanochannels of the negatively charged MSN samples with a negligible amount of leaching after 10 hours in MeCN at 25° C.

TABLE 3

Release of the immobilized $Cu^{II}Cu^{II}Cu^{II}$-complexes
from the MSN nanoparticles in MeCN at 25° C.[a]

| Sample Name Time (h) | Etppz@MSN-ex Release (‰) | Ethppz@MSN-ex Release (‰) | Etppz(μ-O)@MSN-ex Release (‰) | Ethppz(μ-O)@MSN-ex Release (‰) |
|---|---|---|---|---|
| 0 | 0 | 0 | 0 | 0 |
| 0.5 | 0.001 | 0.003 | 0.0005 | 0.004 |
| 1.0 | 0.003 | 0.006 | 0.002 | 0.007 |
| 2.0 | 0.008 | 0.011 | 0.005 | 0.012 |
| 4.0 | 0.010 | 0.014 | 0.007 | 0.015 |
| 6.0 | 0.011 | 0.018 | 0.009 | 0.020 |
| 8.0 | 0.014 | 0.021 | 0.012 | 0.024 |
| 10.0 | 0.016 | 0.024 | 0.014 | 0.029 |

[a]MSN-ex refers to silicate nanoparticles of 5 nm pore size.

Figure 7:
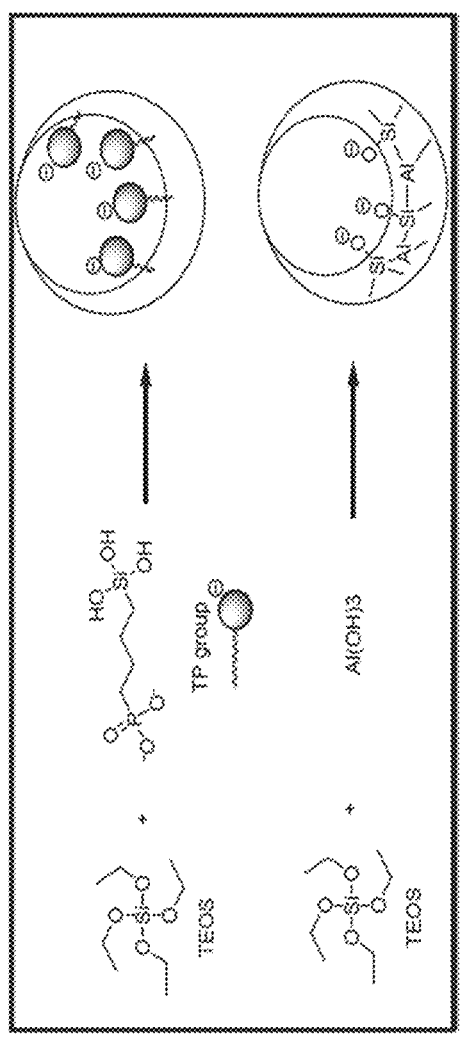
FIG. 7 shows functionalization of the MSNs with different surface acidities and charges with the anionic 3-trihydroxysilypropyl-methylphosphonate (TP) to generate a negatively charged surface, or by introducing Al into the framework, and TEM micrographs of the MSN-TP and the Al-MSN30-ex samples, respectively, in Example 2 of this invention.
Figure 7:
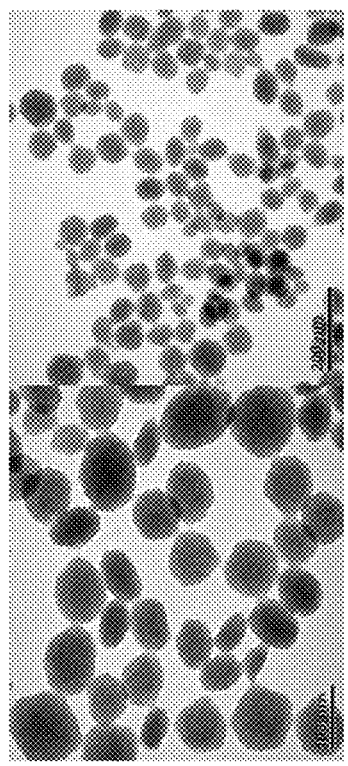

To optimize loading of the tricopper complexes in the immobilization of the molecular catalysts, the silicate nanoparticles have been functionalized by introducing the anionic 3-trihydroxysilypropyl-methylphosphonate (TP) to generate a negatively charged surface, or Al has been introduced into the framework, to facilitate the control of the surface acidities and charges of the MSNs. TEM micrographs of the MSN-TP and the Al-MSN30-ex samples are shown in FIG. 7.

The maximum adsorption of the tricopper complexes and zeta-potentials (ζ) of these functionalized MSN samples are presented in Table 4. These data indicate that the introduction of $Al^{3+}$ dramatically enhances the adsorption of the tricopper complexes and dramatically reduces the zeta-potential (ζ) of these MSNs.

TABLE 4

The maximum adsorption of tricopper complexes and
zeta potential (ζ) of the MSN samples.[a]

| Samples Name | Complex Adsorption (μmol/g) | zeta-potential (ζ) (mv) | Δζ (mv) |
|---|---|---|---|
| AlMSN30-ex | 0 | −46.1 | 0 |
| Cu-Etppz@AlMSN30-ex | 613 | −14.9 | +31.2 |
| Cu-Ethppz@AlMSN30-ex | 556 | −18.3 | +27.8 |
| MSN-TP | 0 | −36.2 | 0 |
| Cu-Etppz@MSN-TP | 345 | −22.6 | +13.6 |
| Cu-Ethppz@MSN-TP | 310 | −24.0 | +12.2 |

[a]The complex adsorption was determined by ICP-MS.

The Brunauer-Emmett-Teller (BET) surface area, pore volume, and pore diameter of the functionalized MSNs after immobilization of the tricopper complexes have also been determined, and these data are summarized in Table 5.

TABLE 5

BET surface area, pore volume, and pore diameter of
the MSNs after immobilization of the tricopper complexes
into the nanochannels of the nanoparticles.

| Sample Name | Surface Area (m²/g) | Pore Volume (cm³/g) | Pore Diameter (nm) |
|---|---|---|---|
| AlMSN30-ex | 1242.11 | 1.4344 | 4.8 |
| CU-Etppz@AlMSN30-ex | 758.9 | 0.9005 | 2.6 |
| CU-Ethppz@AlMSN30-ex | 803.9 | 0.9260 | 2.8 |
| MSN-TP | 912.4 | 0.7133 | 2.8 |

TABLE 5-continued

BET surface area, pore volume, and pore diameter of
the MSNs after immobilization of the tricopper complexes
into the nanochannels of the nanoparticles.

| Sample Name | Surface Area (m²/g) | Pore Volume (cm³/g) | Pore Diameter (nm) |
|---|---|---|---|
| CU-Etppz@MSN-TP | 701.9 | 0.3959 | 1.7 |
| CU-Ethppz@MSN-TP | 742.2 | 0.4131 | 1.8 |

Figure 8:
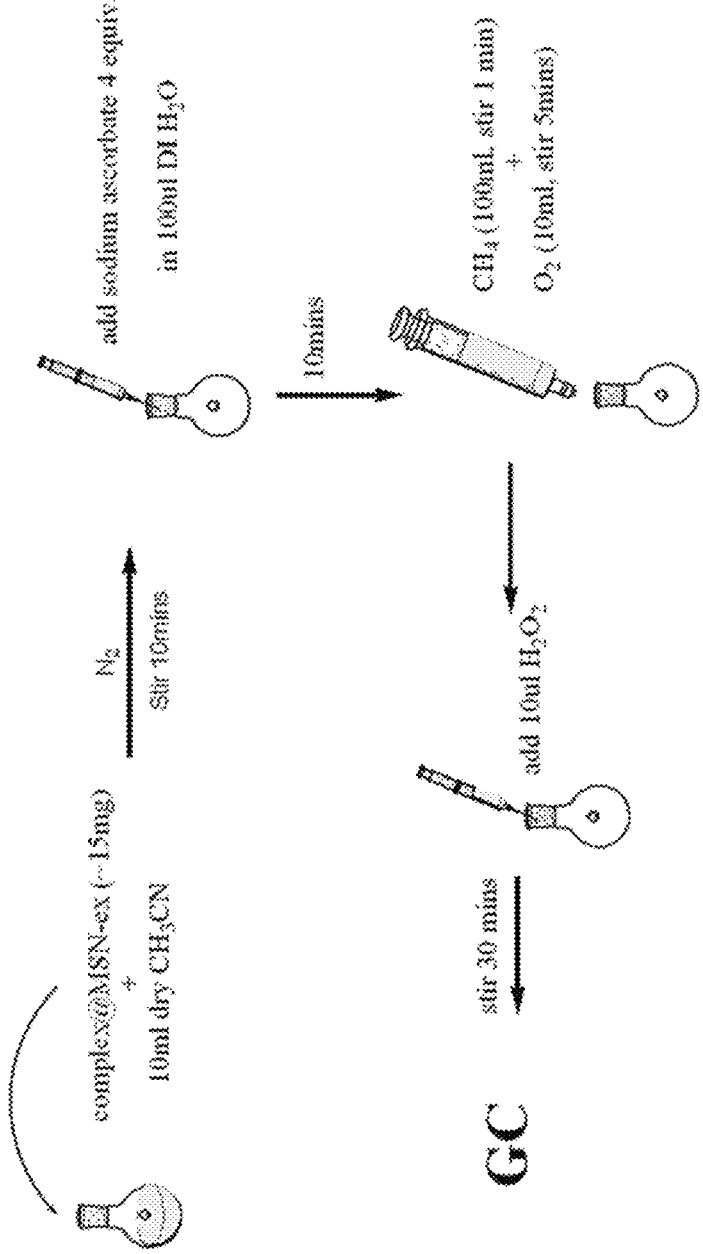
FIG. 8 shows the reaction procedure used to study the conversion of methane into methanol mediated by the fully reduced tricopper complexes immobilized in MSNs followed by activation by O$_2$ and turnover of the catalyst by H$_2$O$_2$ under ambient conditions in Example 2 of this invention.

FIG. 8 shows the reaction procedure used to study the conversion of methane into methanol mediated by the fully reduced tricopper complexes immobilized in the functionalized MSNs followed by activation by $O_2$ and turnover of the catalyst by $H_2O_2$ under ambient conditions in Example 2 of this invention.

Significantly higher turnover numbers of methane conversion into methanol have been achieved with the heterogeneous catalysts compared with the homogeneous catalyst studied in Example 1. Table 6 summarizes the turnover numbers of methane oxidation catalyzed by the tricopper complexes immobilized in different functionalized MSN samples using 100 and 200 equivalents of $H_2O_2$ to drive the turnover. With the molecular catalyst immobilized in the MSNs, the catalytic turnover is no longer limited by the availability of methane during the cycling of the catalyst. Methane is considerable more soluble in the mesoporous silicate nanoparticles relative to the typical solvent (e.g., MeCN) because of abundant mesopores and micropores in the MSNs that can accommodate the small methane gas molecules. Accordingly, abortive cycling is largely mitigated and the efficiency of the catalyst is significantly higher than in the case of the homogeneous catalyst described in Example 1.

TABLE 6

The turnover numbers of the methane oxidation reaction mediated
by the $[Cu^{I}Cu^{I}Cu^{I}(7\text{-N-Etppz})]^{1+}$ and $[Cu^{I}Cu^{I}Cu^{I}(7\text{-Ethppz})]^{1+}$
complexes immobilized in functionalized MSNs and the conversion of
the methane into methanol based on the amounts of methane introduced
into the reaction system for the experiments.

| | 100 eq. $H_2O_{2(aq)}$ | | 200 eq. $H_2O_{2(aq)}$ | |
|---|---|---|---|---|
| Sample Name | [a]TON | [b]Conversion | [a]TON | [b]Conversion |
| Cu-Etppz@AlMSN30-ex | 72.2 | 20.9 | 178.0 | 52.8 |
| Cu-Ethppz@AlMSN30-ex | 19.5 | 3.80 | 64.4 | 13.1 |

TABLE 6-continued

The turnover numbers of the methane oxidation reaction mediated by the [Cu$^I$Cu$^I$Cu$^I$(7-N-Etppz)]$^{1+}$ and [Cu$^I$Cu$^I$Cu$^I$(7-Ethppz)]$^{1+}$ complexes immobilized in functionalized MSNs and the conversion of the methane into methanol based on the amounts of methane introduced into the reaction system for the experiments.

| Sample Name | 100 eq. H$_2$O$_{2(aq)}$ | | 200 eq. H$_2$O$_{2(aq)}$ | |
|---|---|---|---|---|
| | $^a$TON | $^b$Conversion | $^a$TON | $^b$Conversion |
| Cu-Etppz@MSN-TP | 91.1 | 11.7 | 161.0 | 24.3 |
| Cu-Ethppz@MSN-TP | 15.4 | 1.73 | 59.1 | 6.82 |

$^a$TON = moles of methanol produced per mole of complex in catalyst.
$^b$Conversion = (mole of methanol produced per mole of methane injected) × 100%

Figure 9:
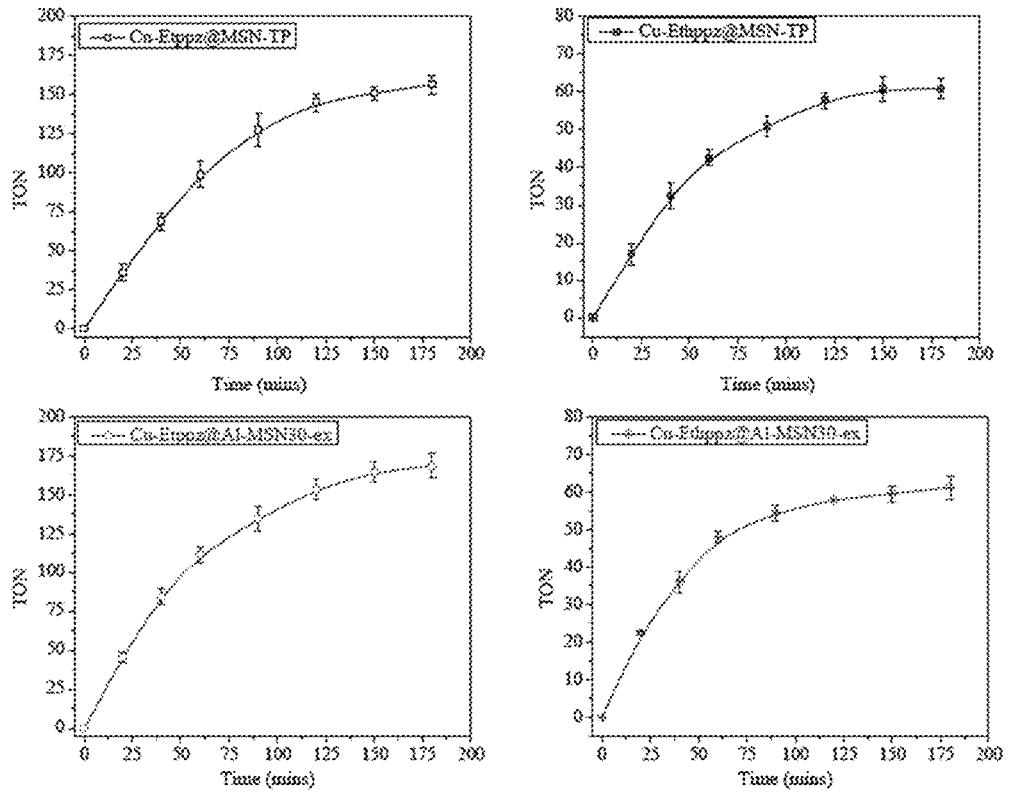
FIG. 9 shows the time course of the methane oxidation catalyzed by the various tricopper complexes immobilized in various functionalized MSN samples in Example 2 of this invention.

The time courses of the methane oxidation mediated by the two tricopper complexes formulated as heterogeneous catalysts in the MSNs are depicted in FIG. 9. Interestingly, for these tricopper catalysts, the turnover frequency in the heterogeneous system is similar to that in the homogeneous formulation. However the turnover number of the methane is dramatically higher because of the significant enhancement of the solubility of methane in the pores of the MSN silicate nanoparticles compared to the solubility of the gas in MeCN in the homogeneous solution.

Thus the heterogeneous catalyst is generally more efficient as a methane oxidizer, as well as for the oxidation of all components of the natural gas than the homogeneous catalyst described in Example 1. This system is also easier to handle and more readily adaptable for recovery of the product alcohols as well the catalyst for re-use.

EXAMPLE 3

Tricopper Catalysts: Structure and Function

This Example 3 illustrates biomimetic approaches for catalyst design based on the enzyme particulate methane monooygenase (pMMO) found in the methanotropic bacteria *Methylococcus capsulatus* (Bath).

The conversion of methane into methanol is one of the benchmark reactions in chemistry, but the process is a very difficult one because of the unusually high bond-energy of the C—H bond (105 kcal/mole). Accordingly, the C—H bond is very inert and this reaction has been one of holy grails of organic chemistry.

Microbes are capable of converting methane into methanol efficiently under ambient conditions. There happens to be two of these enzymes in methanotrophic bacteria: the soluble methane monooxygenase (sMMO) and the membrane-bound or particulate methane monooxygease (pMMO). The sMMO is a non-heme iron enzyme residing in the cytosol of these microbes, whereas the pMMO is membrane-bound and a copper enzyme that is expressed in these bacteria under high copper/biomass conditions. The pMMO enzyme found in *Methylococcus capsulatus* (Bath) has subsequently received a great deal of research attention as it is the most efficient methane oxidizer known, capable of converting methane to methanol at the rate approaching ~1 methane molecule oxidized per sec per enzyme molecule.

Figure 10:
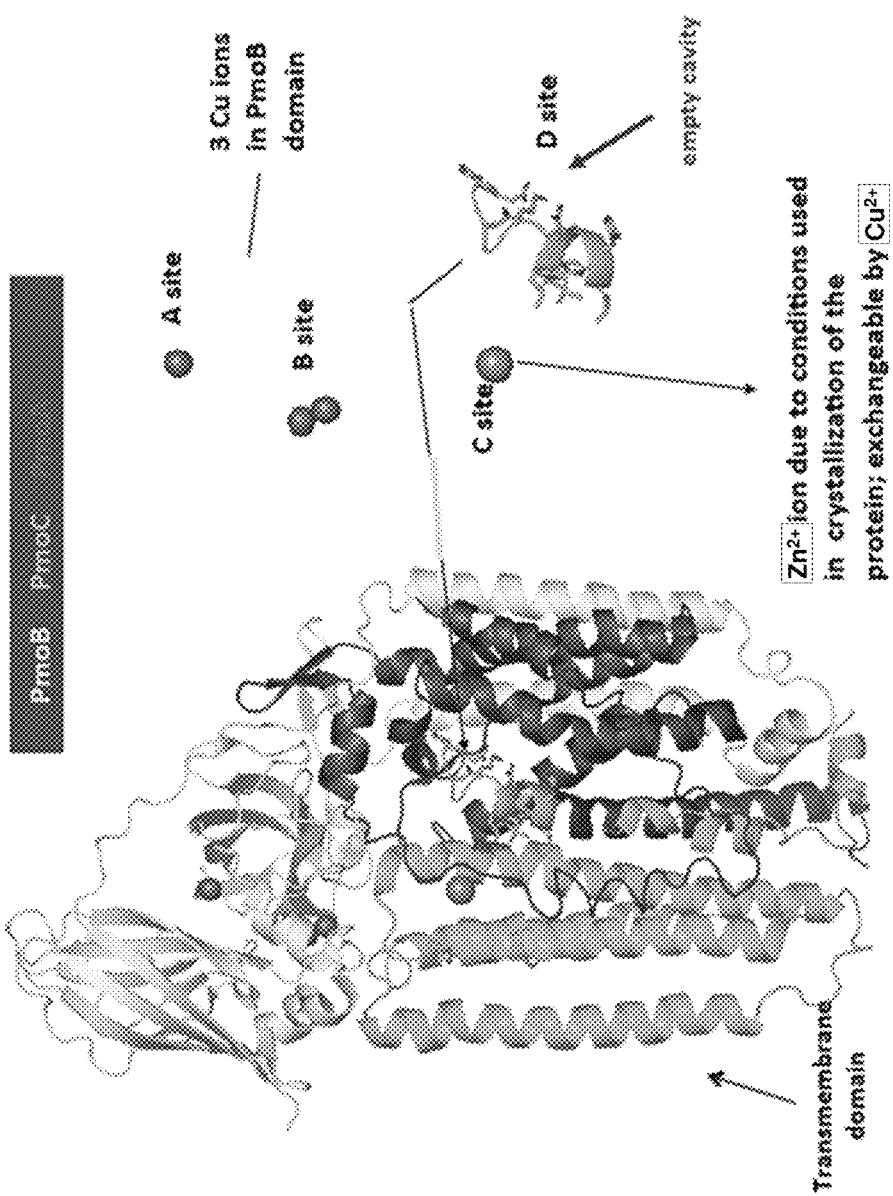
FIG. 10. The X-ray crystal structure of pMMO from *Methylococcus capsulatus* (Bath) reported by R. L. Lieberman, A. C. Rosenzweig in *Nature* 2005, 434, 177-182 and edited by S. I. Chan and S. S.-F. Yu in *Acc. Chem. Res.*, 41 (8), 969-979 (2008). Ribbon diagrams of the backbones of the three polypeptides PmoA, PmoB, and PmoC are shown, together with the mononuclear copper center (A site), the dicopper site (B site), the Zn site (C site) and the empty hydrophilic site (D site).

A major challenge facing researchers in understanding was growing sufficient quantities of the bacteria to allow the isolation of the pMMO from the membranes of the cells, purification of the protein to homogeneity, and biophysical/biochemical characterization of the protein reconstituted into detergent micelles, including possible crystallization of the protein for determination of the 3-D structure and the catalytic site and other metal cofactors. As a membrane metalloprotein, the enzyme is prone to losing cofactors as well as loss of structural integrity during the purification procedures making this process extremely difficult. In fact, when the x-ray crystal structure of the enzyme from *Methylococcus capsulatus* (Bath) appeared in 2005, it contained only 3 copper ions (FIG. 10), instead of the 12-15 copper cofactors. The protein preparation on which the X-ray structure was based was observed to be inactive. Purification of pMMO under reducing conditions is useful to ensure that the copper ions stayed Cu$^I$ during the protein isolation/purification procedures in order to mitigate the leaching of the copper ions from the protein during the transfer of the pMMO from the cell membranes into detergent as well as during purification by column chromatography [See, e.g., *J. Biol. Chem.* in 1998 [*J. Biol. Chem.*, 273 (14) 7957-7966 (1998)] and the other in the *J. Bacteriology* in 2003 [*J. Bacteriol.*, 185, 5915-5924 (2003).]

It is believed, that the pMMO is a Cu$^I$ enzyme that becomes partially oxidized when the membranes are isolated from the bacterial cells in the absence of methane under aerobic conditions. Spectroscopic characterization of the pMMO in these membranes by Cu K edge X-ray spectroscopy suggests that ~25% of the copper ions are Cu$^{II}$ and the remaining copper ions are Cu$^I$. Electron paramagnetic resonance spectroscopy (EPR) indicates that the four Cu$^{II}$ ions consisted of one type 2 Cu$^{II}$ center (square planar Cu$^{II}$) plus a tricopper site, in which the three Cu$^{II}$ ions are ferromagnetically coupled to form a quartet (S=3/2) ground state (that is, there is a ferromagnetic exchange interaction among the three Cu$^{II}$ ions to align the three unpaired electrons in the same direction in the ground state). This suggests that there is a tricopper cluster in the enzyme. [*Chem Cat Chem* 2014, 6, 429-437.]

Figure 11:
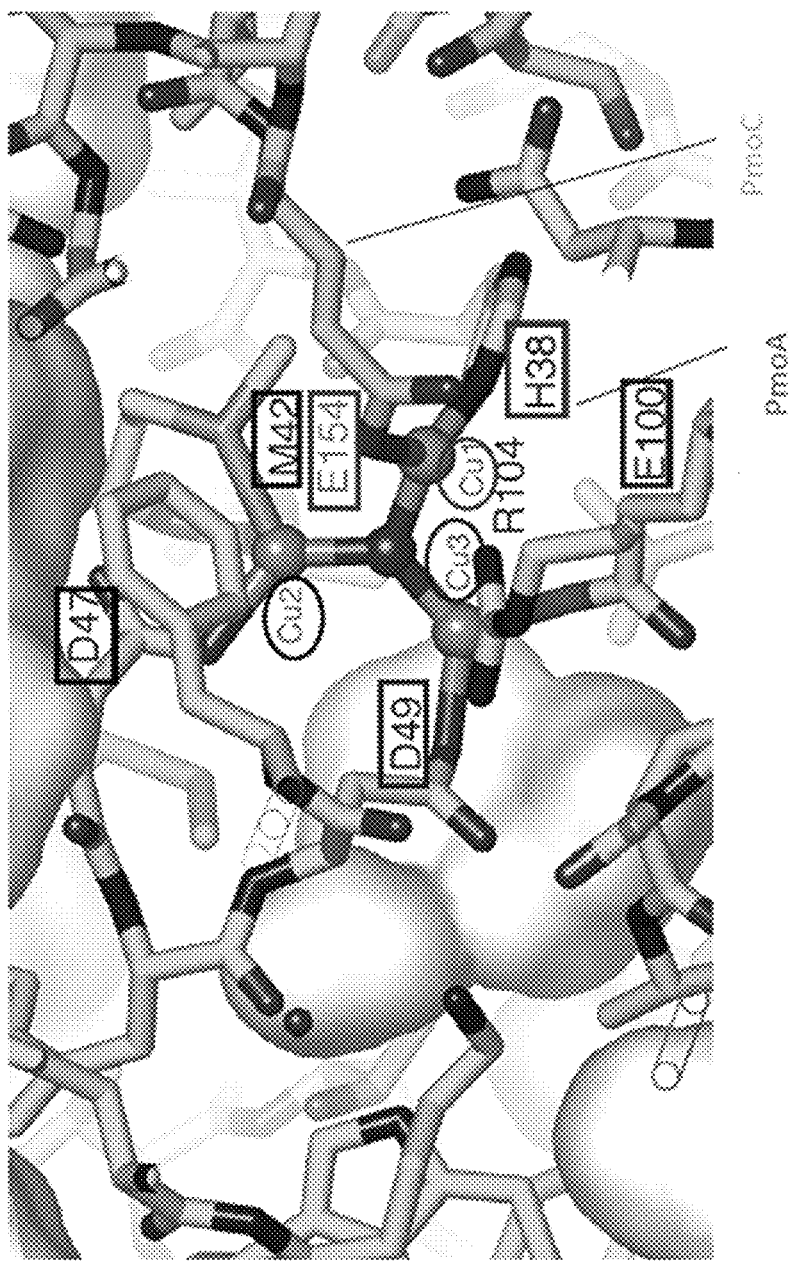
FIG. 11. The tricopper cluster modeled as a Cu$^{II}$Cu$^{II}$Cu$^{II}$ complex with a capping (μ$_3$-O) rebuilt into the site D of the X-ray crystal structure. The polypeptides are color-coded: PmoA, blue and PmoC, green, and the amino acid residues associated with the three Cu$^{II}$ ions are boxed: Cu1, red, Cu2, black, and Cu3, blue. [S. I. Chan, V. C.-C. Wang, J. C.-H. Lai, S. S.-F. Yu, P. P.-Y. Chen, K. H.-C. Chen, C.-L. Chen, M. K. Chan, *Angew. Chem.* 2007, 119, 2038-2040; *Angew. Chem. Int. Ed.* 2007, 46, 1992-1994.]

A tricopper cluster was not observed in the X-ray crystal structure, however. Soon after the X-ray structure of the protein appeared, it was noted that there was an empty pocket in the transmembrane domain with 1 histidine (H38 PmoA), 1 methionine (M42, PmoA), and 2 glutamates (Glu 100 PmoA and Glu 154 PmoC) and 2 aspartates (Asp 47 PmoA and Asp 49 PmoA), that might be ligands of a copper cluster. A model was created for a tricopper cluster into this site using these potential metal-binding residues (FIG. 11). Except for two glutamates (E100 PmoA and E154 PmoC), the ligands were part of a stretch of the alpha helix of the PmoA subunit embedded in the transmembrane domain. Subsequently, a peptide was synthesized based on the sequence of HIHAMLTMGDWD, the fragment containing the potential amino acids ligating the putative tricopper cluster at site D, and showed that it was capable of forming both the Cu$^I$Cu$^I$Cu$^I$ and Cu$^{II}$Cu$^{II}$Cu$^{II}$ 1:1 peptide tricopper complexes in the presence of acetate or chloride anions in the solution. [*Angew. Chem. Int. Ed.* 52, 3731-3735 (2013).] EPR measurements on the Cu$^{II}$Cu$^{II}$Cu$^{II}$ complex revealed the same EPR signal observed for the enzyme in the membranes as well as the purified protein reconstituted in detergent micelles. EXAFS measurements showed that the ligand structure of the Cu$^{II}$ ions was consistent with the structure built into the putative tricopper site in the X-ray structure. Significantly, the Cu$^I$Cu$^I$Cu$^I$ peptide complex could be activated by dioxygen to mediate oxidation of methane to methanol and epoxidation of propene to form propylene oxide.

Figure 12:
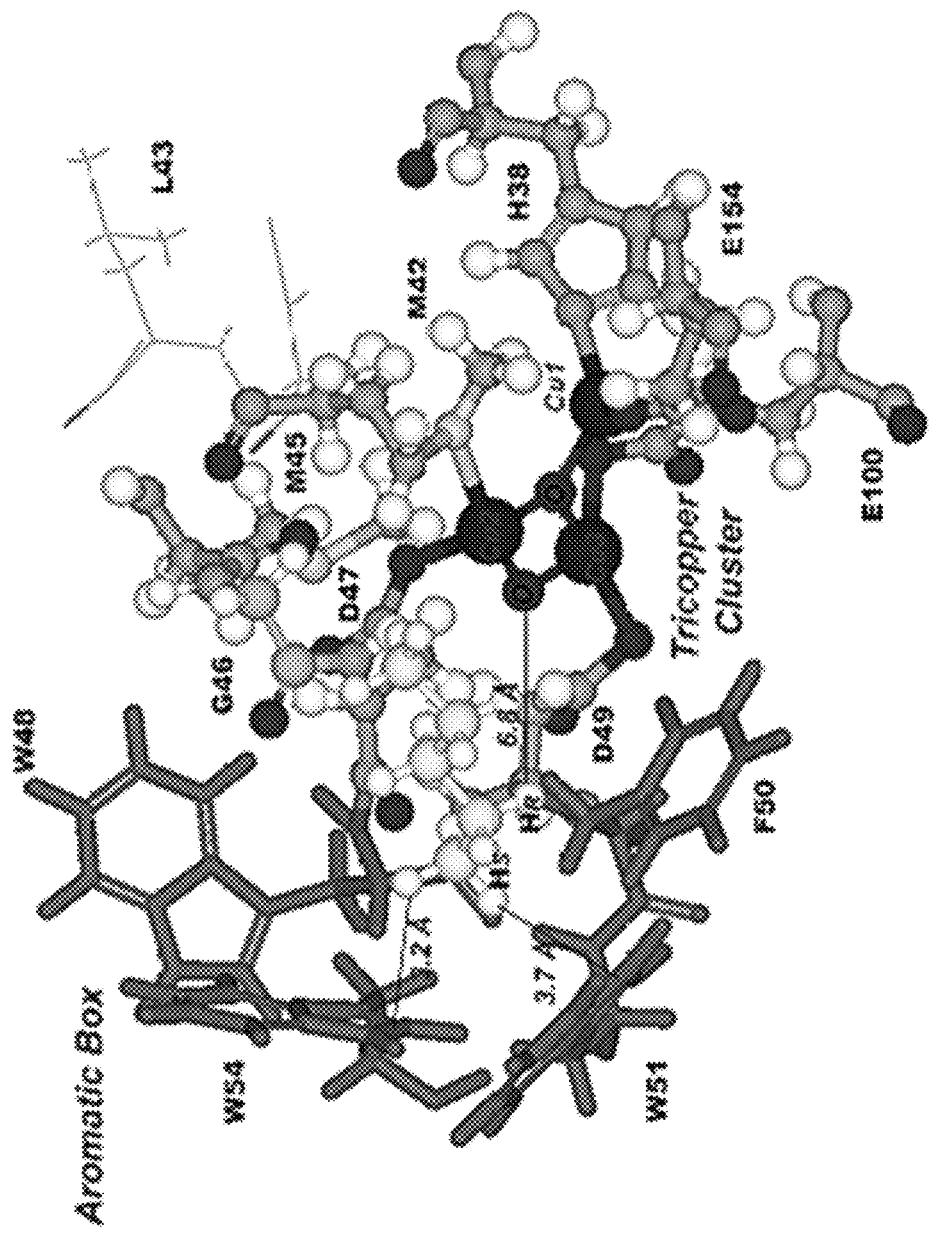
FIG. 12. The catalytic site of pMMO from *Methylococcus capsulatus* (Bath). [P. P.-Y. Chen, P. Nagababu, S. S.-F. Yu, S. I. Chan, *Chem Cat Chem* 2014, 6, 429-437.]

FIG. 12 depicts a zoom-in of the putative catalytic site of pMMO of *Methylococcus capsulatus* (Bath) based on efforts to rebuild the tricopper cluster at site D. Also shown is a pentane molecule (in yellow) occupying the hydrocarbon substrate binding site adjacent to (within a few Å) the tricopper cluster at site D. The substrate binding pocket is an "aromatic box", limited to the binding of n-alkanes up to 5 carbons only; n-pentane is the largest straight-chain alkane that is hydroxylated by the pMMO enzyme. [*Chembiochem,* 9, (7), 1116-1123 (2008).]

Figure 13:
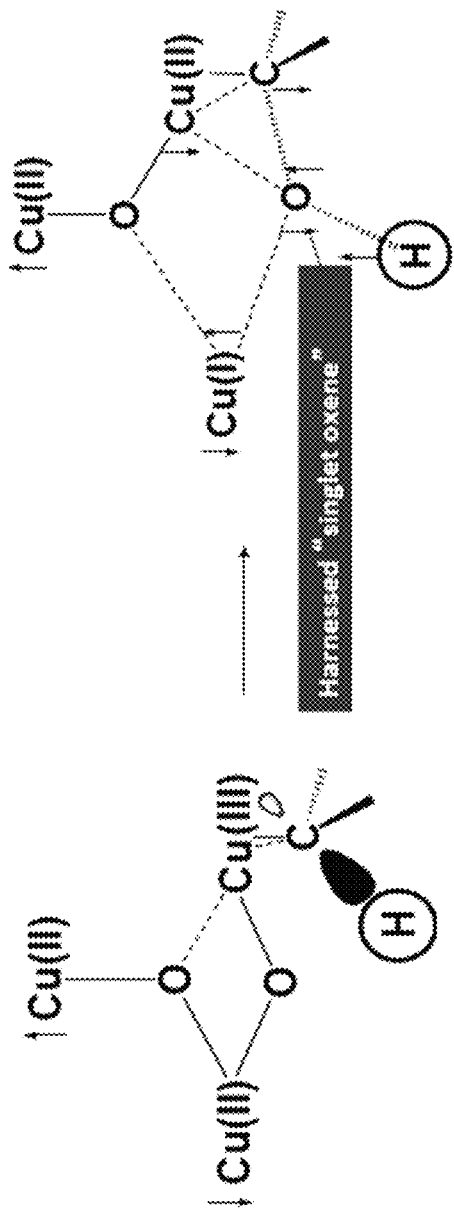
FIG. 13. Harnessing of a "singlet oxene" by activation of a Cu$^I$Cu$^I$Cu$^I$ cluster by dioxygen. [S. I. Chan, K. H.-C. Chen, S. S.-F. Yu, C.-L. Chen, S. S.-J. Kuo, *Biochemistry*, 43, 4421-4430 (2004).]

Upon activation by dioxygen, the $Cu^I Cu^I Cu^I$ cluster may form a $Cu^{II} Cu^{II}(\mu-O)_2 Cu^{III}$ intermediate, which harnesses a singlet oxene that can be transferred and inserted across one of the C—H bonds of methane in the transition state when the methane forms a suitable complex with the activated tricopper cluster (FIG. 13).

Density Functional Theory calculations were undertaken and compared the rates of converting methane to methanol upon the activation of tricopper and dicopper species by dioxygen. [*J Inorg Biochem.,* 100, (4) 801-9 (2006).] These results indicated that the dioxygen activated tricopper cluster was $10^4$ times more efficient in mediating this chemistry compared with the similar O-atom transfer between a $Cu^{III}((\mu-O)_2 Cu^{III}$ species formed from activation of a dicopper species and $10^2$ times more efficient compared with the $Cu^{II}(\mu-O)_2 Cu^{III}$ species formed by reductive activation of the $Cu^{III}((\mu-O)_2 Cu^{III}$ species.

Tricopper complexes were designed and synthesized in the hopes of developing a laboratory catalyst capable of efficient oxidation of hydrocarbons. The design of the ligands for these embodiments, are based on the following criteria:

1) The ligand may be able to trap three $Cu^I$ ions;
2) the coordinating atoms to the $Cu^I$ ions should be hard ligands to minimize the donation of electron density;
3) the $Cu^I$ ions may be coordinately unsaturated or contain coordinated solvent molecules that are readily displaced;
4) two of the three $Cu^I$ ions may be in a geometric juxtaposition to become activated by one molecule of $O_2$; and
5) adjacent $Cu^{II}$ ions may be strongly antiferromagnetically coupled after the cluster is activated by $O_2$ to maintain the cluster in an overall singlet state.

Figure 14:
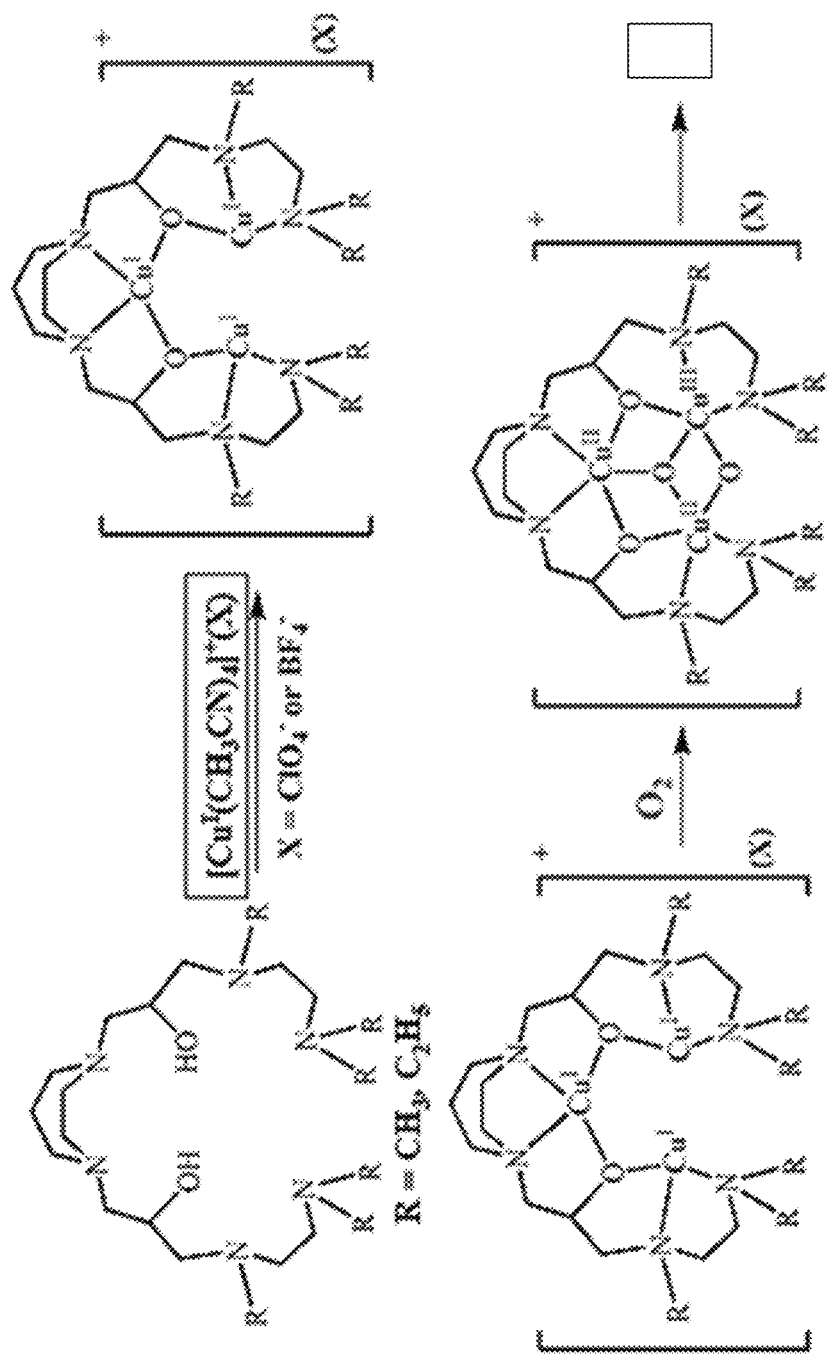
FIG. 14. Formation of the trinuclear Cu$^I$Cu$^I$Cu$^I$ complex and subsequent oxygenation.

Some of these trinucleating ligands (L) are shown in Scheme 1 (above). These ligands have been shown to form the $[Cu^I Cu^I Cu^I(L)]^{1+}$ complex in acetonitrile and to mediate facile O-atom transfer from the dioxygen activated tricopper complex to organic substrates (FIG. 14).

The first generation catalysts were based on the tricopper clusters supported by the ligands 7-Me and 7-Et. The $Cu^I Cu^I Cu^I$ complexes based on these ligands were shown to mediate efficiently the oxidation of benzil and 2,3-butanedione at room temperature by rapidly inserting an "O" atom across the central C—C bond of the β-dicarbonyl in each of these β-diketones followed by hydrolysis of the anhydride to yield benzoic acid and acetic acid, respectively. Insertion of an "O" atom into one of the C—H bonds of $CH_3CN$ to form $CH_2(OH)CN$ was also observed. Unfortunately, these oxidations are only stoichiometric, so these tricopper complexes were limited to oxidation reagents only. To render these tricopper complexes useful for catalysis, it was beneficial to regenerate the catalysts after each turnover.

The second generation of catalysts were based on the ligands 7-Thio and 7-Dipy and shown to be capable of efficient catalytic conversion of cyclohexane to cyclohexanol and cyclohexanone. This work revealed how to regenerate the catalyst by reducing the "spent" catalyst with $H_2O_2$ as a reducing agent after transfer of the "active" O-atom from the activated tricopper cluster to the substrate. By using $H_2O_2$ as an oxidant to activate the catalyst, and also as a reductant to regenerate the catalyst, the strategy led to the development of an efficient catalytic system for the oxidation of cyclohexane to cyclohexanol and cyclohexanone with many turnovers. In fact, the process is efficient and the extent of the process is determined only by the amounts of $H_2O_2$ used to drive the turnover. Under the experimental conditions studied, there is no evidence of any significant abortive cycling. Since cyclohexane is a benchmark substrate for the development of catalysts for hydrocarbon oxidation, a considerable amount of effort has been exerted in developing an understanding of the properties of this catalytic system.

Figure 15:
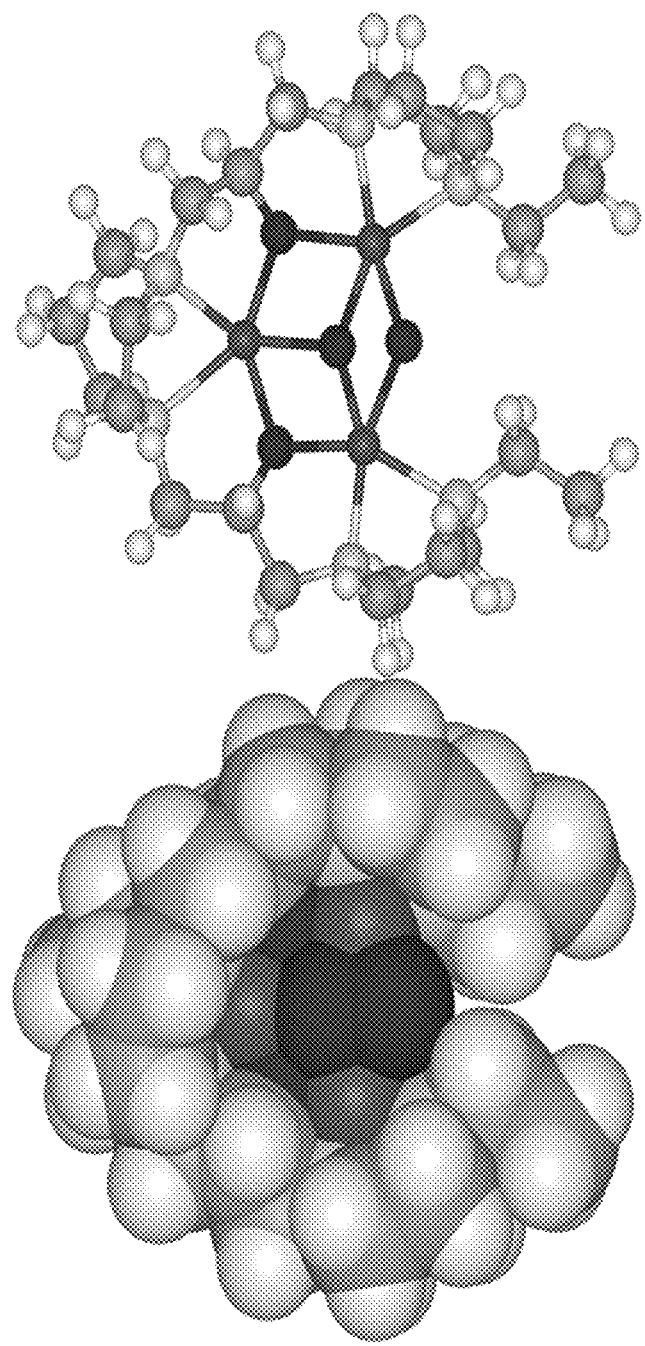
FIG. 15. CPK and ball-and-stick models of the dioxygen-activated Cu$^I$Cu$^I$Cu$^I$(7-N-Etppz) complex, namely, Cu$^{II}$Cu$^{II}$(μ-O)$_2$Cu$^{III}$(7-N-Etppz); where 7-N-Etppz stands for the organic ligand 3,3'-(1,4-diazepane-1,4-diyl)bis[1-(4-ethylpiperazine-1-yl)propan-2-ol]. Color code—white: hydrogen; grey: carbon; blue: nitrogen; red: oxygen; brown: copper. [*Angew. Chem. Int. Ed.* 52, 3731-3735 (2013).]

Experiments with cyclohexane led ultimately to the design a new ligand 7-N-Etppz for the development of a tricopper catalyst for methane oxidation. The $Cu^I Cu^I Cu^I$(7-N-Etppz) can mediate not only the efficient oxidation of methane but also many small alkanes including ethane, propane and butane. It is significant that there is no evidence of over-oxidation for methane, ethane and propane. This is a breakthrough in the development of an efficient catalyst for methane oxidation under ambient conditions. Recently, by immobilizing the $Cu^I Cu^I Cu^I$(7-N-Etppz) in mesoporous silicate nanoparticles, the homogeneous catalyst has been converted into a heterogeneous catalyst for methane oxidation with high turnovers and catalytic efficiencies. CPK and ball-and-stick models of $Cu^{II} Cu^{II}(\mu-O)_2 Cu^{III}$(7-N-Etppz), namely, the dioxygen-activated $Cu^I Cu^I Cu^I$(7-N-Etppz) complex, are shown in FIG. 15.

Figure 16:
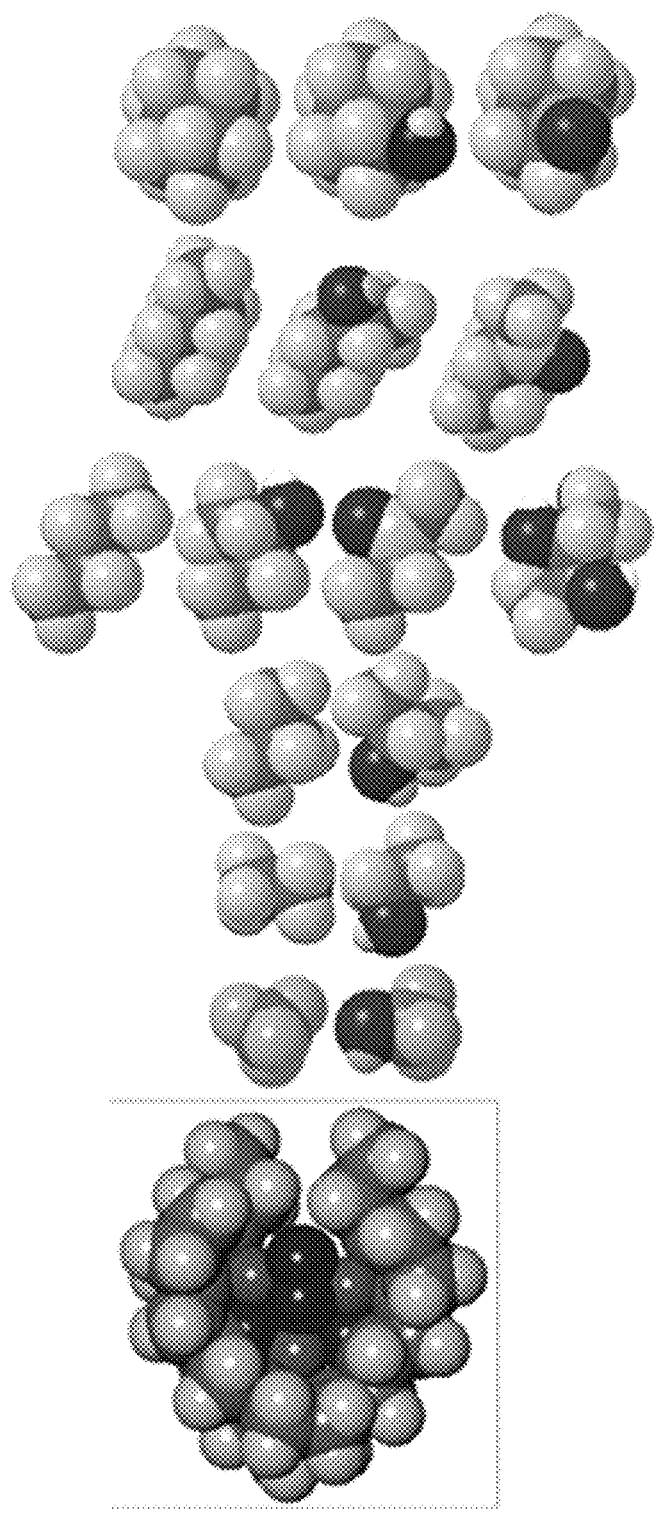
FIG. 16. Comparison of the CPK models of the dioxygen-activated Cu$^I$Cu$^I$Cu$^I$(7-N-Etppz) complex with those of methane, ethane, propane, butane, pentane. and cyclohexane and their alcohol/ketone products to illustrate the complementary hydrophobic contact surfaces required for binding of the substrates/products to the binding pocket of the activated tricopper cluster. [*Catal. Sci. Technol.*, 4, 930-935 (2014).]

In FIG. 16, the CPK model of the dioxygen-activated $Cu^I Cu^I Cu^I$(7-N-Etppz) complex is compared with those of methane, ethane, propane, butane, pentane, and cyclohexane and their alcohol/ketone products to compare the hydrophobic contact surface of the substrate-binding pocket on the copper catalyst with those of the hydrocarbon substrates and their products. To be an effective catalyst for oxidation of a given substrate, the substrate may recognize and bind to the hydrophobic binding pocket of the copper catalyst and the C—H bond to be oxidized may be in the position to form a transient complex for "O-atom" transfer in the transition state.

EXAMPLE 4

Developing an Efficient Catalyst for Controlled Oxidation of Small Alkanes Under Ambient Conditions The tricopper complex $[Cu^I Cu^I Cu^I$(7-N-Etppz)$]^{1+}$, where 7-N-Etppz denotes the ligand 3,3'-(1,4-diazepane-1,4-diyl)bis[1-(4-ethyl piperazine-1-yl)propan-2-ol], is capable of mediating facile conversion of methane into methanol upon activation of the tricopper cluster by dioxygen and/or $H_2O_2$ at room temperature. This is the first molecular catalyst that can catalyze selective oxidation of methane to methanol without over-oxidation under ambient conditions. When this $Cu^I Cu^I Cu^I$ tricopper complex is activated by dioxygen or $H_2O_2$, the tricopper cluster harnesses a "singlet oxene", the strongest oxidant that could be used to accomplish facile O-atom insertion across a C—H bond. To elucidate the properties of this novel catalytic system, the methane oxidation is examined over a wider range of conditions and other small alkanes including components of natural gas are considered. This experiment illustrates how substrate solubility, substrate recognition and the amount of $H_2O_2$ used to drive the catalytic oxidation can affect the outcome of the turnover, including regio-specificity, product distributions and yields of substrate oxidation.

Planet earth has enormous reserves of methane ($CH_4$), which can be harnessed by transformation into methanol ($CH_3OH$).[1] $CH_3OH$ is well established as a valuable commodity, both itself as a transportable fuel and as a source for derived chemicals, including $H_2$.[2] However, the controlled oxidation of $CH_4$ to $CH_3OH$ is challenging.[3] To begin with, the C—H bond in $CH_4$ is extremely inert due to its high bond-dissociation energy (105 kcal/mole).[3,4] In addition, the product $CH_3OH$ is prone to further oxidation to form other products.[5] Nevertheless, effective utilization of this valuable resource is not only economically advantageous, but also environmentally beneficial, as $CH_4$ is also a major contributor to global warming.[6]

Methane monooxygenases (MMO) are known to mediate efficient oxidation of $CH_4$ to $CH_3OH$ in methanotrophic bacteria under ambient conditions of temperature and pressure.[7] The membrane-bound particulate methane monooxygenase (pMMO) is multicopper protein.[8,9] The soluble methane monooxygenase (sMMO) is a non-heme iron protein.[10,11] Both systems exploit metal clusters to catalyze this difficult chemistry. Although there have been a number of x-ray crystal structures on these proteins,[12,13,14] progress toward understanding how the metal clusters in these enzymes mediate this process has been slow, and attempts to develop functional mimics of these catalytic centers have met with only limited success.[15]

The tricopper complex with the peptide HIHAMLT-MGDWD derived from the PmoA subunit of pMMO from *Methylococcus capsulatus* (Bath)[14] is capable of mediating efficient epoxidation of propene to propene oxide and hydroxylation of $CH_4$ to $CH_3OH$ when the $Cu^ICu^ICu^I$-peptide complex is activated by $O_2$. We have developed biomimetic models of the tricopper cluster for alkane oxidation. Various trinucleating ligands have been designed and prepared to support a triad of $Cu^I$ ions and these tricopper complexes have been shown to be capable of mediating efficient oxidation of small organic substrates when the fully reduced tricopper cluster is activated by dioxygen and/or hydrogen peroxide.[16-19] In particular, the tricopper complex $[Cu^ICu^ICu^I(7\text{-N-Etppz})]^{1+}$, where 7-N-Etppz stands for the organic ligand 3,3'-(1,4-diazepane-1,4-diyl)bis[1-(4-ethylpiperazine-1-yl)propan-2-ol] (Scheme 1), mediates the facile conversion of $CH_4$ to $CH_3OH$ in acetonitrile (MeCN) at room temperature when the tricopper cluster is activated by dioxygen ($O_2$).[16] Moreover, The oxidation of $CH_4$ to $CH_3OH$ in acetonitrile (MeCN) with the tricopper cluster complex $Cu^ICu^ICu^I(7\text{-N-Etppz})]^{1+}$ can be rendered catalytic when the fully reduced tricopper complex is regenerated by two-electron reduction of the partially oxidized tricopper complex by a molecule of $H_2O_2$. This is the first molecular catalyst that can catalyze the selective oxidation of $CH_4$ to $CH_3OH$ at ambient conditions.

This example examines the methane oxidation over a wider range of conditions in order to delineate the factors influencing the turnover frequency (TOF) of the catalyst and the turnover number (TON). The example also extends the study to other small alkanes including components of natural gas including ethane, propane and butane. The purpose is to study the effects of substrate recognition, substrate concentration, the effects of futile cycles on the outcome of the substrate oxidation, including regio-specificity, product yields and distribution, as well as the overall turnover frequency of the substrate oxidation.

The synthesis and spectroscopic characterization of the 7-N-Etppz ligand as well as the preparation of the $[Cu^ICu^I-Cu^I(7\text{-N-Etppz})](ClO_4)$ complex have been described earlier.[16] When the $Cu^ICu^ICu^I$ complex is treated with $O_2$ in the absence of substrate, it forms the $[Cu^{II}Cu^{II}(\mu\text{-O})Cu^{II}(7\text{-N-Etppz})](ClO_4)_2$ species, the same fully oxidized "dead-end" species previously reported for all tricopper complexes of this series.[17-19]

The tricopper complex is capable of facile oxidation of alkanes at ambient conditions. In this example, 22.7 μmoles (1 equiv.) of $[Cu^ICu^ICu^I(7\text{-N-Etppz})]^{1+}$ are used to catalyze the oxidation of various hydrocarbons by $H_2O_2$ in 3 ml of MeCN (or EtCN) in a 60 ml glass sample bottle at room temperature. As the reduced tricopper complex is extremely air sensitive, it is beneficial to perform the substrate oxidation experiments under a purified nitrogen atmosphere inside the glove box. The reaction mixture is vigorously stirred with a magnetic stirring bar for various times up to 1 h using different sample bottles. At designated intervals, a sample bottle is removed from the glove box to identify the products and determine the product yields by GC. 3 μl of nitrobenzene is added to the solution to provide an internal standard (IS) for quantitation of the products.

Of the various hydrocarbons studied, n-pentane, n-hexane, cyclohexane, and cyclohexene are liquids. Although each of these liquid substrates is not miscible with MeCN in all proportions, it has sufficient solubility and the substrate oxidation could be initiated by adding appropriate amounts of the hydrocarbon to the solvent containing the tricopper catalyst followed by adding the desired amounts of $H_2O_2$, and the solution is mixed vigorously. The data for these hydrocarbons are obtained with 11.3 mmoles (500 equiv.) of the hydrocarbon in each case and the turnover is driven by 200 equiv. of $H_2O_2$ from a 33% aqueous solution in the experiment.

In the case of $CH_4$, ethane, propane and n-butane, the glass sample bottle is first sealed tightly with a rubber cap and evacuated before one of these gas substrates (100 ml NTP or $4.17 \times 10^{-3}$ mole, ~200 equiv,) is injected into the solvent containing the tricopper catalyst using a gas syringe. 2.27 mmoles of $H_2O_2$ (100 equiv.) from a 33% aqueous solution is then injected using a separate syringe to initiate the oxidation of ethane, propane or n-butane. Again, the reactions are carried out with vigorous agitation of the solution. In the case of $CH_4$, 0.39 mmoles (20 equiv.) of $H_2O_2$ are used and the $H_2O_2$ solution is added dropwise over 2-3 min. Given the limited solubility of these hydrocarbon gases in MeCN, the extent of hydrocarbon oxidation depends on the gas pressure in the overhead space (starting pressure 1.67 atm), as well as the amount of the gas dissolved in the solution. With the low solubility of $CH_4$ in MeCN, we use only 20 equiv. of $H_2O_2$ in the initial experiments to mitigate abortive cycling of the catalyst. The amounts of $H_2O_2$ added have a dramatic effect on the turnover, as demonstrated by performing the $CH_4$ oxidation using 20, 40, 60 and 80 equiv. of $H_2O_2$, as well as incremental additions of $H_2O_2$ over the time course of the experiment initiated with 20 equiv. of $H_2O_2$.

Additionally, the $[Cu^ICu^ICu^I(7\text{-N-Etppz})]^{1+}$ complex is also used to mediate the oxidation of $CH_3OH$, ethanol, isopropanol, and 2-butanol by $H_2O_2$. These experiments are performed with 200 equiv. of $H_2O_2$ from 35% aqueous solution, 500 equiv. of substrate, and one equiv. (22.7 pmoles) of the tricopper complex in MeCN (total volume 3 ml) at room temperature for 1 h.

Figure 17:
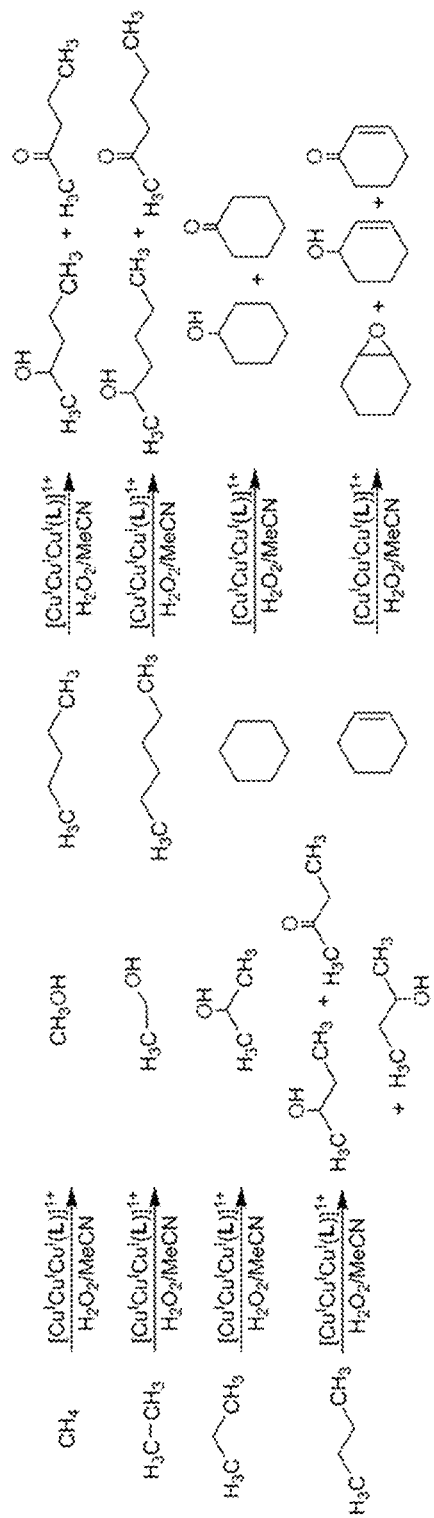
FIG. 17 shows reactions and oxidation products of methane, ethane, propane, n-butane, n-pentane, n-hexane, cyclohexane, and cyclohexene facilitated by the tricopper catalyst [Cu$^I$Cu$^I$Cu$^I$(L)]$^{1+}$ in acetonitrile, where L is a ligand as defined above in Formula 1 and hydrogen peroxide acts as both the oxidizing and reducing agent. [*Catal. Sci. Technol.*, 4, 930-935 (2014).]

We summarize in FIG. 17 and Table 7 the findings obtained when 1 equiv. (22.7 μmoles) of $[Cu^ICu^ICu^I(7\text{-N-Etppz})]^{1+}$ is used to catalyze the oxidation of various hydrocarbons by $H_2O_2$ at room temperature under the conditions described above.

Only CH$_3$OH, ethanol, and 2-propanol are produced in the catalytic oxidation of CH$_4$, ethane, and propane mediated by the tricopper cluster, respectively. There is no evidence for over-oxidation of these hydrocarbons to form their corresponding aldehydes or ketones. In the case of n-butane, however, we observe the formation of 2-butanol, 2-butanone, and 2,3-butanediol. For n-pentane, the products are 2-pentanol and 2-pentanone, and for n-hexane, 2-hexanol and 2-hexanone, with preference for the ketone in both cases. With cyclohexane, cyclohexanol and cyclohexanone are formed in roughly equal proportions. For cyclohexene, the oxidation yields the epoxide, cyclohexenol and cyclohexenone, in favor of the epoxide and cyclohexenone.

Figure 18:
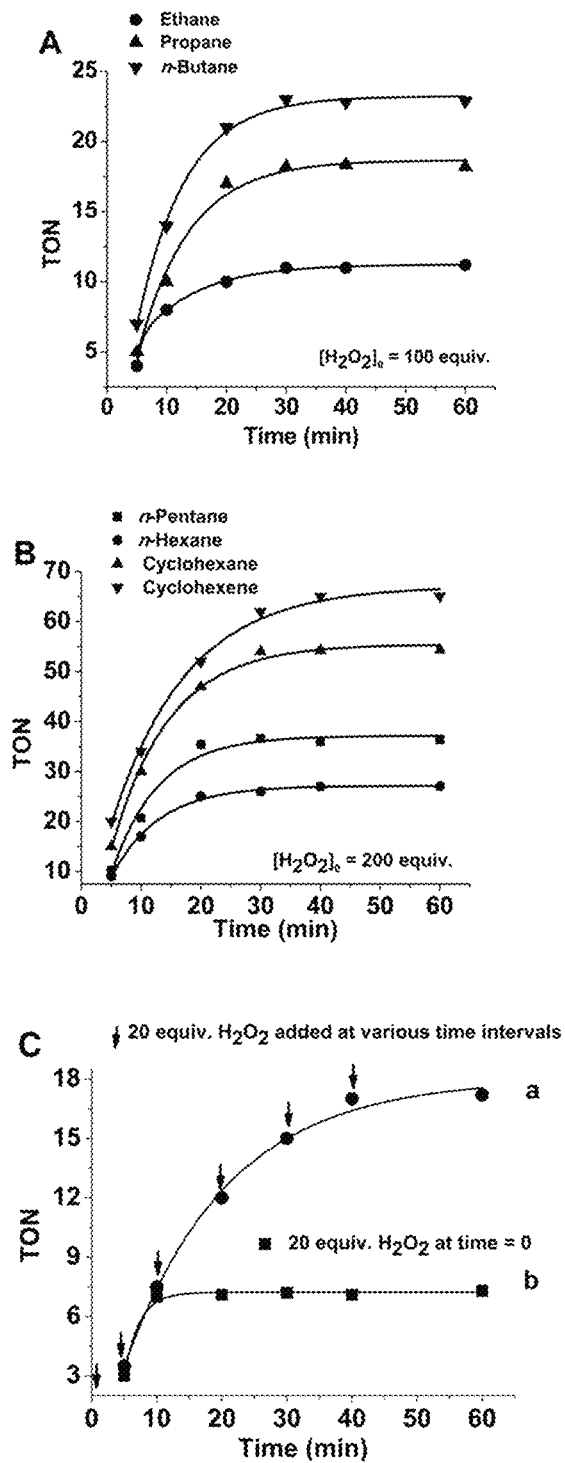
FIG. 18 shows the time course oxidation of various hydrocarbons under the experimental conditions in Example 4. The figures plot the turnover number (TON) which is a measure the equivalent oxygens transferred to the hydrocarbon substrate with respect to time over the course of an hour. [*Catal. Sci. Technol.*, 4, 930-935 (2014).]

The time courses of the oxidation of the various hydrocarbons are shown in FIG. 18, where we have plotted the equivalents of the oxo-products produced at various times up to one hour, weighted according to the number of oxidizing equivalents transferred (TON). These data reveal that the oxidation is indeed very rapid for all the hydrocarbons studied. In every case, the H$_2$O$_2$ used to drive the turnover is almost exhausted in less than 20 min, well before the completion of the one-hour study. This is true even in the case of CH$_4$.

This example also discloses the catalytic cycle of the tricopper complex. We depict in Scheme 3 panel A the turnover cycle for the catalytic oxidation of CH$_4$ mediated by [Cu$^I$Cu$^I$Cu$^I$(7-N-Etppz)]$^{1+}$ in the presence of O$_2$ and H$_2$O$_2$. Although we show here that the tricopper complex is activated by O$_2$, the activation could also be accomplished with two molecules of H$_2$O$_2$. Thus, the catalytic cycle can be carried out in the presence of H$_2$O$_2$ alone, as we have described earlier[18,19] and will demonstrate again here with the oxidation of alkane substrates. In either scenario, one additional molecule of H$_2$O$_2$ is required to serve as the "sacrificial" reductant to re-reduce the "spent" catalyst in order to regenerate the catalyst for another catalytic turnover. There is, however, more than a subtle difference between the two scenarios. In sufficiently high concentrations of O$_2$, H$_2$O$_2$ is no longer a good reductant and typically only a single turnover of the catalyst is observed with O$_2$ as the oxidant under these conditions. As will be understood by one having skill in the art, a different "sacrificial" reductant can be used to regenerate the catalyst.

Scheme 3 panel B depicts abortive cycling of the catalytic system, a competing process that aborts the activated tricopper cluster by direct reduction with H$_2$O$_2$, the "sacrificial reductant" in this case. The activated tricopper cluster harnessing the "oxene" has a high redox potential so it can be aborted if the transfer of the harnessed O-atom to the substrate molecule is not sufficiently rapid. This process, which decreases the catalytic efficiency of the catalytic system, becomes operative when k$_{abortive}$ [H$_2$O$_2$]>k$_{OT}$ [substrate], where k$_{OT}$ and k$_{abortive}$ denote the bimolecular rate constants for the "O-atom" transfer reaction from the activated tricopper cluster to the organic substrate and the abortive reduction, respectively, a scenario that obtains at high H$_2$O$_2$ or low substrate concentrations.

A measure of the effectiveness of the catalytic system for the oxidation of the various hydrocarbons examined in this study is given by the percentage of the H$_2$O$_2$ consumed by productive cycling for the amount of H$_2$O$_2$ used to drive the turnover. We define the catalytic efficiency by the ratio of the productive turnovers of the catalyst to the total number of turnovers of the catalyst including both productive and futile cycles during the course of the experiment. When the catalytic turnover is driven by H$_2$O$_2$ alone, 3 molecules of H$_2$O$_2$ are consumed for a productive cycle that leads to product formation and 4 molecules of H$_2$O$_2$ for an abortive turnover. These catalytic efficiencies are listed in the last column of Table 7 for the various hydrocarbon substrates examined in this study under the conditions highlighted in columns 2 and 3. In this analysis, we have assumed that the total amount of H$_2$O$_2$ introduced into the medium to drive the substrate oxidation has been exhausted during the 1 h experiment, a good approximation when 200 equiv. of H$_2$O$_2$ are used. In any case, according to this indicator, the tricopper complex [Cu$^I$Cu$^I$Cu$^I$(7-N-Etppz)]$^{1+}$ is indeed an efficient catalyst for the oxidation of hydrocarbons at room temperature.

The catalyst system shows a high catalytic efficiency. For example, cyclohexane is the benchmark substrate for the type of catalytic reactions under discussion here.[18] The bond energy associated with the C—H bond is 99.5 kcal/mole, which is 5 kcal/mole lower than for CH$_4$. Under the conditions of our experiments, there is essentially no abortive cycling noted for this substrate. Time-course study indicates that practically all the H$_2$O$_2$ used to turn over the catalyst for substrate oxidation is consumed within 30 min (FIG. 18). Thus, the oxidation of cyclohexane to cyclohexanol and cyclohexanone mediated by the [Cu$^I$Cu$^I$Cu$^I$(7-N-Etppz)]$^{1+}$ complex with H$_2$O$_2$ as the O-atom source is extremely efficient. Similar results have been obtained for this substrate with tricopper complexes supported by other trinucleating ligands.[18] No abortive cycling is observed with cyclohexene as well. This substrate is oxidized to cyclohexenol, cyclohexenone and the epoxide. Evidently, electrophilic syn addition of the O-atom across the C=C bond is more facile than direct C—H insertion. In any case, both cyclohexane and cyclohexene are sufficiently soluble in MeCN that k$_{OT}$ [substrate]>k$_{abortive}$ [H$_2$O$_2$] under the conditions of the experiments.

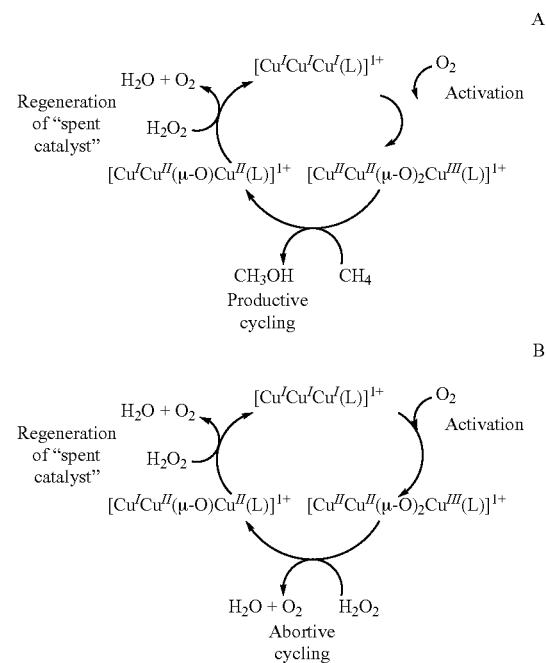

Scheme 3 Shown in panel A is the turnover cycle driven by H$_2$O$_2$ in the catalytic oxidation of CH$_4$ mediated by [Cu$^I$Cu$^I$Cu$^I$(7-N-Etppz)]$^{1+}$ by O$_2$ and; panel B depicts abortive cycling of the catalytic system, a competing process that aborts the activated tricopper cluster by direct reduction with $H_2O_2$.

We have also observed a very high catalytic efficiency (98%) in our experiment on methane oxidation. However, here we have used only 20 equiv. of $H_2O_2$ to drive the turnover. With the lower amount of $H_2O_2$ employed to drive the oxidation, the TON is low. It also slows down the turnover of the tricopper catalyst. More importantly, however, the lower $H_2O_2$ concentration mitigates abortion of the activated catalyst, keeping more of the $H_2O_2$ for productive oxidative turnover, as evidenced by the high fraction of the $H_2O_2$ that is consumed by productive cycling of the catalyst. As expected, when greater amounts of $H_2O_2$ are used to oxidize the methane, the TON diminishes abruptly. With 40 equiv. of $H_2O_2$, the catalytic efficiency is only 30%, and with 80 equiv., only a meager 6% of the turnover of the catalyst results in the formation of methanol.

For methane, the factor limiting the turnover is the low solubility of the gas in MeCN. Higher amounts of $H_2O_2$ can be used if the concentration of $CH_4$ in the solution is higher to speed up the second-order O-atom transfer reaction mediated by the catalyst. Although there is an excess of $CH_4$ in the system, the methane concentration is limited by the solubility of the gas in the solvent under the headspace gas pressure. We have repeated the oxidation experiment with the volume of the solvent increased from 3 ml to 6 ml to ensure that the process is not limited by the availability of the hydrocarbon. The same amount of the tricopper catalyst is used and the same amount of $H_2O_2$ is used to drive the turnover. Thus, the concentration of the tricopper catalyst and the starting concentration of the $H_2O_2$ are now a factor of 2 lower, but the $CH_4$ concentration remains the same. Accordingly, the turnover should be slower, although the catalytic efficiency might be slightly improved. Essentially the same TON (~7) is obtained at the end of the 1 h experiment. Thus, it is not the availability of $CH_4$ that is limiting the TON, rather the amount of $H_2O_2$ used to drive the process. To corroborate this conclusion, we add an additional 20 equiv. of $H_2O_2$ after 8-10 min when it is apparent that the initial amount has already been consumed. As expected, the turnover of the catalyst quickly proceeds to yield additional product, the TON rapidly doubling to ~12 within another 15 min (data not shown). In a separate experiment with same conditions, the methane oxidation is initiated with 20 equiv. of $H_2O_2$ (at 3 min), followed by incremental dropwise additions of 20 equiv. at 10 min, 20 min, 30 min, and 40 min, and a TON ~18 is eventually reached (FIG. 18 panel C). These observations clearly underscore the interplay between productive cycling and abortive cycling in the catalytic methane oxidation driven by $H_2O_2$. The catalytic efficiencies observed for the other substrates (ethane, propane, n-butane, n-pentane and n-hexane) reinforce this picture.

A valuable characteristic of the present invention is the lack of any substantial over oxidation in small alkanes. As noted earlier, $CH_4$, ethane and propane are oxidized only to $CH_3OH$, ethanol and 2-propanol, respectively. There is no evidence for any over-oxidation of these alkanes during the catalytic turnover. Consistent with this finding, $CH_3OH$, ethanol and 2-propanol are not found to be substrates of the catalytic system. When the $[Cu^I Cu^I Cu^I(7\text{-N-Etppz})]^{1+}$ complex is used to mediate the oxidation of these substrates with $H_2O_2$, there is no aldehyde or ketone detected by GC. The propensity to over-oxidation is one of the greatest challenges in the design of a catalyst for the conversion of $CH_4$ into $CH_3OH$. Thus, with the $[Cu^I Cu^I Cu^I(7\text{-N-Etppz})]^{1+}$ complex, we have achieved one of the main objectives in our development of a catalytic system for $CH_4$ hydroxylation.

In our design of the tricopper complex for $CH_4$ oxidation, we have built in a small molecular surface near the basal coppers of the triad for the recognition of the hydrophobic $CH_4$ molecule. This weak interaction facilitates the formation of a transient complex so that it can reach the transition state for the obligatory oxene transfer to oxidize the substrate when the tricopper cluster is activated. On the other hand, the binding surface is sufficiently small and hydrophobic that it is unable to accommodate the product $CH_3OH$ once the latter is formed. Evidently, this is true for ethane and propane as well. For these smaller alkanes, the product alcohols do not have sufficient binding affinity for the "active-site" pocket and are released as soon as the product is formed.

TABLE 7

Catalytic oxidation of various hydrocarbons by $H_2O_2$ at room temperature and the efficiency of the catalyst for different substrates.

| Substrate (C—H bond energy, kcal/mol) | Substrate (moles) | $H_2O_2$ (equiv.)[a] | Products (equiv.) | | | Catalytic turnovers (A + 2B + 2C) | Abortive cycles | Catalytic Efficiency[b] (%) |
|---|---|---|---|---|---|---|---|---|
| | | | alkanol (A) | alkanone (B) | alkane diol (C) | | | |
| Methane (104.5) | $4.17 \times 10^{-3}$ | 20 | 6.5 | — | — | 6.5 | 0.125 | 98 |
| Ethane (101.1) | $4.17 \times 10^{-3}$ | 100 | 11 | — | — | 11 | 16.75 | 40 |
| Propane (100.4) | $4.17 \times 10^{-3}$ | 100 | 18.2 | — | — | 18.2 | 11.35 | 62 |
| n-Butane (98.2) | $4.17 \times 10^{-3}$ | 100 | 6 | 4 | 4.4 | 22.8 | 7.9 | 74 |
| n-Pentane (98) | $1.13 \times 10^{-2}$ | 200 | 1.2 | 13.8 | — | 28.8 | 28.4 | 50 |
| n-Hexane (98) | $1.13 \times 10^{-2}$ | 200 | 5.2 | 18 | — | 41.2 | 19.1 | 68 |
| Cyclohexane (99.3) | $1.13 \times 10^{-2}$ | 200 | 26 | 17 | — | 60 | 5 | 92 |

TABLE 7-continued

Catalytic oxidation of various hydrocarbons by $H_2O_2$ at room temperature and the efficiency of the catalyst for different substrates.

| Substrate (C—H bond energy, kcal/mol) | | | alkanol (A) | alkanone (B) | epoxide (D) | Catalytic turnovers (A + 2B + D) | | |
|---|---|---|---|---|---|---|---|---|
| Cyclohexene (83.9) | $1.13 \times 10^{-2}$ | 200 | 4.2 | 21 | 18 | 64.2 | 1.85 | 97 |

[a] 1 equiv. of catalyst corresponds to 22.7 μmoles.
[b] Catalytic efficiency denotes the effectiveness of the $[Cu^ICu^ICu^I(7\text{-N-Etppz})]^{1+}$ complex as a catalyst for hydrocarbon oxidation based on the amount of $H_2O_2$ used to drive the turnover. It is given by the ratio of the productive turnovers of the catalyst to the total number of turnovers of the catalyst including both productive and futile cycles during the course of the 1-hour experiment.

This is apparently not the case with the alcohols formed with the higher alkanes. For example, in the case of n-butane, the 2-butanol evidently resides in the active site long enough for another round of oxidation to produce 2-butanone and the 2,3-butanediol. Since 2-butanol by itself is not a good substrate of the tricopper cluster for conversion to 2-butanone or 2,3-butanediol, the over-oxidation is evidently kinetically controlled. When 2-butanol is employed as the substrate in our catalytic system over the 1 h incubation experiment, only a very small amount of 2-butanone is formed (TON ~1). Surprisingly, with n-pentane, n-hexane, and cyclohexane, the alcohol is only further oxidized to give the ketone but the diol is not formed. This result suggests that the details of the interaction between the molecular binding surfaces of the tricopper complex and the substrate are important for the regio-specificity of the oxidation. For the longer alkanes, cyclohexane, and cyclohexene, van der Waals interactions between the aliphatic parts of the substrate and the binding surface of the activating tricopper cluster may dictate the positioning and orientation of these hydrocarbon substrates in the binding pocket. From examination of a CPK model of the activated tricopper complex together with models of various hydrocarbon substrates and their oxidized products, we surmise that the molecular surfaces on both the tricopper complex and the substrate/products dictate the specific van der Waals interactions and binding modes that lead to the regio-specificity observed in the oxidation (FIG. 16).

With the catalytic system described here, the TON, or the amount of products formed during the time course of the experiment, is largely determined by the amounts of $H_2O_2$ used to drive the turnover of the tricopper catalyst after allowance is made for the catalytic efficiency. In principle, it is possible to increase the TON by using larger amounts of $H_2O_2$ or adding incremental amounts of $H_2O_2$ to the system at various times as we have demonstrated here. For example, when the $[Cu^ICu^ICu^I(7\text{-N-Etppz})]^{1+}$ complex is used to mediate the oxidation of cyclohexane, a TON of ~120 can be reached in this manner. However, as a batch process, water accumulates in the solution with increasing amounts of $H_2O_2$ solution added so that eventually the tricopper complex trashes out of solution. The catalyst is robust in MeCN containing small amounts of $H_2O$ otherwise.

The estimated turnover frequency (TOF) of the catalyst can be calculated at early times when the $H_2O_2$ concentration≈$[H_2O_2]_0$. The rate of turnover of the catalyst is limited by the regeneration of the "spent" catalytst after either a productive or abortive event, and it is directly proportional to the $[H_2O_2]$ available at a particular instance. The TOF can be estimated from the rate of product formation at early times under conditions in which there is no abortive cycling. In the cases of cyclohexane and cyclohexene, for which the catalytic efficiencies approach unity, TOF ~$10^{-1}$ $s^{-1}$ at 200 equiv. of $H_2O_2$. A TOF of ~$5 \times 10^{-3}$ $s^{-1}$ is obtained when $CH_4$ is converted into $CH_3OH$ using 20 equivalents of $H_2O_2$. Were it possible to drive the oxidation of methane using 200 equiv. of $H_2O_2$ without significant abortive cycling, the TOF could be 10 times higher (~$5 \times 10^{-2}$ $s^{-1}$). This analysis underscores the interplay between turnover rate and catalytic efficiency in the performance of the present catalytic system for the conversion of $CH_4$ to $CH_3OH$.

In summary, this example provides specific data showing the $[Cu^ICu^ICu^I(7\text{-N-Etppz})]^{1+}$ catalyst promotes efficient oxidation of $CH_4$ as well as other small alkanes with $H_2O_2$ as the oxidant in MeCN at room temperature. The oxidation is regio-specific, and the turnover number is only limited by the amount of $H_2O_2$ used to drive the process under controlled conditions.

A batch "reactor" has been developed to allow evaluation of the working principles of the catalytic system and to assess its efficacy toward alkane oxidation. For scale up, a flow system may be used to remove $CH_3OH/H_2O$ continuously with concomitant input of $H_2O_2/H_2O$ to drive the catalytic oxidation. In some emobidments for $CH_4$ oxidation, the composition of the tricopper complex is functional in a solvent system such as perfluorohydrocarbons with greater solubility for the $CH_4$ gas. Alternatively, the present tricopper catalyst can be encapsulated into the pores of a mesoporous material and the system is converted into a heterogeneous catalyst.

Materials and Methods:

General. All chemicals were purchased from commercial sources as reagent grade quality and used as received unless stated otherwise. Acetonitrile (MeCN) was distilled under nitrogen from $CaH_2$—$P_2O_5$; and stored in dried, $N_2$-filled flasks over 4 Å molecular sieves. Nitrogen was purged through these solvents before use. Oxygen gas (99.8%, Fong Ming), used for oxygenation, was dried by passing it through two short columns in succession of $P_2O_5$ and Drierite. Manipulations, reactions, and transfers were conducted under nitrogen according to Schlenk techniques or in a glove box (nitrogen gas).

Figure 19:
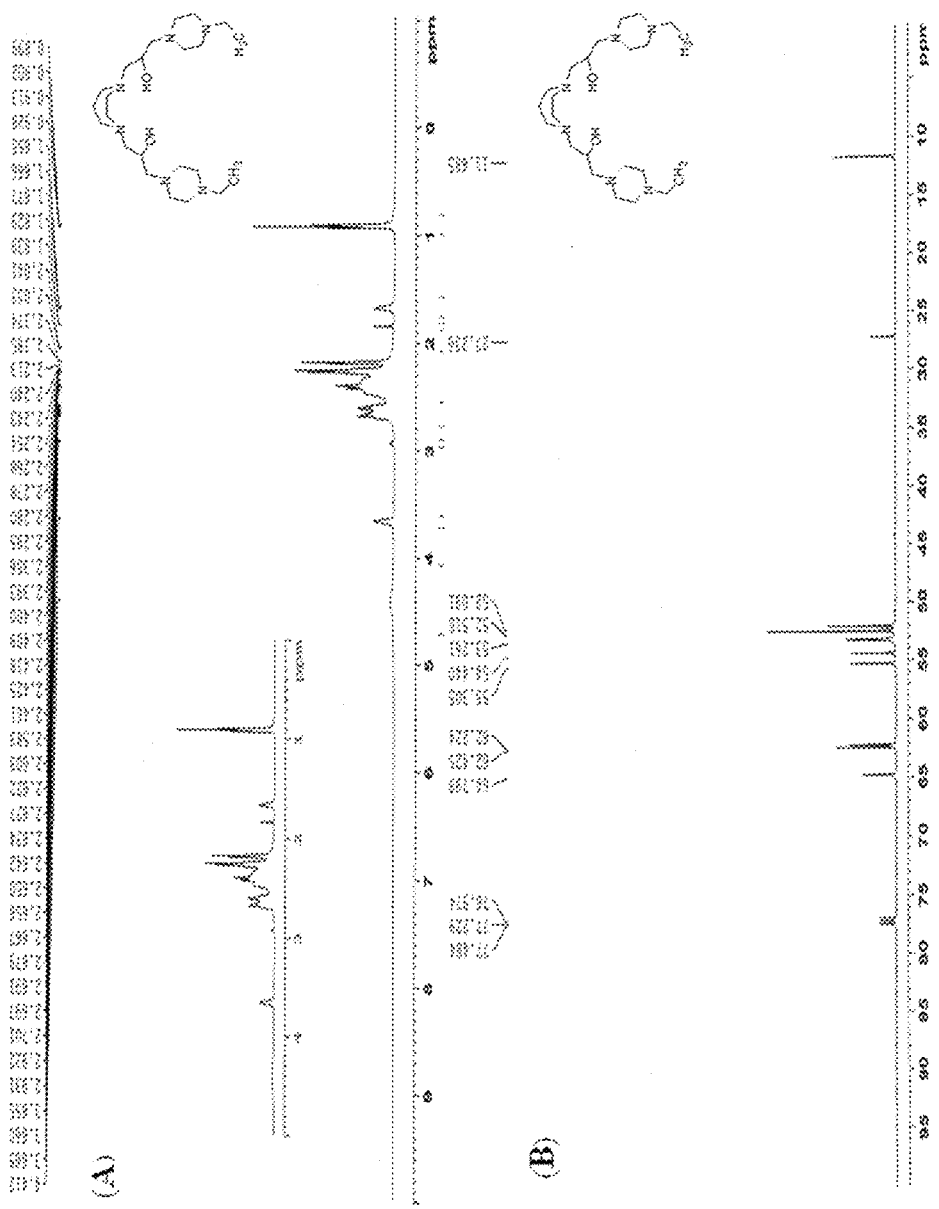
FIG. 19. $^1$H NMR (A) and $^{13}$C NMR (B) spectra of the 7-N-Etppz ligand.
Figure 20:
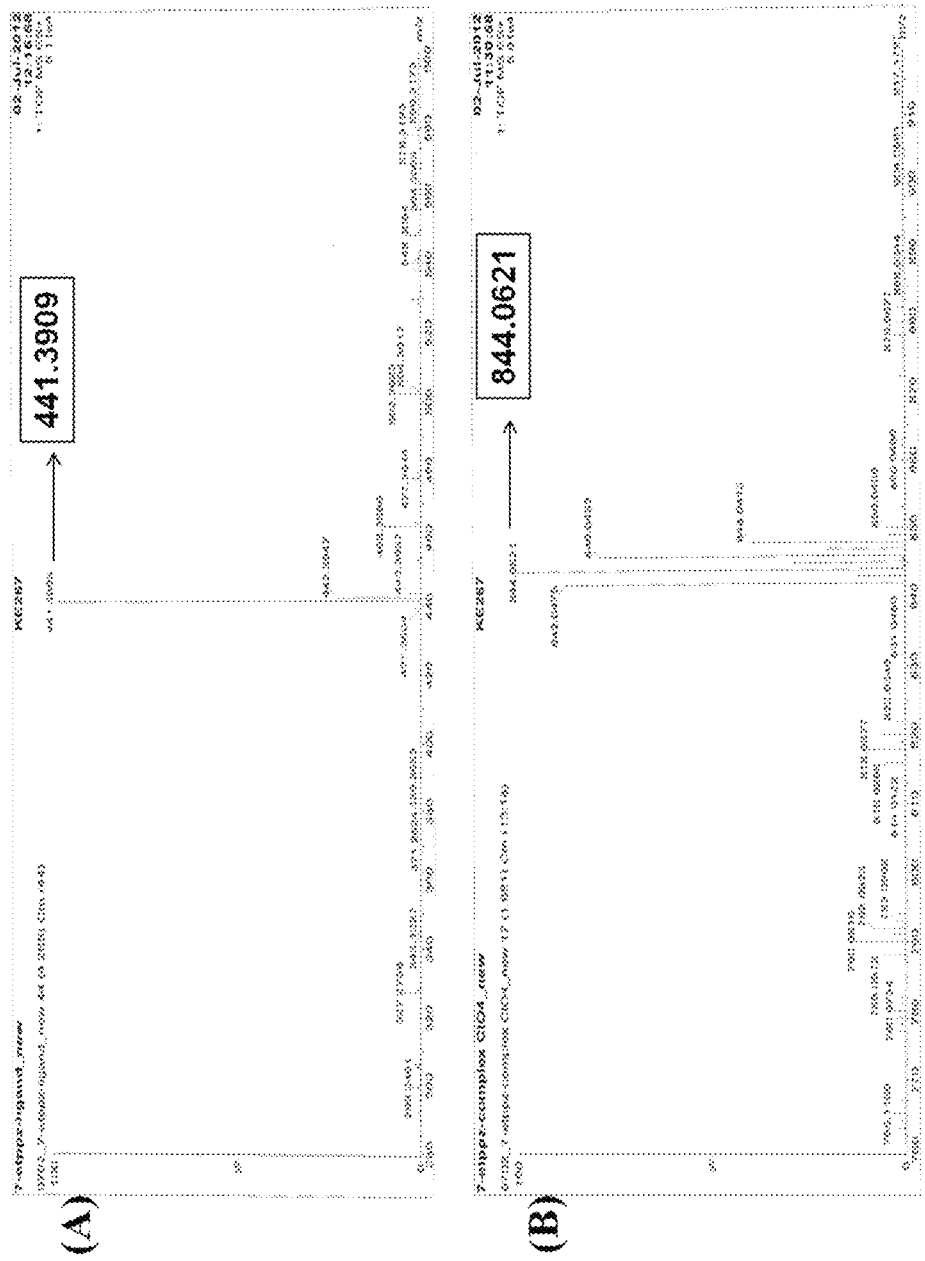
FIG. 20. FAB mass spectra of the 7-N-Etppz ligand (A) and the oxygenated [Cu$^I$Cu$^I$Cu$^I$(7-N-Etppz)](ClO$_4$)$_2$ (B). The multiple peaks in the range of m/z 842~848 amu with the peak maximum at m/z 844 amu are assigned to the [Cu$^{II}$Cu$^{II}$(μ-O)Cu$^{II}$(7-N-Etppz)](ClO$_4$)$_2$ species.

Synthesis of the ligand 3,3'-(1,4-diazepane-1,4-diyl)bis[1-(4-ethylpiperazine-1-yl)propan-2-ol] (7-N-Etppz). The ligand 7-N-Etppz was synthesized according to established procedures. The compound 3,3'-(1,4-diazepane-1,4-diyl)bis(1-chloropropan-2-ol) (1) was first prepared.[1] A solution of epichlorohydrin (1.85 g, 20 mmol) in methanol (15.0 ml) was added drop-wise to a solution of homopiperazine (1.00 g, 10 mmol) in methanol (30.0 ml) with stirring at −5° C. After stirring for 72 h at −5° C., the resulting mixture was purified by column chromatography on silica gel using 8% $CH_3OH$ in dichloromethane (DCM) as the eluent. A slightly modified procedure from that previously reported by Hayashi et al.[2] was then used to couple 1-ethylpiperazine to (1). A MeCN (15.0 ml) solution containing (1) (4.28 g, 15 mmol), 1-ethylpiperazine (3.46 g, 30 mmol), and $K_2CO_3$ (4.15 g, 30 mmol) was heated to 70-80° C. for 48 h ($N_2$ atmosphere). After cooling to room temperature, the solution was filtered, and upon evaporation of the filtrate to dryness, the ligand 7-N-Etppz was obtained. $^1$H NMR (FIG. 19A) δ ($CDCl_3$, 300 MHz): 1.8 (t, 2H, $CH_3$); 2.05-2.93 (m, $CH_2$); 3.6 (s, 2H, CH), 4.4 (s 2H, CH). $^{13}$C NMR (FIG. 19B) δ (300 MHz, $CDCl_3$): the major peaks appeared at 11.6, 11.65, 27.23, 52.0, 52.5, 53.2, 54.4, 55.3, 62.2, 62.4, and 64.7. ESI-MS (positive ion): m/z 441 (FIG. 20A).

Figure 21:
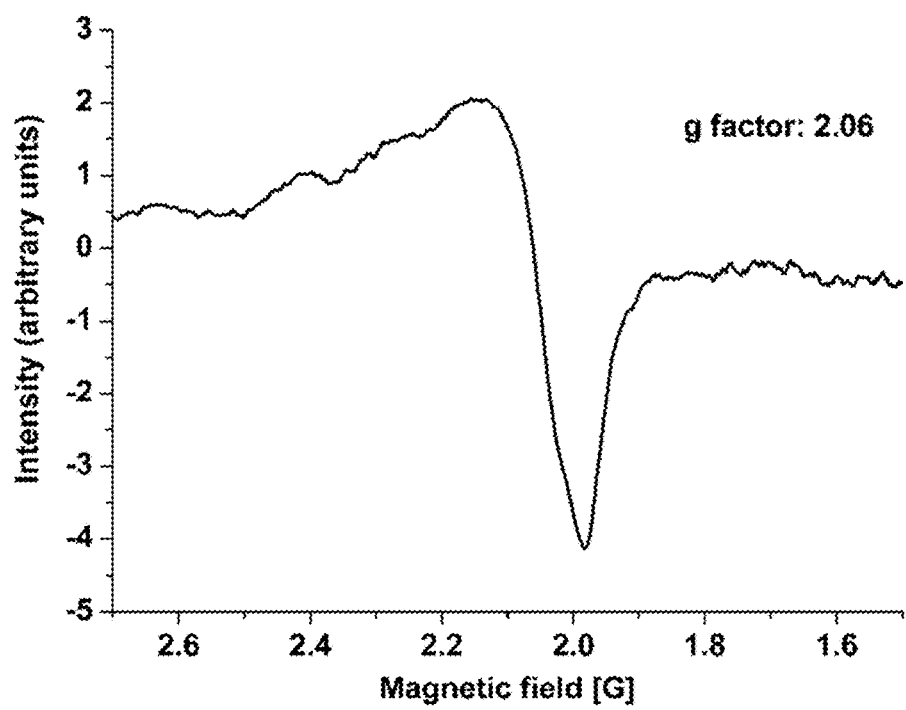
FIG. 21. 77K EPR spectrum of the [Cu$^{II}$Cu$^{II}$(μ-O)Cu$^{II}$(7-N-Etppz)](ClO$_4$)$_2$ species formed by oxidation of the [Cu$^I$Cu$^I$Cu$^I$(7-N-Etppz)](ClO$_4$) complex by dioxygen in acetonitrile (MeCN).

Preparation of copper complexes. The tricopper complexes $[Cu^ICu^ICu^I(7\text{-}N\text{-}Etppz)]^{1+}$ and $[Cu^{II}Cu^{II}(\mu\text{-}O)Cu^{II}(7\text{-}N\text{-}Etppz)]^{2+}$ were prepared as previously described.[3-6] The FAB MS of $[Cu^{II}Cu^{II}(\mu\text{-}O)Cu^{II}(7\text{-}N\text{-}Etppz)]^{2+}$ complex showed a positive ion mass peak at m/z 844 (FIG. 20B). The 77K EPR spectrum exhibited a featureless isotropic signal centered at g 2.06 (FIG. 21).

Oxidations of $CH_4$ to $CH_3OH$ mediated by $[Cu^I Cu^ICu^I(7\text{-}N\text{-}Etppz)]^{1+}$. Oxidations of methane gas ($CH_4$) by $O_2$ mediated by the tricopper complex $[Cu^ICu^ICu^I(7\text{-}N\text{-}Etppz)]^{1+}$ were carried out as follows. First, $[Cu^ICu^ICu^I(7\text{-}N\text{-}Etppz)]^{1+}$ (0.0113 mmol) was added to 3 ml of MeCN in a 60 ml glass sample bottle. As the reduced tricopper complexes are extremely air sensitive, it is beneficial to perform the experiment under a purified nitrogen atmosphere inside the glove box. Before removing the sample from the glove box, the sample bottle was sealed tightly with a rubber cap and evacuated before injecting $O_2$ (10 ml at STP, 0.44 mmol) and $CH_4$ (100 ml STP, 4.4 mmol) using gas syringes to fill the total volume of the sample bottle with these two gases. The mixture was then vigorously stirred with a magnetic stirring bar for various times up to 1 h. The magnetic stirrer was then turned off and the sample bottle kept in ice for 2 min before removing the gas with a syringe needle for product analysis. After breaking the seal to the glass sample bottle, 3 µl of nitromethane was added to the solution to provide an internal stranded (IS) for quantitation of the products.

Before product analysis of the solution by GC, the solution was passed through a flash chromatography column (silica gel) to remove the metal complexes. GC analysis was performed on a HP6890 plus equipped with a flame ionization detector. The conditions were as follows: HP5 column (60 m×0.25 mm×0.25 mm film thickness); carrier gas, nitrogen at a flow rate of 1 ml/min; oven temperature, isothermal at 30° C.; pulsed splitless injection at 280° C., (25.0 psi for 30 sec and 17.5 psi for the rest of the acquisition time); and FID detector at 300° C. GC-MS analysis was carried out to identify the products on a HP6890 plus equipped with a HP5873 EI-MS detector.

The conditions were as follows: DB-1 MS column (60 m×0.25 mm×0.25 mm film thickness); carrier gas, helium at a flow rate of 1.3 ml/min; oven temperature, isothermal at 35° C.; split injection at 250° C. with split ratio 25:1.

$CH_4$: GC (isothermal, 30° C.), $t_R$=5.0 min; EI-MS, m/z (%) 16 (100) [M$^+$], 15 (70).

$CH_3OH$: GC (isothermal, 30° C.), $t_R$=5.5 min; EI-MS, m/z(%) 32 (80) [M$^+$], 31 (100), 29 (70).

Figure 28:
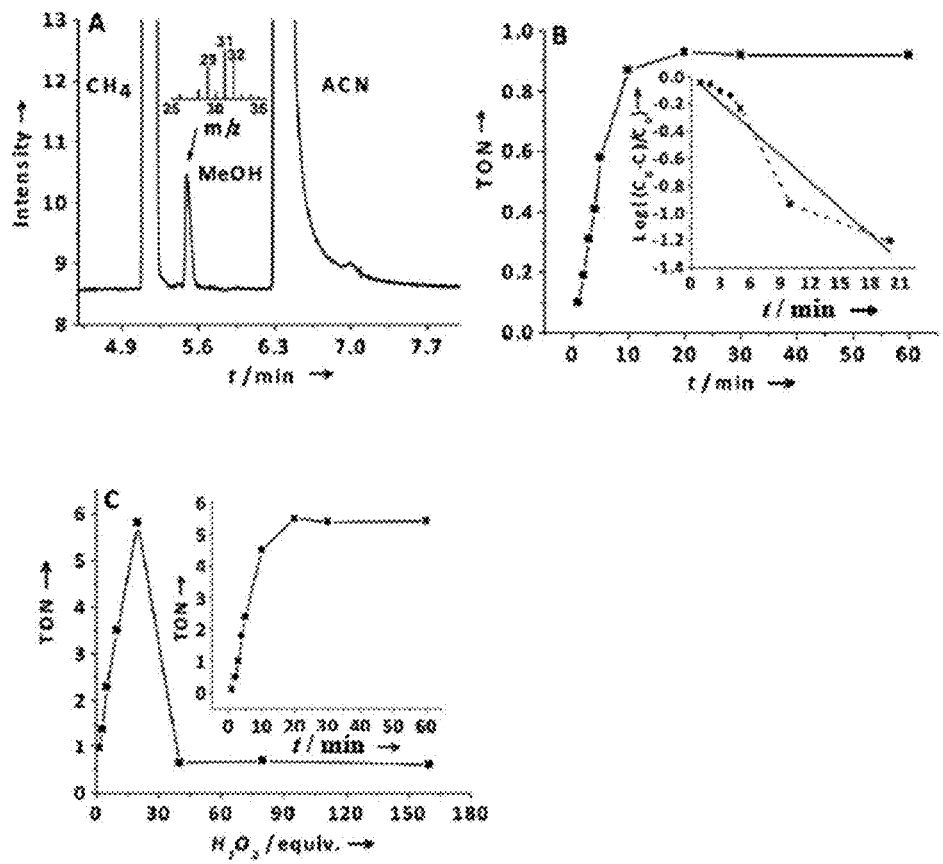
FIG. 28. Methane oxidation by $O_2$ mediated by the tricopper $Cu^{I}Cu^{I}Cu^{I}$(7-N-Etppz)1+ complex. A) Formation of methanol is analyzed by GC (retention time: 5.5 min); (inset): assignment of the product peak to $CH_3OH$ is verified by GC-MS comparing the mass distribution with that of a $CH_3OH$ standard. B) The time course of methane oxidation; (insert): pseudo first-order kinetic plot with rate constant $k_1=0.0646$ min$^{-1}$ ($C_0$ represents initial concentration of the fully reduced tricopper complex and C represents the concentration of methanol produced at any given time), with the best straight-line fit to the data. C) Catalytic turnover showing the TON as a function of the amounts of $H_2O_2$ (equiv.) added to regenerate the "spent" catalyst; (insert): time course of catalytic methane hydroxylation by multiturnovers of the tricopper complex in the presence of 20 equiv. of $H_2O_2$.

Product yields were calculated from corresponding standard curves prepared with authentic samples. The products collected from the gases and the solutions were combined to yield the TON. The results are depicted as a function of time of reaction in FIG. 28. This time-course study revealed that reaction was completed within 20 min with maximum TON of 0.92, indicating that the conversion of methane to methanol involved single turnover of the catalyst.

For multiple turnovers, $H_2O_2$ was used as the reductant to regenerate the "spent" catalyst. The above experiments were repeated in the presence of varying amounts of the reductant ranging from 5 to 160 equivalents using appropriate aliquots of 35% $H_2O_2$. These TONs are summarized in FIG. 28C.

Peptide synthesis. All the peptides were synthesized on a PS3™ automated peptide synthesizer (Rainin Instruments) by the batch fluorenylmethoxycarbonyl (Fmoc) polyamide method.[7] 0.1 mmol Rink amide AM resin, 0.4 mmol Fmoc-amino acid and 0.4 mmol PyBop (Merck Inc.) were used in the synthesis. The deprotection reagent and the activation reagent were 20% (v/v) piperidine in N,N-dimethylformamide (DMF) and 4.5% (v/v) N-methylmorpholine in DMF, respectively. The coupling reaction was checked by ninhydrin test. Usually it took ca. 2.0 h to complete the reaction. After synthesis, the resins were washed against DMF, ethanol and dichloromethane sequentially and dried in vacuum for 1.0 h.

The crude peptides were cleaved from resin in 93% trifluoroacetic acid (TFA) with 2.5% 1,2-ethanedithiol, 2.5% deionized (DI) water, 2.5% triisopropylsilane for 2.0 h. Side chain protecting groups included: Asp(OtBu), His(Trt), Thr (tBu), and Gln(Trt). The reaction mixtures then were filtered through a G3 funnel directly and the filtrate was added into 60 ml ice-cold t-butyl methyl ether.

Peptides were purified by HPLC. Reverse-phase HPLC was performed using an Ascentis® C18 HPLC column connected to a Waters-2695-Alliance HPLC system. A combination of two solvents was employed, both at a flow rate of 3 mL/min: binary gradients of solvent A (0.10% TFA, 5.0% MeCN, 95% DI water) and solvent B (0.10 TFA, 99.9% MeCN). Peptide concentrations were determined by UV spectroscopy (HP 8453 spectrophotometer) using the absorbance at 280 nm. The identities of the peptides were confirmed using ESI Finnigan LCQ MS (Thermo Finnigan, San Jose, Calif.). For the peptide HIHAMLTMGDWD, m/z=1424.6 (z=1).

All chemicals used in the preparation of the peptides were obtained from NovaBiochem unless stated otherwise.

Formation of the tricopper-peptide complexes. The peptide HIHAMLTMGDWD is capable of binding three copper ions to form both $Cu^ICu^ICu^I$- and $Cu^{II}Cu^{II}Cu^{II}$-peptide complexes in the presence of excess acetate (or chloride). When the $Cu^{II}Cu^{II}Cu^{II}$-peptide complex was formed in DI water, pH 6.8, in excess of 1 mM at a stoichiometric [$Cu^{II}$]/[peptide] concentration ratio of 3/1 and in the presence of the above anionic ligands, a blue acetate or chloride complex precipitated out of solution. The complex should be electrically neutral, as the six positive charges of the three $Cu^{II}$ ions are balanced by the six negative charges provided by the two Asps in the peptide sequence, the two acetate (or chloride) anionic ligands, and a capping "µ-oxo" (see main text). It had only limited solubility (~1 mM) in aqueous buffer and dissociated into copper-peptide species of lower copper nuclearity. The white $Cu^ICu^ICu^I$-peptide complex was readily formed by incubating a sample of the blue $Cu^{II}Cu^{II}Cu^{II}$-peptide precipitate formed from a stoichiometric $Cu^{II}$/peptide solution ([$Cu^{II}$]/[peptide] concentration ratio of 3/1) using $Cu(OAc)_2$ with 6 equivalents of ascorbate, followed by washing. The reduced tricopper-peptide complex was totally insoluble in aqueous buffer.

Mass spectroscopic analysis of the $Cu^{II}Cu^{II}Cu^{II}$-peptide solution. Mass spectroscopic analysis of the copper-peptide solution was undertaken on a 7.0 Tesla FT ICR mass spectrometer (APEX IV, Bruker-Daltonics) operating in the ESI mode. The copper-peptide complex was formed by mixing 3.0 mM peptide with 9.0 mM $Cu(OAc)_2$ in deionized water containing 0.05% formic acid (pH 4.0). The solution was then centrifuged in a Quickspin centrifuge to separate the solution from the solid tricopper complex precipitate formed. 50 μL 1:1 H$_2$O/CH$_3$OH (1:1 v/v) solution containing 0.05% formic acid (pH ~4) was then added to 6.0 μL of the supernatant and the mass spectrum of the copper-peptide species in the solution was recorded.

Figure 22:
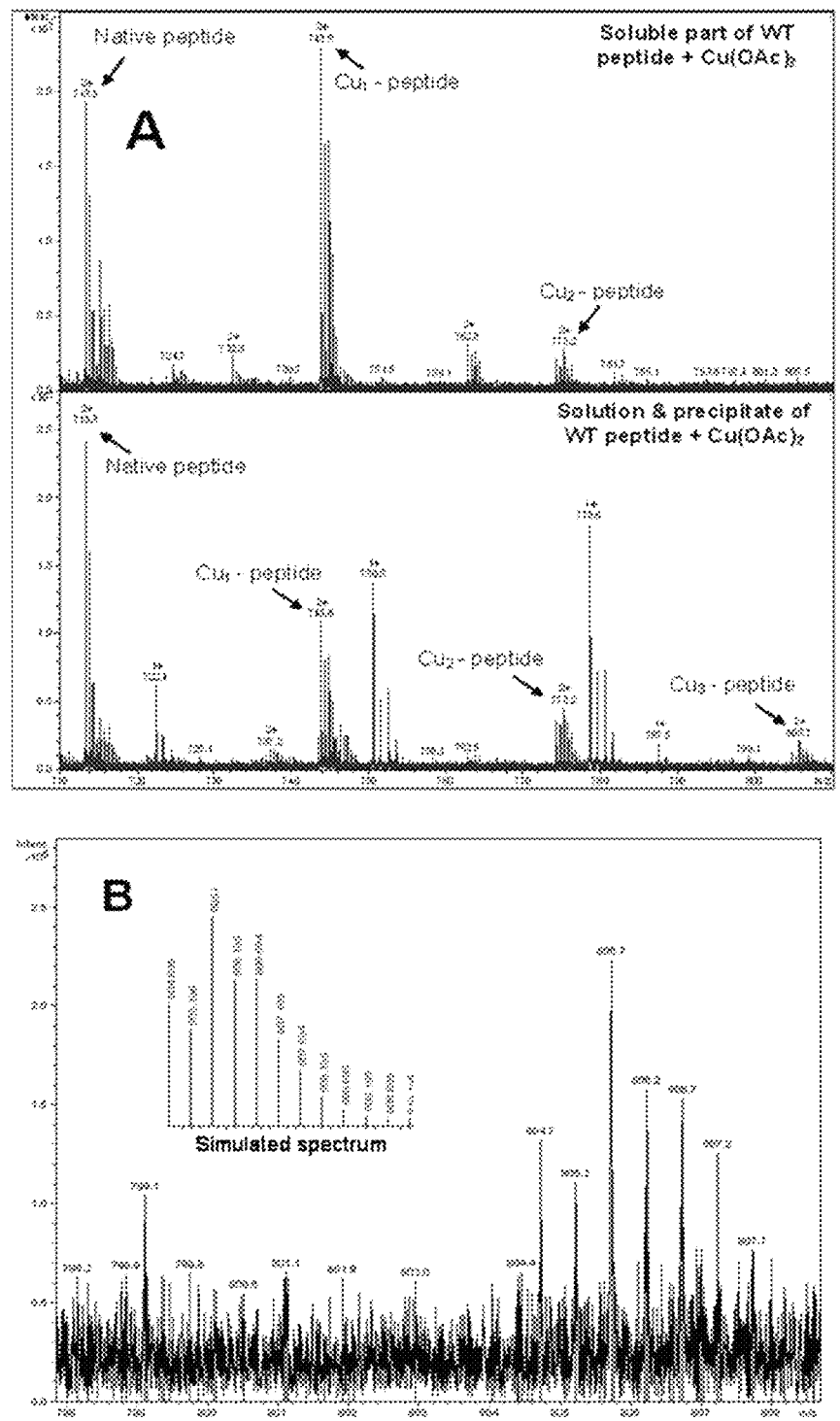
FIG. 22. A) FT-ICR ESI-MS of the copper complexes formed with the HIHAMLTMGDWD peptide and Cu(OAc)$_2$. Upper panel: copper peptide species formed in solution; lower panel: copper peptide species observed in solution as well as in the precipitate. Native peptide: m/z 713.3 (z=2); Cu$_1$-peptide: m/z 743.8 (z=2); Cu$_2$-peptide: m/z 775.2 (z=2); and Cu$_3$-peptide: m/z 805.7 (z=2). B) Simulation of the mass cluster arising from the Cu$^{II}$Cu$^{II}$Cu$^{II}$ complex with the HIHAMLTMGDWD peptide at m/z 805.7 (z=2), including the $^{63}$Cu and $^{65}$Cu isotopes at natural abundance ($^{63}$Cu 69.17%; $^{65}$Cu 30.83%), and comparison with experiment.

Based on mass spectrometry, we found that the peptide HIHAMLTMGDWD was capable of binding three Cu$^{II}$ ions to form a tricopper complex in the presence of excess acetate (or chloride). Formation of the Cu$_3$-peptide species was confirmed by FT-ICR ESI-MS (FIG. 22A). Mass peaks from the native peptide (m/z 713.3 (z=2)), the Cu$_1$-peptide (m/z 743.8 (z=2)), and the Cu$_2$-peptide (m/z 775.2 (z=2)) were obtained from the solution. An additional mass peak (m/z 805.7 (z=2)) was discerned when the precipitate was included with the solution in the ESI-MS analysis. This mass peak is readily assigned to the Cu$_3$-peptide species. Simulation of the mass cluster in the vicinity of the m/z 805.7 (z=2) peak by including the statistical distribution of $^{63}$Cu and $^{65}$Cu isotopes confirms the assignment to the tricopper-peptide complex.

Figure 29:
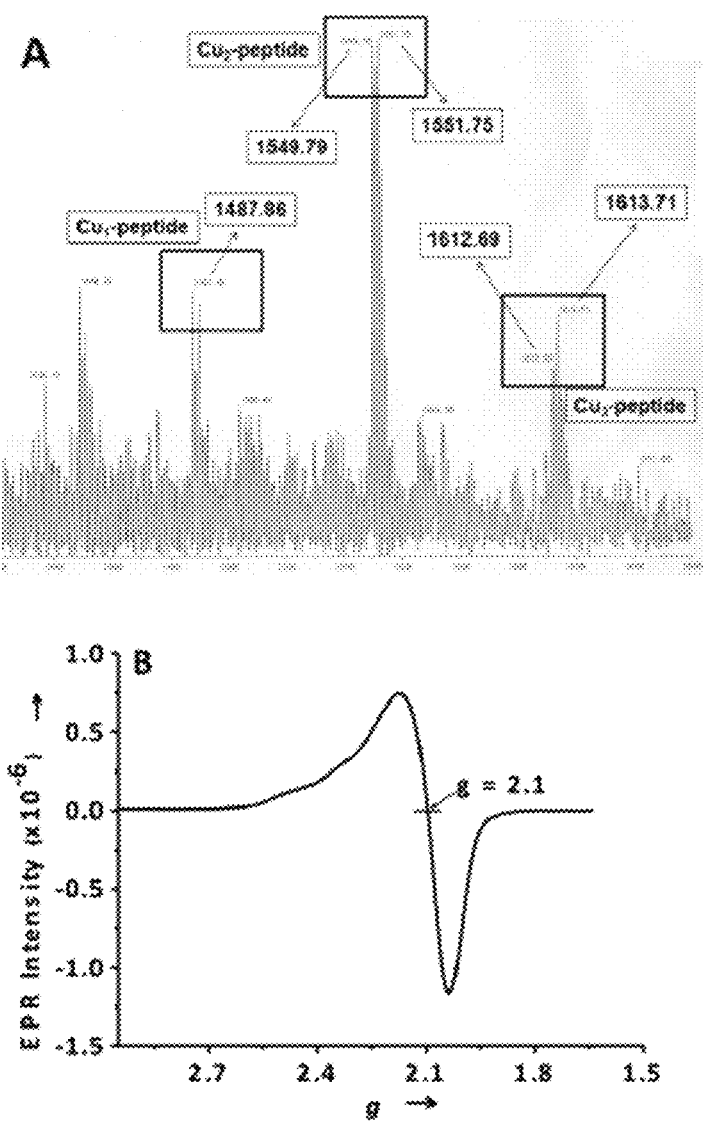
FIG. 29. Characterization of the tricopper-peptide complex. A) FAB MS of solid $Cu^{I}Cu^{I}Cu^{I}$-peptide complex. The mass cluster associated with the $Cu_3$-peptide complex has been highlighted. B) 77K EPR spectrum of the $Cu^{II}Cu^{II}Cu^{II}$-peptide complex. The blue precipitate has been dispersed in KCl (1% by weight) for EPR measurements.

FAB mass spectrometry of the solid Cu$^I$Cu$^I$Cu$^I$-peptide complex. Fast atom bombardment mass spectrometry (FAB-MS) of the solid Cu$^I$Cu$^I$Cu$^I$-peptide complex formed with HIHAMLTMGDWD revealed a mass peak at m/z 1613.7 (z=1), consistent with a Cu$_3$-peptide species (FIG. 29A). The corresponding 2:1 and 1:1 copper-peptide species were observed at m/z 1549.8-1551.8 (z=1), and m/z 1489 (z=1), respectively. FAB mass spectra were obtained on a JMS-700 double-focusing mass spectrometer (JEOL, Tokyo, Japan) with a resolution of 8000(3000) (5% valley definition). A Xe gun was used operating at the source accelerating voltage of 10 kV, and 3-nitrobenzyl alcohol (NBA) was used as the matrix to support the solid tricopper-peptide complex. Samples were prepared by manual mixing of the Cu$^I$Cu$^I$Cu$^I$-peptide complex with 1 ml of NBA, and an aliquot of the mixture was applied to the target tip for the FAB mass analysis. Mass spectra were recorded in a 32 s scan from m/z 500 to 1800.

Identity of Ligands. The peptide HIHAMLTMGDWD provides the bulk of the potential metal-ligating residues of the PmoA fragment that we have previously used to build the tricopper cluster into the D site of the crystal structure of pMMO from *Methylococcus capsulatus* (Bath).[8] The residues highlighted in bold in the peptide sequence correspond (from left to right) to His38, Met42, Asp47, and Asp49 of PmoA. To identify the ligands involved in the formation of the tricopper-peptide complexes in this study, we have prepared a number of peptide mutants and developed a simple assay based on the precipitation properties of the Cu$^{II}$Cu$^{II}$Cu$^{II}$-peptide complex. The use of the first His and the first Met in the peptide sequence to mimic His38 and Met42, and the C-terminal Asp to mimic Asp49, in the model tricopper complex was corroborated by amino acid substitutions, as shown in Table 8. These highlighted amino acids were found to be absolutely required for the formation of the tricopper cluster. A much weaker complex was formed when the leading His in the peptide sequence was substituted by Gln. When this His was substituted by Ala, only a trace amount of precipitate was detected. Similarly, replacement of the first Met in the peptide sequence by Ala abolished formation of the tricopper complex. In contrast, replacement of the second His in the peptide sequence by Gln, or the second Met in the peptide sequence by Ala, had little effect on the formation of the tricopper complex. The remaining Asp in the peptide was intended to mimic Asp47, and substitution of this Asp by Ala led only to the formation of a weak complex.

TABLE 8

Formation of Cu$^{II}$Cu$^{II}$Cu$^{II}$-peptide complexes from solutions of peptides and Cu(OAc)$_2$, [Cu(II)]/[Peptide] concentration ratio = 3.

| Peptide Sequence | Corresponding pMMO mutation* | Complex Formation |
|---|---|---|
| HIHAMLTMGDWD | Wild type | normal |
| QIHAMLTMGDWD | H38Q | inhibited |
| AIHAMLTMGDWD | H38A | strongly inhibited |
| HIQAMLTMGDWD | H40Q | normal |
| HIHAALTMGDWD | M42A | not detected |
| HIQAALTMGDWD | H40Q M42A | not detected |
| HIHAMLTAGDWD | M45A | normal |
| HIQAMLTAGDWD | H40Q M45A | normal |
| HIHAMLTMGAWD | D47A | inhibited |
| HIHAMLTMGDWL | D49L | not detected |

EPR spectroscopy of the solid tricopper-peptide complexes. The solid Cu$^{II}$Cu$^{II}$Cu$^{II}$-peptide complexes were prepared by precipitation from 1-5 mM peptide solutions (in deionized water, pH 6.8), upon the addition of three equivalents of Cu(OAc)$_2$ or CuCl$_2$. The concentration of the peptide sample was determined spectrophotometrically at 280 nm using ε=5690 M$^{-1}$ cm$^{-1}$. In each case, the Cu$^{II}$ solution was slowly trickled down into the peptide solution in a shaker. The blue precipitates were dispersed in KCl (1% by weight) for EPR measurements.

Figure 23:
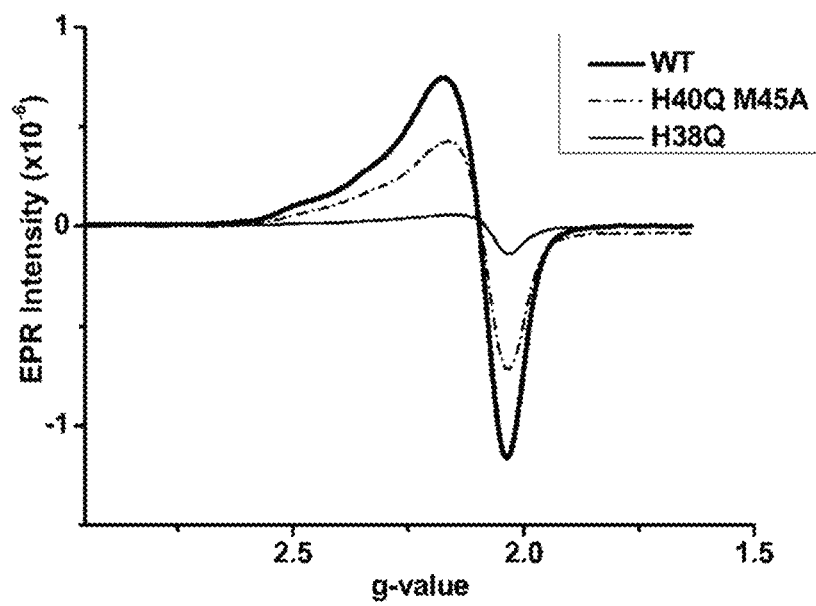
FIG. 23. 77K EPR spectra of several tricopper-peptide complexes. The Cu$^{II}$Cu$^{II}$Cu$^{II}$-cluster EPR signal was observed for the tricopper-peptide complexes formed with the wild-type peptide HIHAMLTMGDWD (———) and the H400 M45A mutant peptide HIQAMLTAGDWD (— ■ —). A weak signal with altered line shape was discerned for the H38Q mutant peptide QIHAMLTMGDWD (_____). The blue precipitates were dispersed in KCl (1% by weight) for EPR measurements.

77K EPR spectra of the tricopper-peptide complexes (FIG. 23 and FIG. 29B) were recorded on a Bruker EMX spectrometer equipped with a Bruker TE102 cavity. The sample temperature was maintained at 77K by using a liquid-nitrogen finger dewar. Microwave frequency: 9.490-9.516 GHz; microwave power: 2.0 mW; modulation amplitude: 3 Gauss.

4K EPR measurements on the blue (Cu$^{II}$Cu$^{II}$Cu$^{II}$) and white (Cu$^I$Cu$^I$Cu$^I$) precipitates dispersed in KCl (3% by weight) were performed on a Bruker E580 spectrometer equipped with a Bruker TE102 cavity. The sample temperature was maintained near 4K by an Oxford Instruments continuous liquid-helium cryostat. Microwave frequency: 9.45-9.66 GHz; microwave power: 20 mW; modulation amplitude: 1 Gauss.

The reduced tricopper-peptide complex should be EPR silent. Intensity comparison of the 4K EPR spectra recorded for matched samples of the white Cu$^I$Cu$^I$Cu$^I$-peptide and the blue Cu$^{II}$Cu$^{II}$Cu$^{II}$-peptide precipitates (3% by weight dispersed in KCl) indicated that the residual oxidized tricopper cluster observed in the Cu$^I$Cu$^I$Cu$^I$-peptide sample accounted for less than 1% of the total tricopper clusters in the sample.

Evidence for a copper triad. The Cu$^{II}$Cu$^{II}$Cu$^{II}$-peptide complexes exhibited the featureless almost isotropic electron paramagnetic resonance (EPR) signal expected for a triad of Cu$^{II}$ spins that are ferromagnetically coupled to give the S$_T$=3/2 ground state, as previously reported for pMMO-enriched membranes and pMMO isolated from *Methylococcus capsulatus* (Bath) containing the full complement of ~15 copper ions.[9,10] 77K EPR spectra of the complexes formed with the wild-type and H40Q M45A peptides, namely, HIHAMLTMGDWD and HIQAMLTAGDWD, are presented in FIG. 23. The g-value observed for both complexes is 2.1, which matches well the g-value reported for the putative tricopper cluster in the purified active pMMO.[10] EPR intensity measurements on a weighed amount of the dried precipitate of the copper-peptide complex dispersed 1% in KCl indicated that the $Cu^{II}$ content in the precipitate is totally accounted for by the $Cu^{II}Cu^{II}Cu^{II}$-peptide complex within experimental error. The corresponding tricopper-cluster content in the H400 M45A peptide-complex precipitate was ~80%. Only a weak EPR signal (with an altered lineshape) is discerned in the case of the mutant H38Q peptide QIHAMLTMGDWD. These EPR results provide a direct link between the wild-type tricopper-peptide complex that we have prepared here with the putative tricopper cluster that has been implicated at the D site in the pMMO enzyme.

Figure 24:
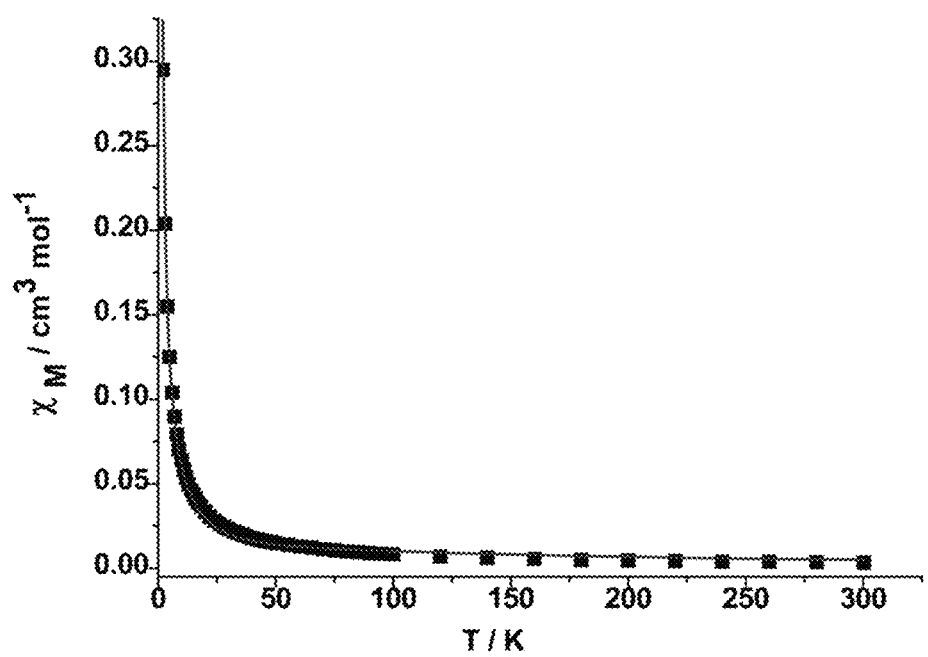
FIG. 24. Temperature dependence of the molar susceptibility determined for the Cu$^{II}$Cu$^{II}$Cu$^{II}$-HIHAMLTMGDWD complex: black filled square, experimental data; red full line, the best fit of the data to the $\chi_M$ derived for an equilateral triad of $Cu^{II}$ spins with a $S_T=3/2$ ground state with an exchange interaction J of 35.4 cm$^{-1}$.

The assignment of the observed EPR to the $S_T=3/2$ ground state of a triad of ferromagnetically coupled $Cu^{II}$ spins was confirmed by magnetic susceptibility measurements on the wild-type $Cu^{II}Cu^{II}Cu^{II}$-peptide complex (FIG. 24).

Magnetic susceptibility measurements. Magnetic susceptibility of the $Cu^{II}Cu^{II}Cu^{II}$-HIHAMLTMGDWD complex was measured using a superconducting quantum interference device vibrating sample magnetometer (SQUID VSM, from Quantum Design). The precipitate of the peptide containing 3 equivalents of $Cu^{II}$ was dried and packed into a gelatin capsule. Temperature-dependent magnetization (bulk magnetic moment) data were collected over the temperature range of 1.8-300 K and at a magnetic field strength of 1.0 Tesla.

The paramagnetic component of the bulk magnetic moment was obtained by subtracting the diamagnetic contribution of the $Cu^{II}Cu^{II}Cu^{II}$-peptide complex and the sample holder from the observed bulk magnetic moment. The molar magnetic susceptibility ($X_M$) was calculated from this corrected magnetic moment value. The plot of $X_M$ versus T is presented in FIG. 24. Best fit of the magnetic susceptibility data to the $X_M$ derived for an equilateral triad of $Cu^{II}$ spins with a $S_T=3/2$ ground state yields an exchange interaction J of 35.4 cm$^{-1}$. ($H_{exchange}=-2$ J $[S_A \cdot S_B + S_B \cdot S_C + S_C \cdot S_A]$; see Data Analysis for details). The temperature dependence of the magnetic susceptibility indicates that the two $S_T=1/2$ doublet states are ca. 100 cm$^{-1}$ above the quartet ground state.

Cloning, protein expression, and purification of TEL-SAM-PmoA(38-49) fustion protein. The plasmid harboring the gene for the wild-type TEL-SAM domain[11] was generously provided by Dr. James Bowie (UCLA). The PmoA sequence (residues 38-49) of *Methylococcus capsulatus* (Bath) plus a C-terminal Pro-Asp was fused to the His-Ile residues near the C-terminus of the TEL-SAM domain by incorporating the corresponding nucleotide sequence into the primer. The resulting amplicon was cloned into the NdeI restriction site of the pET28b(+) vector (Novagen) so as to produce the target protein with an N-terminal His$_6$ tag. Site-directed mutagenesis (Stratagene) was performed to produce the V80E mutation necessary for the pH dependent polymerization of the TEL-SAM protein. The integrity of the plasmid was verified by DNA sequencing. The plasmids encoding the His$_6$-tagged TEL-SAM V80E mutant/PmoA (38-49)+PD fusion protein (TEL-SAM-PmoA(38-49)) were then transformed into *E. coli* BL21 (DE3)[pLysS] cells (Stratagene). Expression of the fusion protein was induced with 1 mM IPTG. Cells were grown at 37° C. for 5 h in Lauria-Bertani (LB) broth containing 50 mg/L kanamycin to an OD$_{600}$ of ~0.6. The 1-L cell culture was pelleted at 4000×g for 30 min.

The cell pellet was re-suspended in 20 mM Tris-HCl, 200 mM NaCl, 30 mM imidazole, and lysed by sonication. The crude cell extract was centrifuged at 18,000×g for 30 min at 4° C. The supernatant was loaded on to a 5-mL bed volume Ni-activated HisTrap HP column (GE Healthsciences) and eluted with an imidazole gradient (10-500 mM) in 20 mM Tris-HCl and 200 mM NaCl. The His$_6$-tagged TEL-SAM-PmoA(38-49) fusion protein eluted at approximately 120 mM imidazole. The elution was diluted with 20 mM Tris-HCl to reduce the imidazole and NaCl concentrations to less than 20 mM. The diluted elution was then applied to a 5-mL HiTrap Q anion exchange column (GE Healthsciences), washed with 20 mM Tris-HCl and 25 mM NaCl, and eluted with a gradient from 20 mM to 1 M NaCl. The fusion protein eluted at approximately 430 mM NaCl and was greater than 95% pure by SDS-PAGE and Coomassie staining. The purified protein was dialyzed overnight into 20 mM Tris-HCl and 200 mM NaCl, and concentrated using a Vivaspin concentrator. The His$_6$-tag was removed by overnight thrombin digestion and the protein concentration was determined by the Bradford method.

The purified TEL-SAM-PmoA(38-49) fusion protein was characterized by MALDI-TOF/MS. The copper complex formed with TEL-SAM-PmoA(38-49) fusion protein was also prepared and subjected to MALDI-TOF/MS and EPR measurements, and subsequently, X-ray Cu K-edge absorption and EXAFS studies.

MALDI-TOF/MS of the copper complex formed with the TEL-SAM-PmoA(38-49) fusion protein. Matrix assisted laser desorption/ionization time-of-flight (MALDI-TOF) spectroscopic studies of the TEL-SAM-PmoA(38-49) were carried out at the CCIC Mass Spectrometry and Proteomics Facility at Ohio State University, Columbus, Ohio. MALDI-TOF/MS of the TEL-SAM-PmoA(38-49) fusion protein in the presence of 5.4 equivalents of $Cu(OAc)_2$ was performed on a Bruker Reflex III (Bruker, Breman, Germany) mass spectrometer operated in linear, positive ion mode with a $N_2$ laser. Laser power was used at the threshold level required to generate signal. Accelerating voltage was set to 28 kV. The instrument was calibrated with protein standards bracketing the molecular weight of the protein (typically mixtures of apo-myoglobin and bovine serum albumin) using doubly charged, singly charged and dimer peaks as appropriate. Samples were prepared in 0.1% TFA at an approximate concentration of 50 pmol/μL. Sinapinic acid was used as the matrix for proteins prepared as a saturated solutions in 50% ACN/0.1% TFA (in water). Allotments of 1 μL of matrix and 1 μL of sample were thoroughly mixed together; 0.5 μL of this was spotted on the target plate and allowed to dry.

Figure 25:
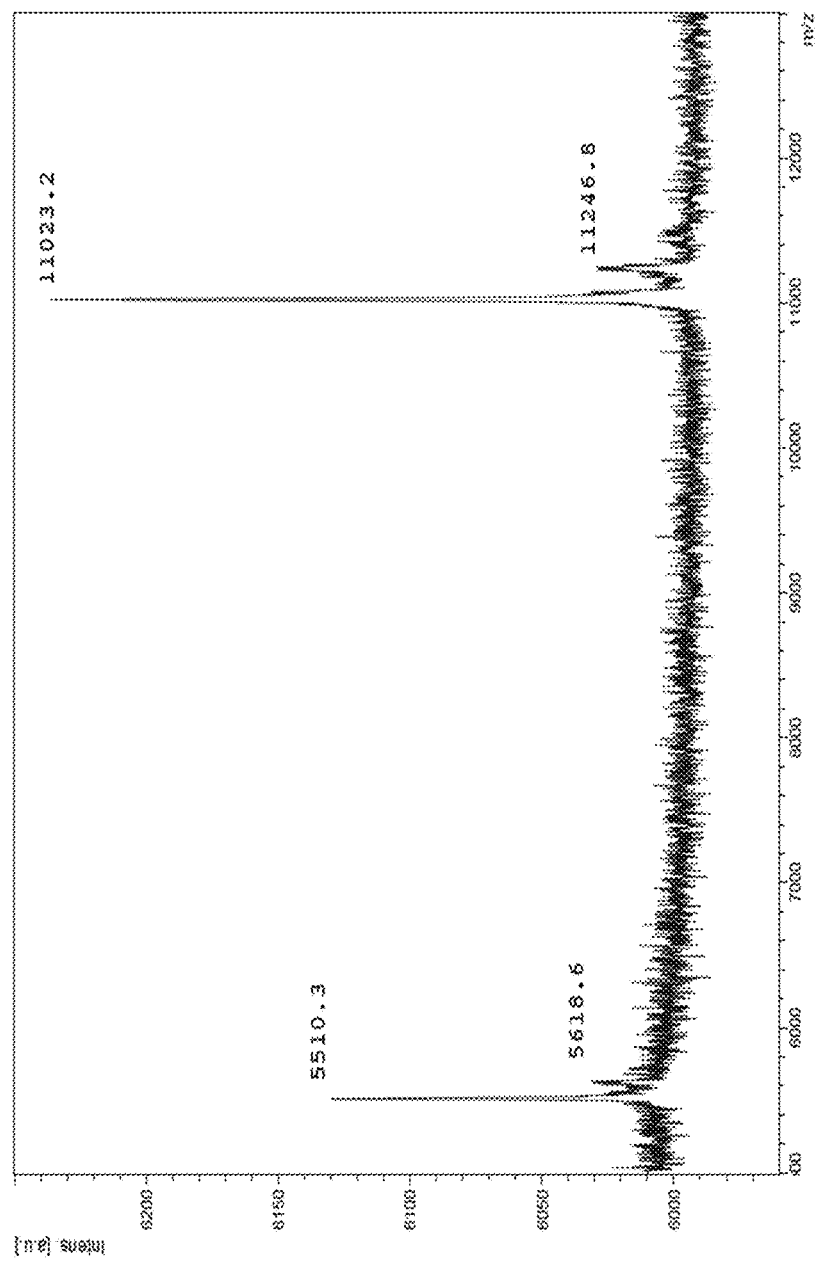
FIG. 25. MALDI-TOF-MS of the tricopper complex of TEL-SAM-PmoA(38-49) fusion protein in the presence of 5.4 equivalents of $Cu(OAc)_2$.

The MALDI spectrum revealed a primary mass of 11,023.2 Da that is in close agreement to the expected molecular mass of the protein, 11,027.3 Da (FIG. 25). A second peak was observed at 11,246.8 Da. Notably, the 224 Da mass difference between these peaks would be consistent with the binding of a trinuclear copper dioxo or oxo-hydroxo bridged species bound to the TEL-SAM-PmoA(38-49) fusion protein.

X-ray absorption measurements. The sample of the tricopper complex formed with the TEL-SAM-PmoA(38-49) fusion protein for X-ray absorption spectroscopy (XAS) was prepared as follows: 0.9 M TEL-SAM-PmoA(38-49) fusion protein was precipitated with 9 equivalents of copper acetate. The protein pellet was washed extensively with double-distilled $H_2O$.

Figure 30:
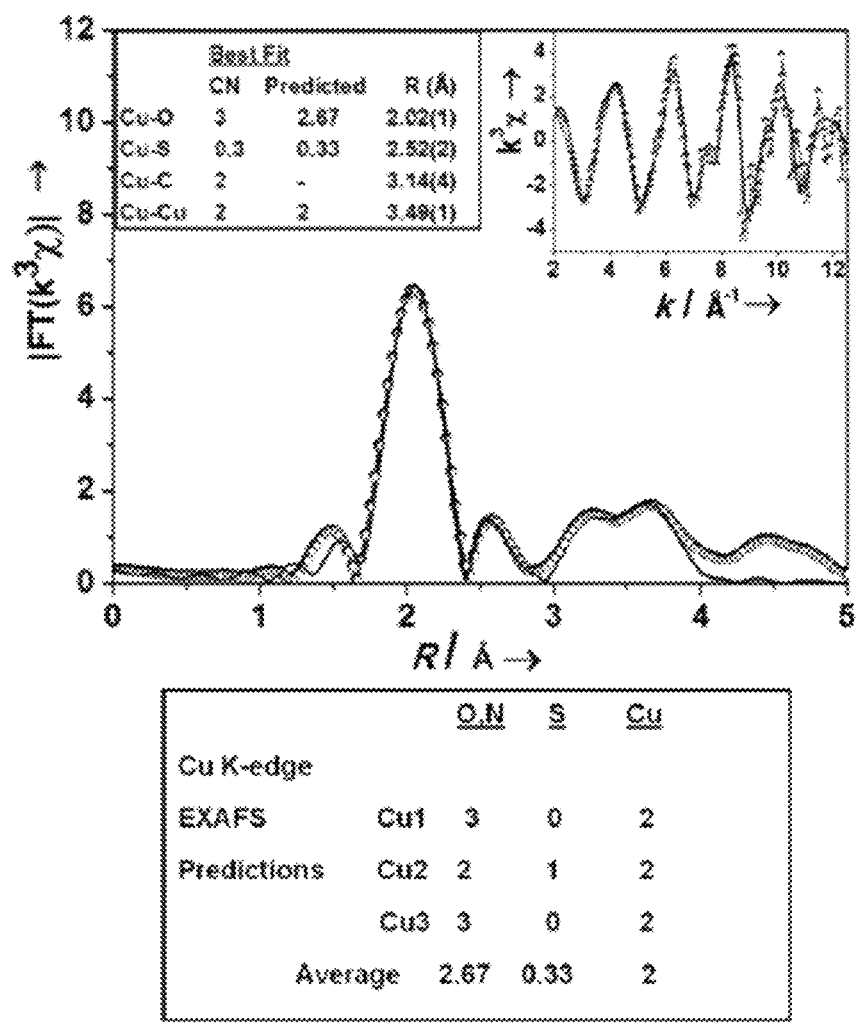
FIG. 30. Cu K-edge EXAFS observed for the TEL-SAM-PmoA(38-49) fusion protein with the peptide sequence HIHAMLTMGDWDPD together with the best fit of the ligand structure for the tricopper cluster (left inset). Right inset shows the fitted $k^3\chi(k)$ data. The average coordination numbers (CN) predicted from the ligand structure are also shown.

X-ray absorption measurements of the tricopper-complex powders were performed at the wiggler beamline BL-17C1 in the National Synchrotron Radiation Research Center in Hsinchu, Taiwan. The beam was monochromatized with a double crystal monochromator of Si(111) for energy resolution $\Delta E/E \approx 2 \times 10^{-4}$. The $Cu^{II}Cu^{II}Cu^{II}$-peptide sample was sealed in a polyethylene bag and measured at ~278 K controlled by a gas cooling stream. The $Cu^I Cu^I Cu^I$-peptide complex was prepared in a dry $N_2$-filled glove box, sealed, and placed in sample holder maintained at 100K by a DE-202G closed-loop-cycle cryocooler (Advanced Research Systems, Inc.). Absorption spectra were taken in the fluorescence mode with a 13-element solid-state detector in the energy range from 8779 to 9876 eV. The first inflection point at 8979.0 eV of the absorption spectrum of a Cu foil was used for energy calibration. Previously, a slightly higher value of 8980.3 eV was used by Kau et al.[12] Data collection strategy was the same as previous reported by Li et al.[13] Reproducible XANES spectra for all 10 scans indicated that radiation damage to the protein structure was negligible. The XAS data were corrected for background and normalized according to $X(k)=[\mu(k)-\mu_0(k)]/\Delta\mu_0(0)$ by the AUTOBK program[14] with $\mu(k)$ for the measured absorption coefficient, $\mu_0(k)$ for the background, and $\Delta\mu_0(0)$ for the edge jump. The value of the wave vector k is defined as $k=[2m(E-E_0)/\hbar]^{1/2}$, where E is the photon energy, $E_0$ the threshold energy, $\hbar$ the Planck constant, and m the mass of electron. Based on the local maxima of the first-derivative profiles of the XANES spectra, $d\mu/dE$, $E_0$ was set at 8990.8 eV. The $X(k)$ in the EXAFS region $2.55 \leq k \leq 12.25$ Å$^{-1}$ was further weighted by $k^3$ and then Fourier-transformed into the R-space as $FT[k^3 \chi(k)]$ (FIG. 30).

Figure 26:
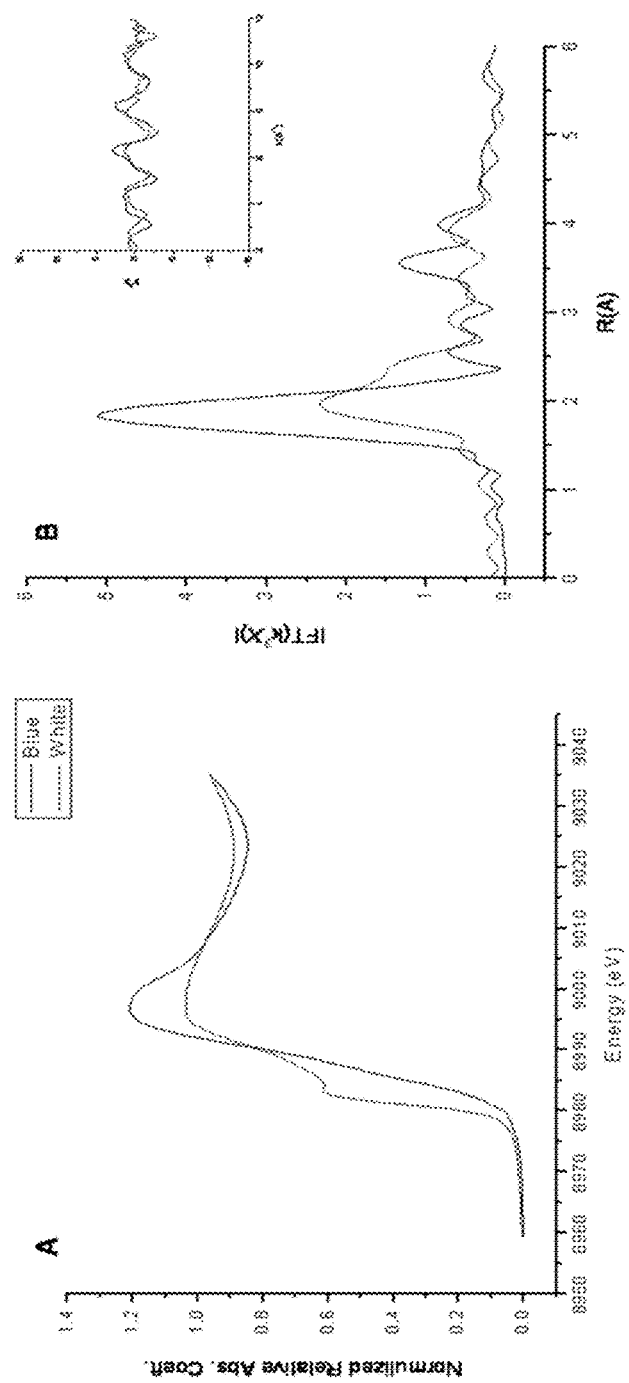
FIG. 26. Comparison of the XANES (panel A) and EXAFS (panel B) between precipitates of the blue solid $Cu^{II}Cu^{II}Cu^{II}$-peptide and the white $Cu^{I}Cu^{I}Cu^{I}$-peptide complexes (wild-type peptide). The measurements on the blue precipitate were performed at 277K. The white precipitate was prepared in a dry $N_2$-filled glove box, sealed, and placed in sample holder maintained at 100K. The spectra are the accumulation of 15 scans.
Figure 27:
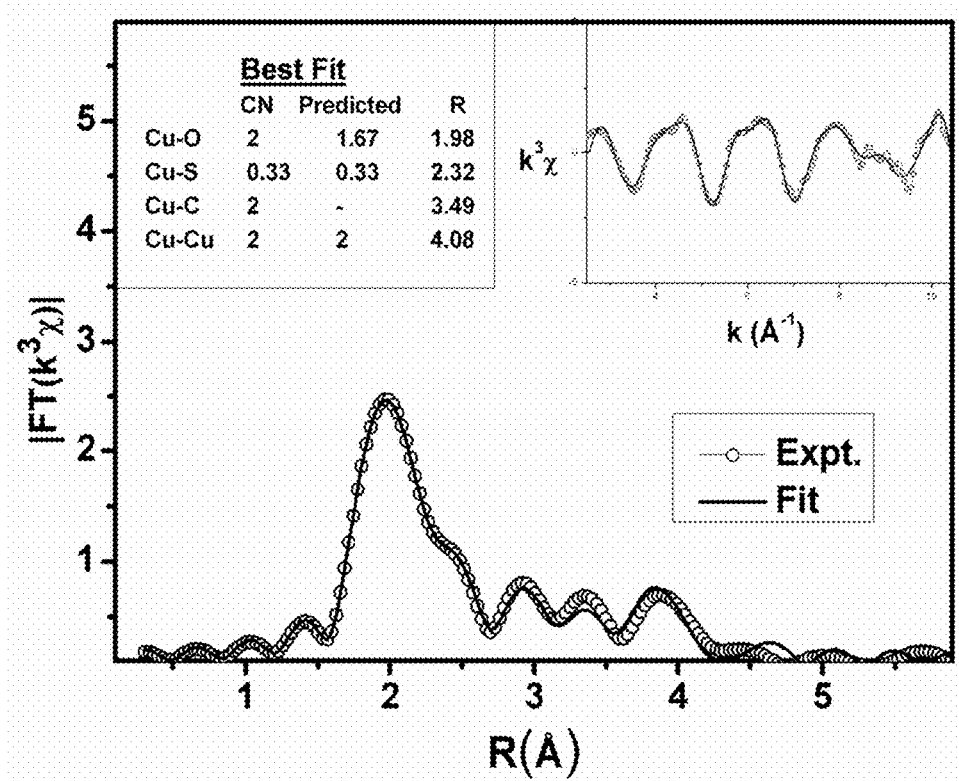
FIG. 27. Fourier transformed amplitudes $FT[k^3\chi(k)]$ (open circles) and the fitted (solid curves) of the $Cu^{I}Cu^{I}Cu^{I}$ complex with the HIHAMLTMGDWD peptide together with the best fits of the ligand structure for the tricopper cluster. Inset shows the fitted $k^3\chi(k)$ data. The coordination numbers of the atom types inferred from fitting of the EXAFS data are also compared with the coordination numbers expected from the tricopper cluster model rebuilt into the D site of the crystal structure.[8] The goodness-of-fit factor $R_{fit}$ was 0.3%.

The XANES spectra of the $Cu^{II}Cu^{II}Cu^{II}$- and $Cu^I Cu^I Cu^I$-complexes with the wild-type peptide are compared in FIG. 26A. An obvious peak at ~8982 eV in the spectrum of the reduced complex signifies the allowed 1s→4p transition[12] for $Cu^I$. The EXAFS spectra of these copper complexes are compared in FIG. 26B. Analysis and data fitting of the EXAFS spectrum of the $Cu^I Cu^I Cu^I$-complex with the wild-type peptide is shown in FIG. 27.

Preparation of the mesoporous-carbon supported $Cu^I Cu^I Cu^I$-peptide complex. All experiments were carried out in a glovebox (Coy Lab) with the $O_2$ level below 1 ppm as determined by Oxygne and Hydrogen Analyzer (Coy Laboratory Products, Grass lake, Mich.). Mesoporous carbon (Sigma Aldrich, pore size >0.2 cm$^3$/g mesoporosity; 80 mg) was suspended with 1 ml of the 12mer peptide (7.1 mg, 5 mM) in DI water in a 2 ml Eppendorf tube at 4° C. overnight. The adsorbed peptide or encapsulated by the mesoporous carbon was collected by centrifuging at 13000 rpm for 30 min. After delicately removing the supernatant by using a pipetman, the peptide associated with the mesoporous carbon was treated with 25 mM $CuCl_2$ solution (1 ml) and suspended at 4° C. for 2 days. The sample was then centrifuged at 13000 rpm for 30 min to collect the pellet. After removing the supernatant, the pellet was washed twice with $H_2O$ to remove copper ions that were not complexed with the peptide. 77K EPR confirmed that all the copper ions bound to the peptides associated with the mesoporous carbon were in the form of ferromagnetically coupled $Cu^{II}$ triads. The $Cu^{II}Cu^{II}Cu^{II}$-peptide complexes encapsulated in the mesoporous carbon mixture were then reduced to the $Cu^I Cu^I Cu^I$-peptide species by treatment with 1 ml 25 mM ascorbate solution for 20 min. This ascorbate reduction was repeated one more time before the pellet was twice washed by 1 ml of degassed double-distilled $H_2O$ to remove the dehydro-ascorbate and excess ascorbate. After washing, the mesoporous carbon-supported $Cu^I Cu^I Cu^I$ tricopper-peptide complexes were collected by centrifuging at 13000 rpm for 30 min and the supernatant decanted. Finally, the pellet was dried for 3 days in a desiccator by using anhydrous calcium chloride as the moisture scavenger. No EPR signals were detected for these pellets at 77K indicating that the copper ions were fully reduced in the sample.

Activity assays of the mesoporous-carbon supported $Cu^I Cu^I Cu^I$ tricopper-peptide complexes. Activities of the $Cu^I Cu^I Cu^I$ tricopper-peptide complexes were determined by both the propylene epoxidation and methane oxidation assays. All assays were performed in 9-mL closed vials at 45° C. under a water bath. In the case of the propylene epoxidation activity, the mesoporous-carbon supported tricopper complexes were sealed in 9-ml vials and evacuated. 6 ml propylene at STP (249 µmol) and 3 ml of oxygen at STP (124 µmol) were sequentially introduced into the vials under atmospheric pressure using a syringe needle to initiate the assay. In the case of the methane oxidation activity, the tricopper-peptide complexes encapsulated in the mesoporous-carbon were sealed in 9-ml vials and evacuated for 20 sec, and 6 ml methane at STP (249 µmol) and 3 ml of oxygen at STP (124 µmol) were sequentially introduced into the vials under atmospheric pressure to initiate the assay. GC and GC-MS analyses of the oxidation products were performed with the conditions described earlier for the model tricopper complex.

$CH_4$: GC (isothermal, 30° C.), $t_R$=5.0 min; EI-MS, m/z (%) 16 (100) [M$^+$], 15 (70).

$CH_3OH$: GC (isothermal, 30° C.), $t_R$=5.5 min; EI-MS, m/z(%) 32 (80) [M$^+$], 31 (100), 29 (70).

$C_3H_6$: GC (isothermal, 30° C.), $t_R$=5.0 min; EI-MS, m/z(%) 42 (70) [M$^+$], 41 (100), 39 (80).

$C_3H_6O$: GC (isothermal, 30° C.), $t_R$=6.1 min; EI-MS, m/z(%) 58 (100) [M$^+$], 43 (70), 28 (70).

Quantitation was performed using standard curves generated by analyzing propylene oxide and methanol standards (Merck; spectrophotometric grade >99%).

Data Analysis

Analysis of the magnetic susceptibility data. The isotropic exchange of three $S_A=S_B=S_C=\frac{1}{2}$ centers forming an equilateral triad will result in a quartet ($^4$A) and doubly degenerate doublets ($^2$E).[15] For the ferromagnetic exchange (J>0) the quartet $^4$A is the ground state, whereas for the anti-ferromagnetic interaction (J<0) the ground state will be the doublets $^2$E. However, in the latter situation, Jahn-Teller distortion of the triad is expected to occur to alleviate spin frustration. The simple isotropic exchange Hamiltonian can be written as $$H_{isotropic\ exchange} = -2\ J[S_A \cdot S_B + S_B \cdot S_C + S_C \cdot S_A], \quad (1)$$

and the mean molar magnetic susceptibility ($X_M$) is given by the well-known van Vleck equation:

$$\bar{\chi}_M = \left[\frac{N_A \mu_0 \mu_B^2 g_{Cu}^2}{4 k_B T}\right] \frac{1 + 5\exp(3J/k_B T)}{1 + \exp(3J/k_B T)} \quad (2)$$

where $N_A$ is Avogadro number; $\mu_0$, permittivity; $\mu_B$, the Bohr magneton; and $k_B$ is the Boltzmann constant. $g_{Cu}$ denotes the average g value of the $Cu^{II}$ ion, and J is the isotropic exchange interaction.

Analysis of EXAFS data. Based on the plane wave single scattering, the general EXAFS formula can be expressed as a summation over all shells j by the following equation, $$\chi(k) = S_0^2 \sum_j \frac{N_j(k) F_j(k)}{k R_j^2} \sin[2kR_j + \delta_j(k)] e^{-2k^2 \sigma_j^2} \quad (3)$$

where $F_j(k)$ is the backscattering amplitude from each of the $N_j$ atoms in the shell at distance $R_j$ (relative to the absorbing atom), $\exp(-2k^2\sigma_j^2)$ is the Debye-Waller factor with the mean-squared displacement $\sigma_j^2$, $S_0^2$ is the amplitude reduction factor, $\sigma_j(k)$ is the total phase shift, and $\lambda(k)$ is the photoelectron mean free path. Based on the structural codes ZONCAG and MECZUQ from Cambridge Crystallographic Data Center (CCDC),[16] the values of $F_j(k)$, $\delta_j(k)$, and $\lambda(k)$ were calculated theoretically by a curved wave ab initio procedure in the FEFF7 code.[13] With $S_0$ fixed at unity, we fitted $FT[k^3\chi(k)]$ in the range ~1.7≤R≤~3.7 Å with the fitting parameters $\Delta E_0$ (small variation in $E_0$), $R_j$, $\sigma_j^2$, and $N_j$, using a nonlinear least-square fitting algorithm implemented by FEFFIT program.[14] In the fitting process, $\Delta E_0$ was allowed to vary but confined to be a common value for all scattering paths. Coordination numbers ($N_j$) were systematically varied in the course of the fitting process but were fixed within a given fit. Data fitting quality was evaluated by the goodness-of-fit factor defined as $$R_{fit} = \frac{\sum_{i=1}^{n}\{[\text{Re}(f_i)^2] + [\text{Im}(f_i)]^2\}}{\sum_{i=1}^{n}\{[\text{Re}(\tilde{\chi}_{data i})]^2 + [\text{Im}(\tilde{\chi}_{data i})]^2\}}, \quad (4)$$

where $\tilde{X}=k^3\chi$ and n is the number of evaluations of $f_i$, with $f_i=\tilde{X}_{data\ i}-\tilde{X}_{model\ i}$ (and hence $R_{fit}$) minimized in the nonlinear least-square fitting algorithm.[14]

Best fits of the EXAFS data collected on the TEL-SAM-PmoA(38-49) fusion protein together with the best fits of the ligand structure for the tricopper cluster are displayed in FIG. 30, and the corresponding parameters are summarized in Table 9. Based on model building, the backscattering of C atom(s) around ~3.14 Å may come from contributions of the carboxylates and/or methionines. An estimation of the bond angle ∠Cu—O—Cu=119.5° enables us to rationalize the possibility of the "μ-oxo" group located at the center of the triad with the Cu—O distances of 2.02 Å and the Cu—Cu of 3.49 Å.

TABLE 9

Parameters used in fitting the $k^3$-weighted EXAFS data of TEL-SAM-PmoA(38-49) fusion protein, including the coordination number N, distance R relative to Cu, and relative mean square displacement $\sigma^2$. Fitting ranges are indicated by $\Delta k$ and $\Delta R$, respectively. The fitting quality is evaluated by the goodness-of-fit factors $R_{fit}$, $\chi^2$, and $\chi v^2$ (=$\chi^2/v$), where v is the differences between the number of independent data points and the number of parameters used in the fitting.

TEL-SAM-PmoA(38-49) fusion protein

| Bond Type | N | R (Å) | $\sigma^2$ (Å$^2$) |
|---|---|---|---|
| Cu—O | 3 | 2.02(1) | 0.0038(4) |
| Cu—S | 0.33 | 2.52(2) | 0.004(2) |
| Cu—C | 2 | 3.14(4) | 0.0086(9) |
| Cu—Cu | 2 | 3.49(1) | 0.0086(9) |
| $\Delta k$ (Å$^{-1}$) | [2.55, 12.25] | | |
| $\Delta R$ (Å) | [1.7, 3.7] | | |
| $R_{fit}$ | 1.1% | | |
| $\chi^2$ | 45.70 | | |
| $\chi v^2$ | 7.46 | | |

Best fits of the EXAFS data collected on the solid Cu$^I$Cu$^I$Cu$^I$-HIHAMLTMGDWD complex together with the best fits of the ligand structure for the tricopper cluster are displayed in FIG. 27.

REFERENCES

1 Inventory of U.S. Greenhouse Gas Emissions and Sinks 1990-2009. USEPA, April 2011.

2 S. Freni, G. Calogero and S. Cavallaro, J. Power Sour., 2000, 87, 28-38.

3 A. E. Shilov and G. B. Shul'pin, Chem. Rev., 1997, 97, 2879-2932.

4 S. J. Blanksby and G. B. Ellison, Acc. Chem. Res., 2003, 36, 255-263.

5 J. H. Lunsford, Catalysis Today, 2000, 63, 165-174.

6 M. O. Adebajo and R. L. Frost, In Recent Advances in Catalytic/Biocatalytic Conversion of Greenhouse Methane and Carbon Dioxide to Methanol and Other Oxygenates, InTech; Europe, 2012; p 338.

7 R. S. Hanson and T. E. Hanson, Microbiol Rev., 1996, 60, 439-471.

8 S. I. Chan, K. H. C. Chen, S. S.-F. Yu, C. L. Chen and S. S. J. Kuo, Biochemistry, 2004, 43, 4421-4430.

9 S. I. Chan and S. S.-F. Yu, Acc. Chem. Res., 2008, 41, 969-979.

10 A. L. Feig and S. J. Lippard, Chem. Rev., 1994, 94, 759-805.

11 J. D. Lipscomb, Annu. Rev. Microbiol., 1994, 48, 371-399.

12 A. C. Rosenzweig, C. A. Frederick, S. J. Lippard and P. Nordlund, Nature, 1993, 366, 537-543.

13 N. Elango, R. Radhakrishnan, W. A. Froland, B. J. Wallar, C. A. Earhart, J. D. Lipscomb, and D. H. Ohlendorf, Protein Sci., 1997, 6, 556-568.

14 R. L. Lieberman and A. C. Rosenzweig, Nature, 2005, 434, 177-182.

15 J. B. Vincent, J. C. Huffman, G. Christou, Q. Li, M. A. Nanny, D. N. Hendrickson, R. H. Fong and R. H. Fish, J. Am. Chem. Soc., 1988, 110, 6898-6900.

16 S. I. Chan, Y. J. Lu, P. Nagababu, S. Maji, M. C. Hung, M. M. Lee, I. J. Hsu, P. D. Minh, J. C. H. Lai, K. Y. Ng, S. Ramalingam, S. S.-F. Yu and M. K. Chan, Angew. Chem. Int. Ed., 2013, 52, 3731-3735.

17 P. P.-Y. Chen, R. B.-G. Yang, J. C.-M. Lee and S. I. Chan, Proc. Nat. Acad. Sci. USA, 2007, 104, 14570-14575.

18 S. I. Chan, C. Y.-C. Chien, C. S.-C. Yu, P. Nagababu, S. Maji and P. P.-Y. Chen, J. Catal., 2012, 293, 186-194.

19 P. Nagababu, S. Maji, M. P. Kumar, P. P.-Y. Chen, S. S.-F. Yu and S. I. Chan, Adv. Synth. Catal. 2012, 354, 3275-3282.

20. R. L. Lieberman, A. C. Rosenzweig in Nature 2005, 434, 177-182.

21. S. I. Chan and S. S.-F. Yu in Acc. Chem. Res., 41 (8), 969-979 (2008)

22. S. I. Chan, V. C.-C. Wang, J. C.-H. Lai, S. S.-F. Yu, P. P.-Y. Chen, K. H.-C. Chen, C.-L. Chen, M. K. Chan, Angew. Chem. 2007, 119, 2038-2040; Angew. Chem. Int. Ed. 2007, 46, 1992-1994.

23. S. I. Chan, K. H.-C. Chen, S. S.-F. Yu, C.-L. Chen, S. S.-J. Kuo, Biochemistry, 43, 4421-4430 (2004).

24. Angew. Chem. Int. Ed. 52, 3731-3735 (2013).

25. Catal. Sci. Technol., 4, 930-935 (2014)

[1] D. M. Burness, H. O. Bayer, J. Org. Chem. 1963, 28, 2283.

[2] S. G. Hayashi, M. F. Y. Fujino, M. Sugita, T. Nakao, Chem. Pharm. Bull. 1971, 19, 2003.

[3] S. I. Chan, C. Y.-C. Chien, C. S.-C. Yu, P. Nagababu, S. Maji, P. P.-Y. Chen, J. Catal. 2012, 293, 186.

[4] P. P.-Y. Chen, R. B.-G. Yang, J. C.-M. Lee, S. I. Chan, Proc. Nat. Acad. Sci. USA 2007, 104, 14570.

[5] S. Maji, J. C.-M. Lee, Y.-J. Lu, C.-L. Chen, M.-C. Hung, P. P.-Y. Chen, S. S.-F. Yu, S. I. Chan, Chem. Eur. J. 2012, 18, 3955.

[6] P. Nagababu, S. Maji, M. P. Kumar, P. P.-Y. Chen, S. S.-F. Yu, S. I. Chan, Adv. Synth. Catal. 2012, 354, 3275.

[7] W. C. Chan, P. D. White, in *Fmoc Solid Phase Peptide Synthesis:* (A Practical Approach W. C. Chen, P. D. White, Eds), Oxford Univ. Press, Oxford, UK 2000, p. 41-77.

[8] S. I. Chan, V. C.-C. Wang, J. C.-H. Lai, S. S.-F. Yu, P. P.-Y. Chen, K. H.-C. Chen, C. L. Chen, M. K. Chan, 2007, 46, 1992.

[9] S. I. Chan, S. S.-F. Yu, *Acc. Chem. Res.* 2008, 41, 969.

[10] H.-C. Chen, C.-L. Chen, C.-F. Tseng, S. S.-F. Yu, S.-C. Ke, J.-F. Lee, H. T. Nguyen, S. J. Elliott, J. O. Alben, S. I. Chan, *J. Chin. Chem. Soc.* 2004, 51, 1081.

[11] S. Nauli, S. Farr, Y.-J. Lee, H.-Y. Kim, S. Faham, J. U. Bowie, *Protein Sci.* 2007, 16, 2542.

[12] L. S. Kau, D. J. Spira-Solomon, J. E. Penner-Hahn, K. O. Hodgson, E. I. Solomon, *J. Am. Chem. Soc.* 1987, 109, 6433.

[13] M. Li, Y.-S. Huang, U-S. Jeng, I.-J. Hsu, Y. C. S. Wu, Y.-H. Lai, C.-H. Su, J.-F. Lee, Y. Wang, C.-C. Chang, *Biophys. J.* 2009, 97, 609.

[14] M. Newville, *J. Synchrotron Rad,* 2001. 8, 322.

[15] O. Kahn, Molecular Magnetism, VCH Publishers, New York, 1993, pp. 1-380.

[16] CCDC is the abbreviation of the Cambridge Crystallographic Data Center at the website http://www.ccdc.cam.ac.uk/

[17] S. I. Zabinsky, J. J. Rehr, A. Ankudinov, R. C. Albers, M. J. Eller, *Phys. Rev. B* 1995, 52, 2995.

Statements Regarding Incoporation by Reference and Variations

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A catalytic process for oxidation of a hydrocarbon to generate an oxidation product, said process comprising the steps of:
    contacting said hydrocarbon with a copper catalyst in the presence of an oxidizing agent; thereby generating said oxidation product; and
    regenerating said copper catalyst;
    wherein said copper catalyst comprises a tricopper complex comprising three Cu ions and a ligand (L) having the formula (FX8):

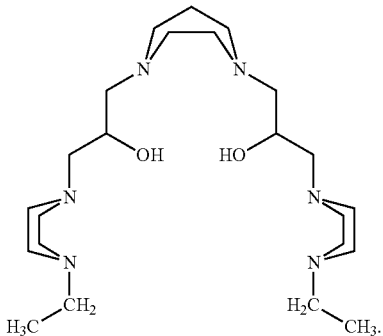

(FX8)

2. The process of claim 1, wherein said hydrocarbon is: a $C_1$-$C_8$ alkane or a $C_2$-$C_8$ alkene and wherein said oxidation product is an alcohol, a ketone or a diol.

3. The process of claim 1, wherein said hydrocarbon is methane, ethane, propane, butane or any combination of these provided in a sample of natural gas.

4. The process of claim 1, wherein said copper catalyst comprises a tricopper complex having the formula $[Cu^I Cu^I Cu^I(L)]^+$, wherein L is said ligand.

5. The process of claim 1, wherein said copper catalyst is contacted with said oxidizing agent, thereby generating an oxygenated activated copper catalyst having the formula $[Cu^{II} Cu^{II}(\mu\text{-}O)_2 Cu^{III}(L)]^+$, wherein L is said ligand.

6. The process of claim 5, wherein reaction of said oxygenated activated copper catalyst and said hydrocarbon results in transfer of an O atom from said oxygenated activated copper catalyst to said hydrocarbon, thereby generating said oxidation product; wherein said O atom is inserted into a C—H bond of said hydrocarbon.

7. The process of claim 6, wherein reaction of said oxygenated activated copper catalyst and said hydrocarbon generates a partially oxidized tricopper complex reaction product; said process further comprising reducing said partially oxidized tricopper complex reaction product so as to regenerate said copper catalyst; wherein said reduced tricopper complex reaction product has the formula $[Cu^I Cu^{II}(\mu\text{-}O)Cu^{II}(L)]^+$, wherein L is said ligand.

8. The process of claim 7, wherein said step of reducing said partially oxidized tricopper complex reaction product is achieved by contacting said partially oxidized tricopper complex reaction product with a reducing agent; wherein said reducing agent is $H_2O_2$, $H_2$, formate or ascorbate.

9. The process of claim 1 characterized by a turnover frequency greater than or equal to $1 \times 10^{-2}$ sec$^{-1}$ and a catalytic efficiency greater than or equal to 50%.

10. The process of claim 1, wherein said copper catalyst further comprises one or more counterions.

11. The process of claim 1, wherein said oxidizing agent is $O_2$, $H_2O_2$ or air.

12. The process of claim 1, wherein said oxidizing agent is provided in a gas phase, a liquid phase or a solution phase; wherein said copper catalyst is a homogenous catalyst; and wherein said copper catalyst, said oxidizing agent and said hydrocarbon are each dissolved in a solvent, wherein said step of contacting said hydrocarbon with a copper catalyst in the presence of an oxidizing agent is carried out in a homogeneous solution comprising said solvent dissolved copper catalyst, said oxidizing agent and said hydrocarbon.

13. The process of claim 1, wherein the concentration of said catalyst in said solution is selected from the range of 0.1-10 mM; the concentration of said hydrocarbon in said solution is selected from the range of 0.1-0.5 M; and the concentration of said oxidizing agent in said solution is selected from the range of 0.05-0.2 M.

14. The process of claim 1, wherein said copper catalyst is a heterogeneous catalyst; wherein said copper catalyst is immobilized on the surfaces of a solid catalyst support scaffold or wherein said copper catalyst is covalently attached to a polymeric support, glass bead, or resin; wherein said oxidizing agent and said hydrocarbon are dissolved in a solvent to generate a solution, wherein said copper catalyst is contacted with said solution.

15. The process of claim 1 providing a process for converting a natural gas into a liquid fuel at a temperature equal to or less than 25° C. and at a pressure equal to or less than 1 atmosphere.

16. The process of claim 1, wherein the step of contacting said hydrocarbon with a copper catalyst in the presence of an oxidizing agent is performed at room temperature.

17. A catalytic process for converting a natural gas into a liquid fuel, said process comprising the steps of:
    contacting methane, ethane, propane or butane in said natural gas with a copper catalyst in the presence of an oxidizing agent; thereby generating said liquid fuel comprising an alcohol, a ketone, a diol or any combination of these; and
    regenerating said copper catalyst;

wherein said copper catalyst comprises a tricopper complex comprising three Cu ions and a ligand (L) having the formula (FX8):
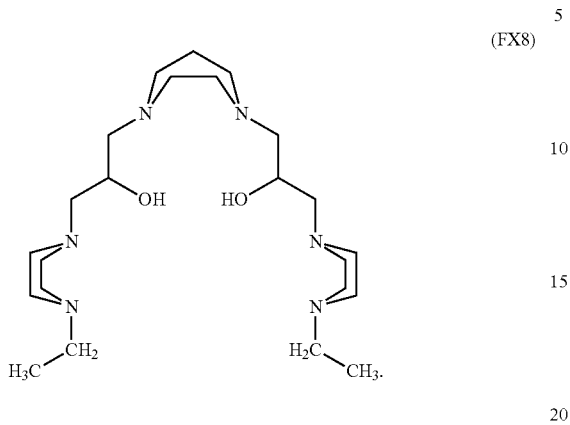
(FX8)
18. The process of claim 17, wherein the step of contacting methane, ethane, propane or butane in said natural gas with a copper catalyst in the presence of an oxidizing agent is performed at room temperature.
\* \* \* \* \*